United States Patent
Nagaoka

(10) Patent No.: US 10,526,644 B2
(45) Date of Patent: Jan. 7, 2020

(54) DETECTION METHOD AND DETECTION DEVICE

(71) Applicant: Sysmex Corporation, Kobe-shi, Hyogo (JP)

(72) Inventor: Kanako Nagaoka, Kobe (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 267 days.

(21) Appl. No.: 15/278,876

(22) Filed: Sep. 28, 2016

(65) Prior Publication Data

US 2017/0145487 A1   May 25, 2017

(30) Foreign Application Priority Data

Sep. 30, 2015 (JP) ................. 2015-194458
Jul. 29, 2016 (JP) ................. 2016-150817

(51) Int. Cl.
| | | |
|---|---|---|
| C12Q 1/68 | (2018.01) | |
| C07H 21/00 | (2006.01) | |
| G01N 33/53 | (2006.01) | |
| C12Q 1/6832 | (2018.01) | |
| G01N 33/543 | (2006.01) | |
| C12Q 1/6816 | (2018.01) | |
| B03C 1/28 | (2006.01) | |
| B03C 1/30 | (2006.01) | |

(52) U.S. Cl.
CPC ......... *C12Q 1/6832* (2013.01); *C12Q 1/6816* (2013.01); *G01N 33/54326* (2013.01); *G01N 33/54333* (2013.01); *G01N 33/54386* (2013.01); *B03C 1/288* (2013.01); *B03C 1/30* (2013.01); *B03C 2201/18* (2013.01); *B03C 2201/26* (2013.01)

(58) Field of Classification Search
CPC . C12Q 1/68; C12Q 1/70; C12Q 19/34; C07H 21/00; G01N 33/53
See application file for complete search history.

(56) References Cited

U.S. PATENT DOCUMENTS

| | | |
|---|---|---|
| 2006/0003320 A1 | 1/2006 | Miller et al. |
| 2008/0191688 A1 | 8/2008 | Kahlman et al. |
| 2009/0311734 A1 | 12/2009 | Greve et al. |
| 2010/0109653 A1 | 5/2010 | Nieuwenhuis et al. |
| 2010/0233822 A1 | 9/2010 | Prins et al. |
| 2010/0253323 A1 | 10/2010 | De Theije et al. |
| 2010/0264913 A1 | 10/2010 | Sandhu |
| 2011/0138890 A1 | 6/2011 | Sakamoto et al. |
| 2011/0281320 A1 | 11/2011 | Saito et al. |
| 2012/0329124 A1 | 12/2012 | Tajima |
| 2013/0088221 A1 | 4/2013 | Van Zon et al. |
| 2013/0105581 A1 | 5/2013 | Kwon et al. |
| 2013/0244238 A1 | 9/2013 | Neely et al. |
| 2014/0120523 A1 | 5/2014 | Lowery, Jr. et al. |

FOREIGN PATENT DOCUMENTS

| | | |
|---|---|---|
| CN | 1431504 A | 7/2003 |
| JP | 2013-238420 A | 11/2013 |

OTHER PUBLICATIONS

Bernard et al., Controlled formation of metallic nanowires via Au nanoparticle ac trapping. Nanotechnology 18:235202(6 pp) (Year: 2007).*

Sinyagin et al., Monte Carlo Computer Simulation of Chain Formation from Nanoparticles. J. Phys. Chem. B 110:7500 (Year: 2006).*

A copy of the Chinese Office Action dated Aug. 29, 2019 in a counterpart Chinese patent application No. 201610833755.9.

A copy of the Communication pursuant to Article 94(3) EPC dated Nov. 6, 2019 in a counterpart European patent application No. 16191383.5.

* cited by examiner

*Primary Examiner* — Ethan C Whisenant

(74) *Attorney, Agent, or Firm* — Brinks Gilson & Lione

(57) ABSTRACT

A detection method for detecting a detection target substance is provided. The method includes a first application step of applying a magnetic field a liquid suspension to link a plurality of magnetic particles in a row from an interior surface of a liquid receiving member that receives the liquid suspension of magnetic particles to which a detection target substance is bound, a second application step of bringing the linked magnetic particles near the interior surface while the magnetic field is applied to the liquid suspension, and a detection step of detecting the detection target substance bound to the magnetic particles brought near the interior surface by the second application step, wherein the direction of the magnetic field applied to the liquid suspension is altered so the linked magnetic particles approach the interior surface in the second application step.

16 Claims, 42 Drawing Sheets

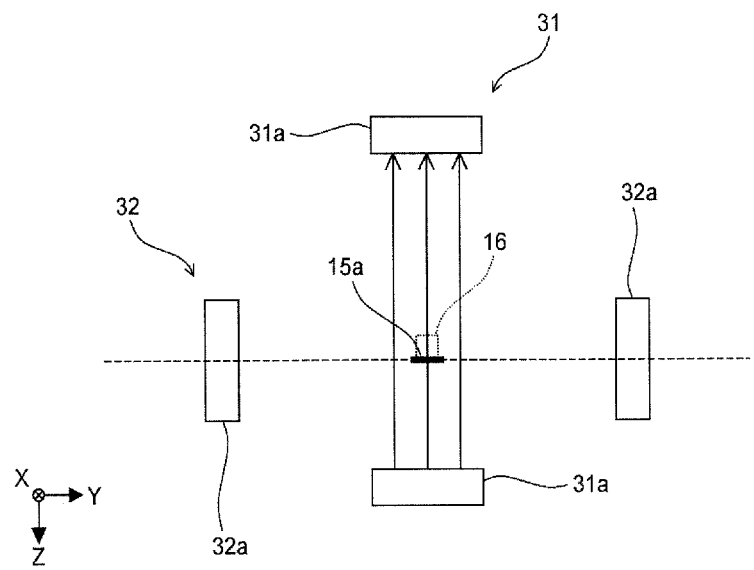
FIG. 4A  Modification
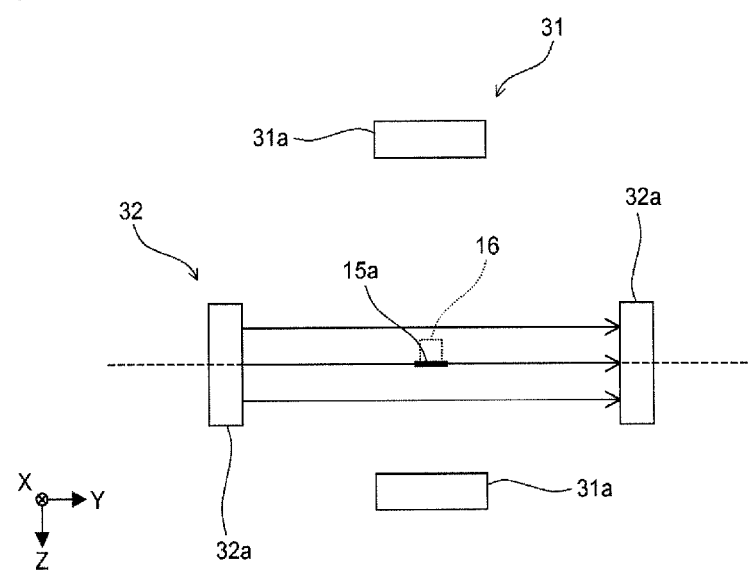
FIG. 4B  Modification

FIG. 5A  1st state
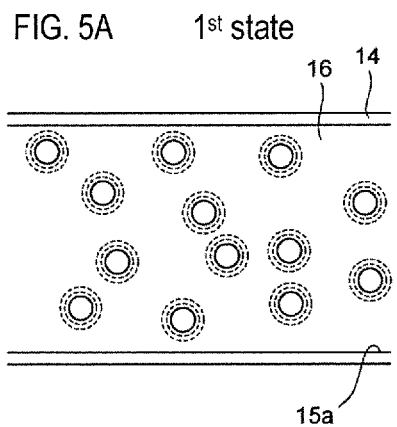
FIG. 5B  1st state
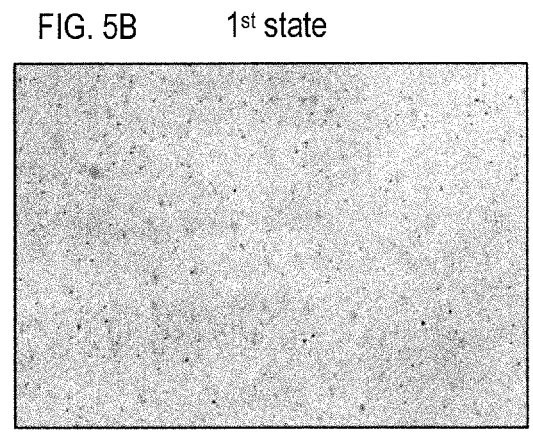
FIG. 5C  2nd state
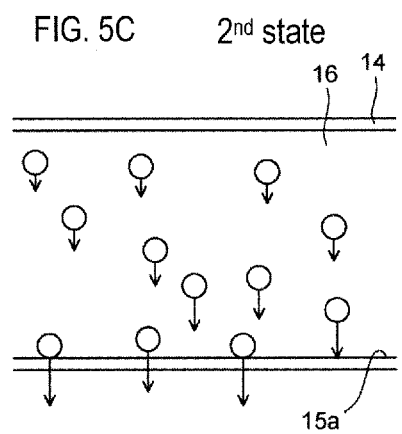
FIG. 5D  2nd state
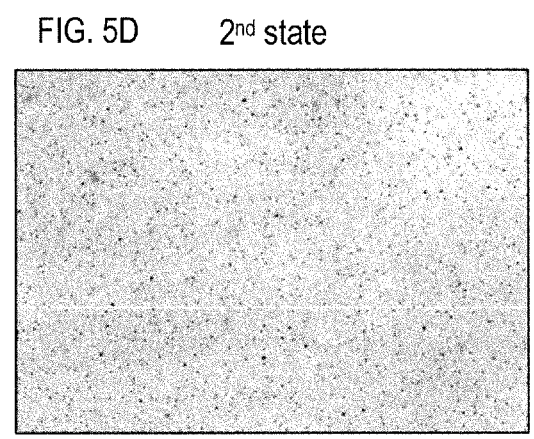
FIG. 5E  3rd state
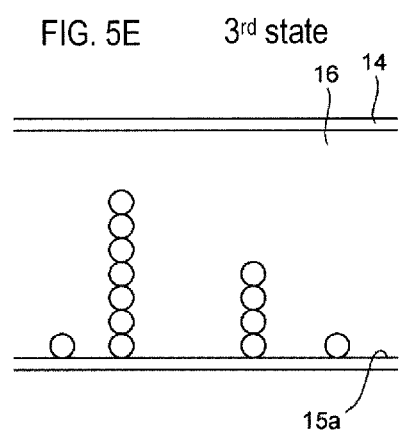
FIG. 5F  3rd state
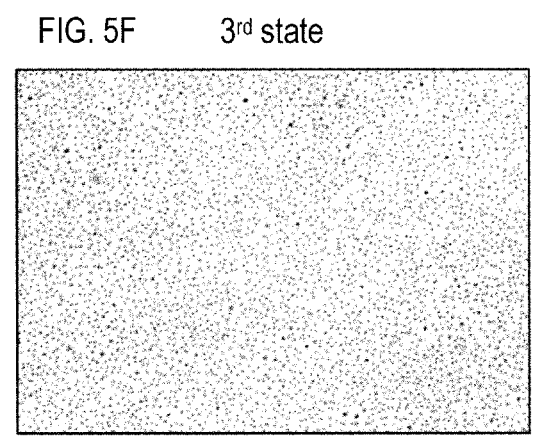

FIG. 6A 4th state
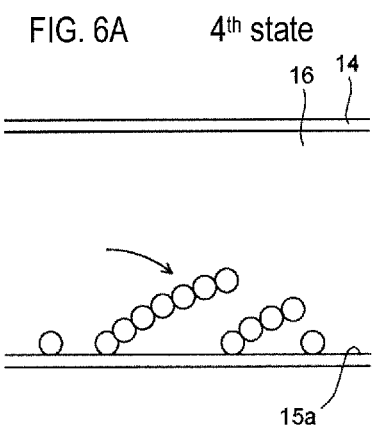
FIG. 6B 4th state
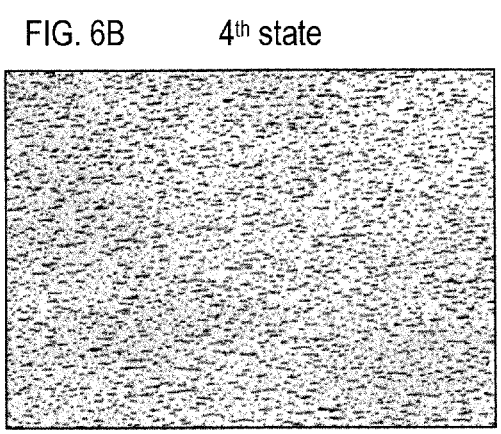
FIG. 6C 5th state
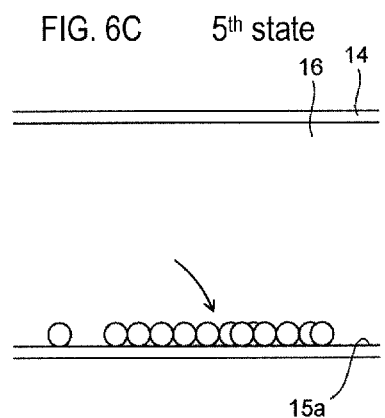

FIG. 7A  1st state
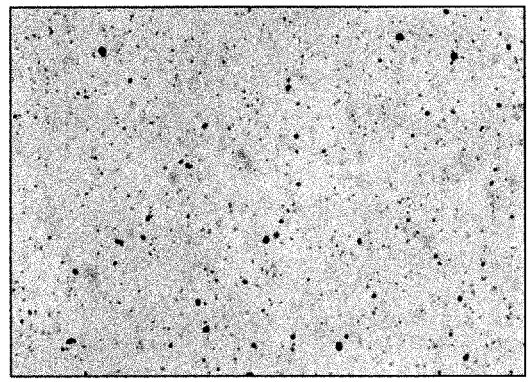
FIG. 7B  2nd state
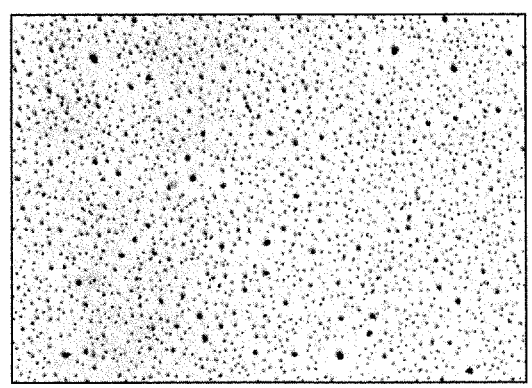
FIG. 7C  4th state
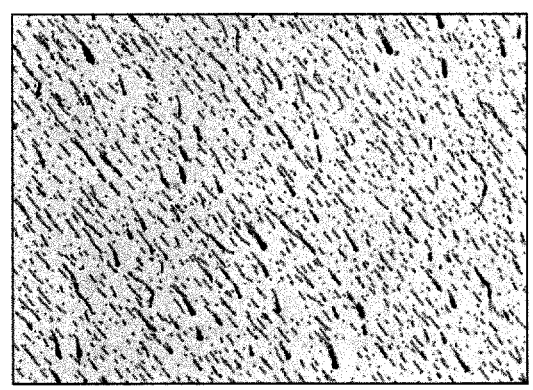

FIG. 10A    Modification
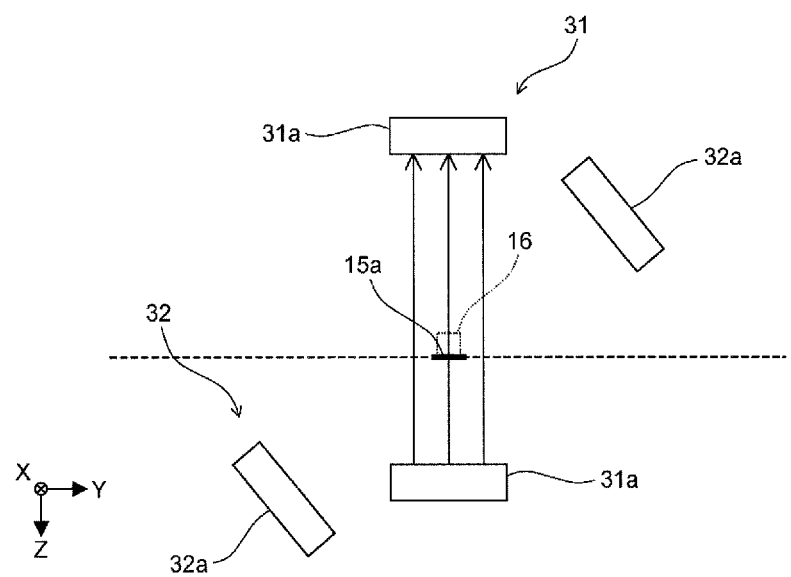
FIG. 10B    Modification
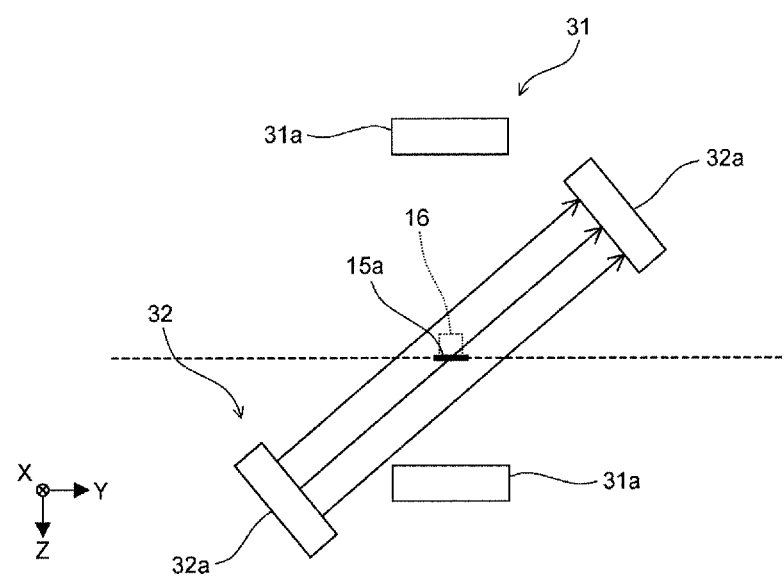

FIG. 11A 6th state
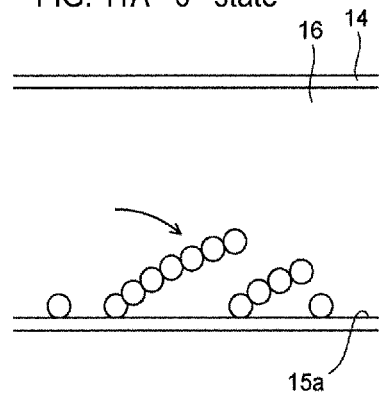
FIG. 11B 6th state
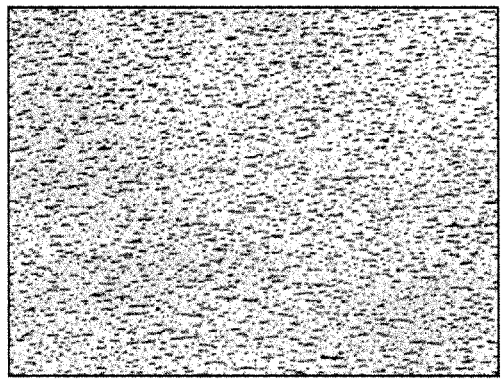
FIG. 11C 7th state
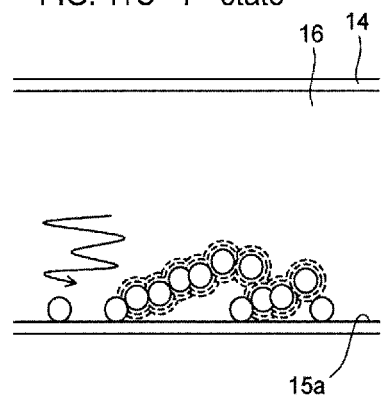
FIG. 11D 7th state
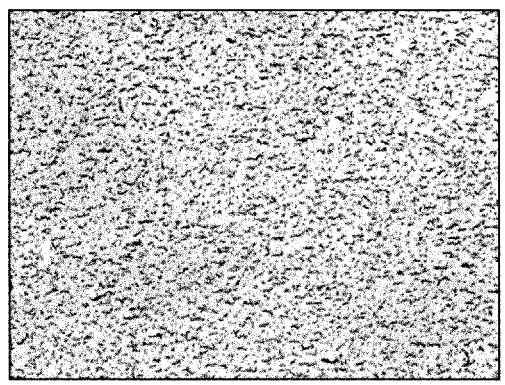

FIG. 12A 8th state
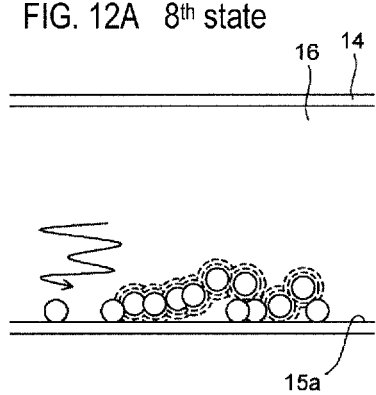
FIG. 12B 8th state
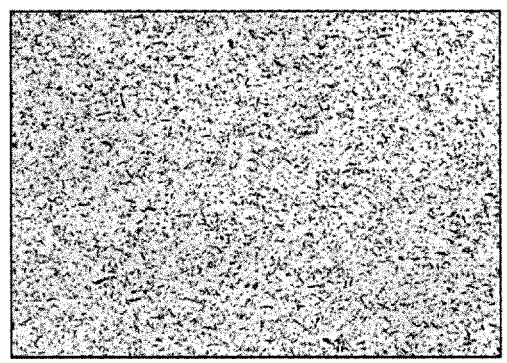
FIG. 12C 9th state
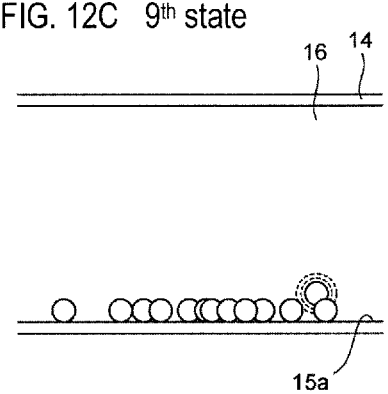
FIG. 12D 9th state
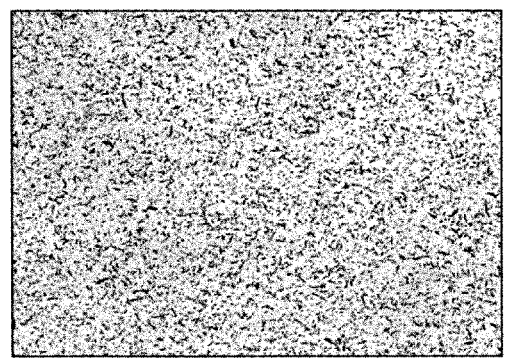

FIG. 13B Fluorescent image of reference example
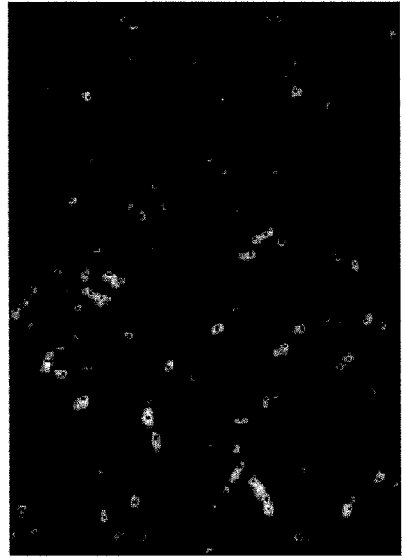
FIG. 13D Extraction image of reference example
FIG. 13A Fluorescent image of 2nd embodiment
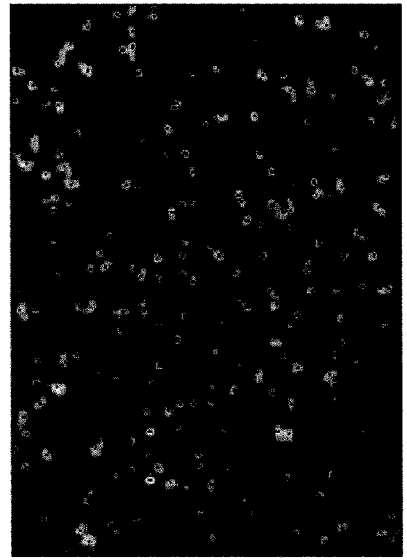
FIG. 13C Extraction image of 2nd embodiment

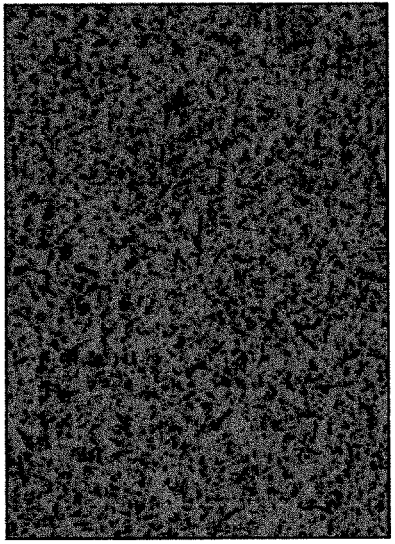
FIG. 14B Bright-field image of reference example
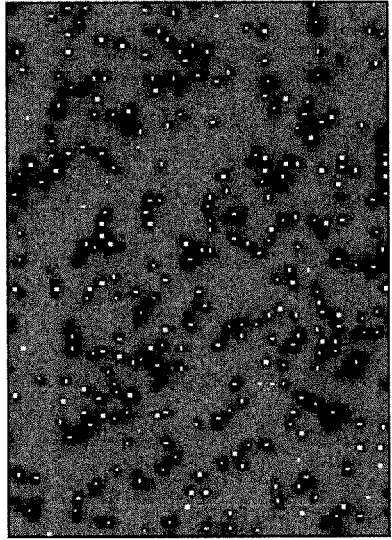
FIG. 14D Extraction image of reference example
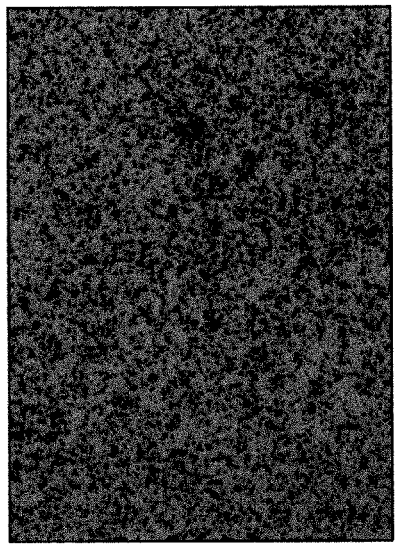
FIG. 14A Bright-field image of 2nd embodiment
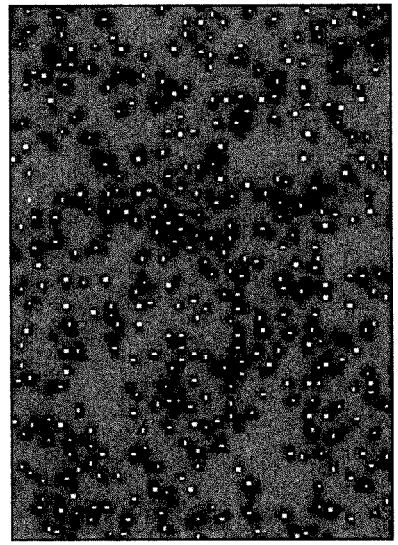
FIG. 14C Extraction image of 2nd embodiment Single particles Linked particles

| | Particles | Surface active agent | Cationization | Dispersion rate (%) |
|---|---|---|---|---|
| 1st Condition | Surface active agent | NO | NO | 0.7 |
| 2nd Condition | Surface active agent | YES | NO | 15.4 |
| 3rd Condition | Surface active agent | YES | YES | 18.5 |

FIG. 16A 1st condition: Pre-dispersion
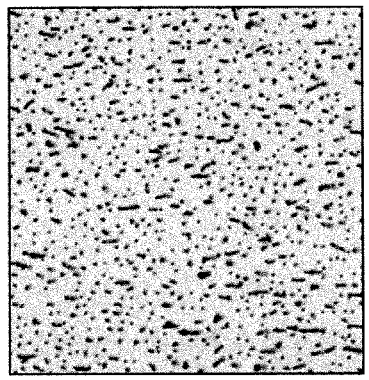
FIG. 16B 1st condition: Post-dispersion
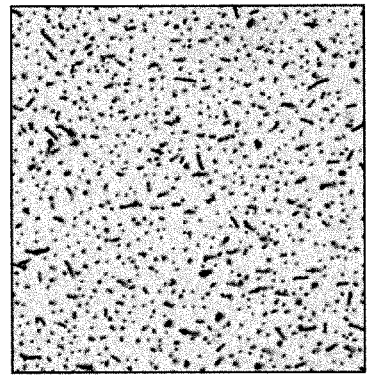
FIG. 16C 2nd condition: Pre-dispersion
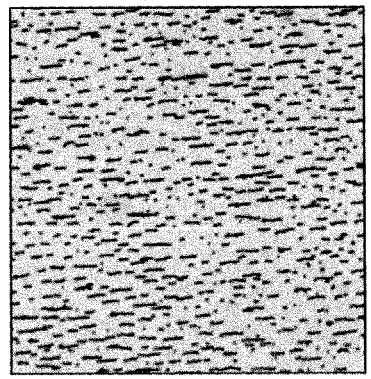
FIG. 16D 2nd condition: Post-dispersion
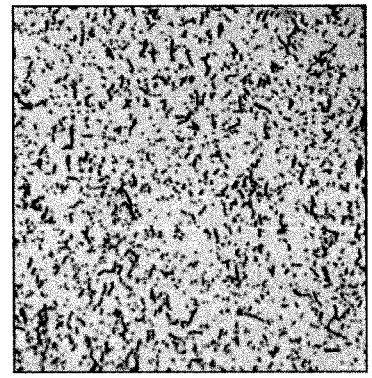
FIG. 16E 3rd condition: Pre-dispersion
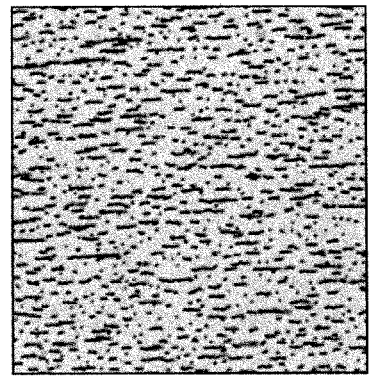
FIG. 16F 3rd condition: Post-dispersion
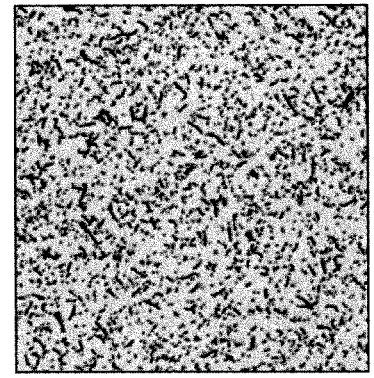

| Surface active agent | Cationization | Dispersion rate (%) |
|---|---|---|
| TritonX-100 0.1% | YES | 24.6 |
| Brij35 0.05% | YES | 22.9 |
| Tween20 0.1% | YES | 18.5 |
| Pluronic F-68 0.1% | YES | 21.4 |
| n-Dodecyl-β-D-maltoside 0.01% | YES | 29.2 |

FIG. 17

FIG. 21A Modification
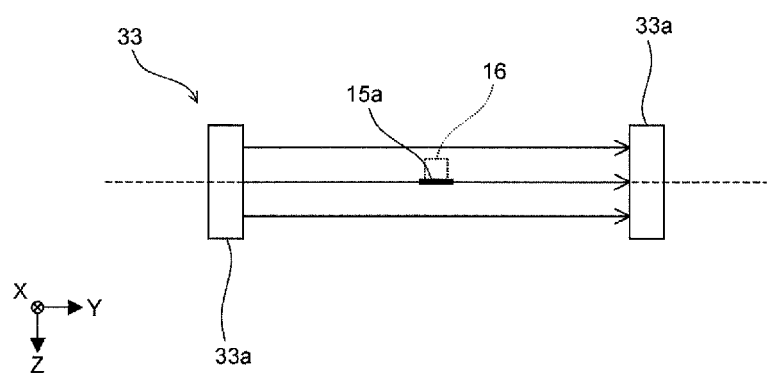
FIG. 21B Modification
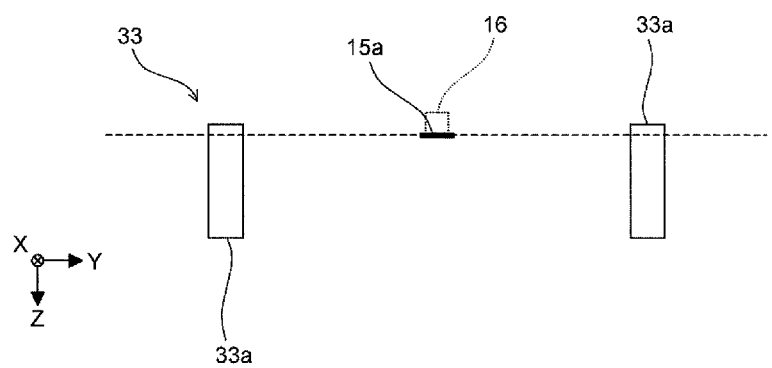

FIG. 33A Extraction-analysis process
FIG. 33B Display process
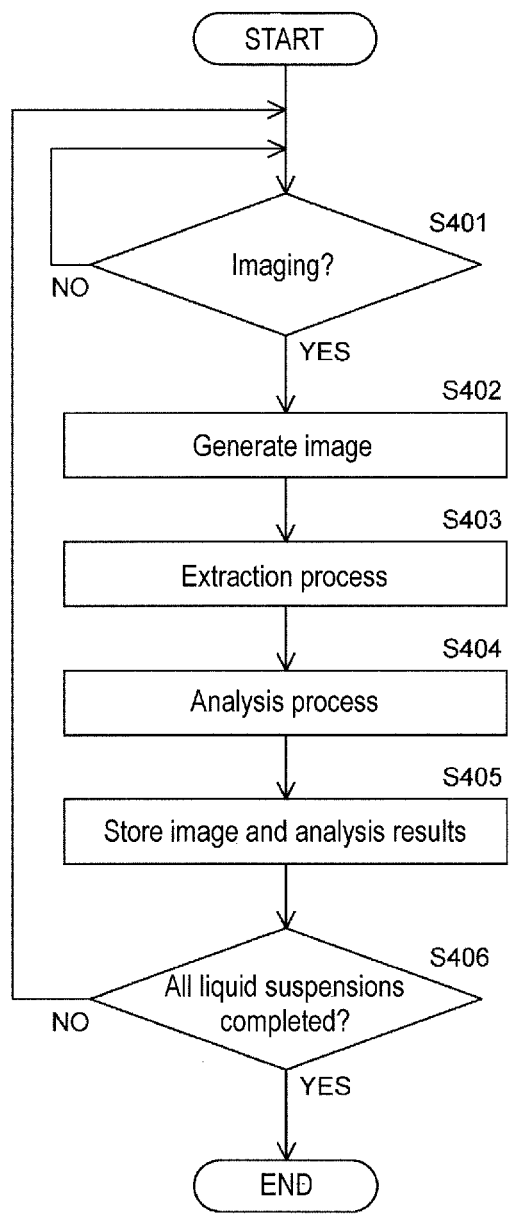
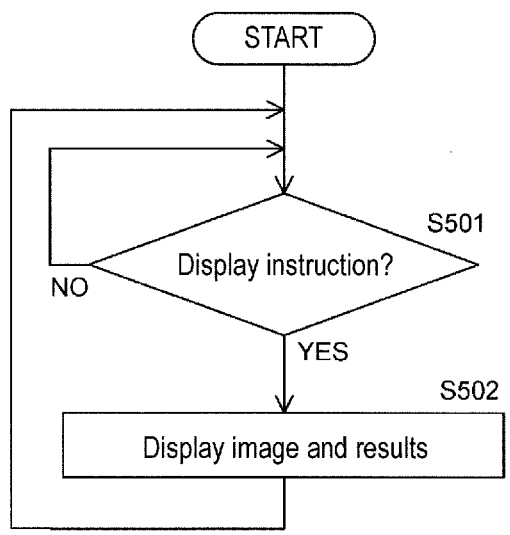

DETECTION METHOD AND DETECTION DEVICE

RELATED APPLICATIONS

This application claims priority from prior Japanese Patent Application No. 2015-194458, filed on Sep. 30, 2015, entitled "Detection method and detection device" and prior Japanese Patent Application No. 2016-150817, filed on Jul. 29, 2016, entitled "Detection method and detection device", the entire contents of which are incorporated herein by reference.

BACKGROUND OF THE INVENTION

1. Field of the Invention

The invention relates to a detection method and detection device.

2. Description of the Related Art

Art for imaging dispersed magnetic particles bound a detection target substance on a substrate is known as a technique for examining a detection target substance such as nucleic acid and proteins that are bound to magnetic particles. For example, U.S. Patent Application Publication No. 2009/311734 discloses an analytic imaging method that aligns magnetic particles bound to detectably labeled rare target cells on a slide based on a magnetic collection method, images the magnetic particles on the slide, and detects and counts the rare target cells.

SUMMARY OF THE INVENTION

However, magnetic particles may overlap on the slide when the magnetic particles in a sample are collected on a slide using magnetism, becoming attached on the slide and the detection target substance is then detected as in the analytic imaging method of U.S. Patent Application Publication No. 2009/311734. It is therefore difficult to detect the detection target substance with substantial precision.

A first aspect of the invention relates to a detection method for detecting a detection target substance. The detection method of the embodiment includes a first application step of applying a magnetic field to a liquid suspension to link a plurality of magnetic particles in a row from an interior surface of a liquid receiving member that receives the liquid suspension of magnetic particles bound to a detection target substance, a second application step of bringing the linked magnetic particles near to the interior surface while the magnetic field is applied to the liquid suspension, and a detection step of detecting the detection target substance bound to the magnetic particles brought near the interior surface by the second application step.

In the detection method of the embodiment, the "interior surface" is a surface on which the magnetic particles in the liquid suspension are arranged when detecting the detection target substance. The "interior surface" may be, for example, the surface of a glass slide on which the liquid suspension is titrated, or may be the bottom surface of a well (concavity) provided on a plate. When the liquid suspension arranged on the surface of a glass slide, bottom surface of a well or the like is covered with a cover, the surface of the cover on the side in contact with the liquid suspension also may be considered the "interior surface." When a using a housing part to house the liquid suspension, for example, either the top surface, bottom surface or side surface configuring the housing space also may be the "interior surface." The housing part in this case need not necessarily have a closed housing space, inasmuch as a portion of the housing part also may connect the inside and outside of the open housing part. When using a flow path through which the liquid suspension can flow, either the bottom surface, top surface, or side surface configuring the interior surfaces of the flow path also may be the "interior surface." "To link magnetic particles in a row" is not limited to linking magnetic particles along a single straight line, but further includes linking magnetic particles along a curved line and bifurcated line. In the second application process, for example, a plurality of linked magnetic particles can be inclined and the linked magnetic particles can be brought near the interior surface by changing the direction of the magnetic field applied in the first application process.

According to the detection method of the embodiment, magnetic particles can be positioned at the interior surface in a state in which the overlap of magnetic particles is suppressed because a magnetic field is applied to the liquid suspension so that the plurality of magnetic particles are linked in a row from the interior surface of the liquid receiving member, and the linked magnetic particles are brought near the interior surface while the magnetic field is applied to the liquid suspension. Therefore, it is possible to accurately detect the detection target substance bound to the magnetic particles. For example, if the interior surface where the magnetic particles are positioned is imaged, it is possible to accurately detect the detection target substance bound to the magnetic particles because it is possible to obtain the captured image in a state in which the overlapping of magnetic particles is suppressed.

A second aspect of the invention relates to a detection device. The detection device of the embodiment is provided with a magnetic field supplying part to apply a magnetic field on the liquid suspension of magnetic particles to which the detection target substance is bound, a light source to irradiate light on the liquid suspension, and a light receiving part to receive the light given off from the liquid suspension due to the irradiation by light. The controller controls the magnetic field supplying part to apply a magnetic field on the liquid suspension so that a plurality of magnetic particles are linked in a row from the interior surface of the liquid receiving member that receives the liquid suspension, and the linked magnetic particles are brought near the interior surface. The controller also detects the detection target substance based on the light received by light receiving part from the liquid suspension that contains the magnetic particles that have been brought near the interior surface by the control of the magnetic field supplying part.

In the detection device of the embodiment, for example, the detection target substance is labeled by fluorescent dye and irradiated by light from a light source causing excitation and fluorescent light is given off from the fluorescent dye and received by the light receiving part. The magnetic field supplying part includes, for example, a permanent magnet, and a mechanism to move the permanent magnet. The controller controls the magnetic field supplying part to apply a magnetic field to the liquid suspension so as to link the plurality of magnetic particles in a row and bring the linked magnetic particles near to the interior surface as in the first embodiment.

In the detection device of the embodiment the magnetic particles also can be positioned at the interior surface while inhibiting any overlap. In this way, the magnetic particles to which the detection target substance is bound can be accurately detected, for example, by imaging fluorescent light given off from the liquid suspension. According to the detection device of the embodiment, therefore, the detection accuracy of the detection device is enhanced.

A third aspect of the invention relates to a detection method for detecting a detection target substance. The detection method of the embodiment includes a magnetic field application step for applying a magnetic field to a liquid suspension to draw magnetic particles to an interior surface of a liquid receiving member that receives the liquid suspension of magnetic particles bound to a detection target substance and link a plurality of magnetic particles in a row in a direction that intersects the direction perpendicular to the interior surface, a detection step of detecting the detection target substance bound to the magnetic particles brought near the interior surface through the magnetic field application step. The liquid suspension contains a surface active agent.

In the detection method of the embodiment, the drawing of the magnetic particles to the interior surface and the linking of the plurality of magnetic particles in a row in a direction that intersects the direction perpendicular to the interior surface proceed in parallel. In the detection method of the embodiment, therefore, the magnetic particles can be positioned at the interior surface in a state in which overlapping is suppressed similar to the first embodiment. The surface active agent also inhibited aggregation of like magnetic particles in the liquid suspension. Therefore, the magnetic particles can be positioned at the interior surface in a state in which overlapping is further suppressed.

A fourth aspect of the invention relates to a detection method for detecting a detection target substance. The detection method of the embodiment includes a magnetic field application step for applying a magnetic field to a liquid suspension to draw magnetic particles to an interior surface of a liquid receiving member that receives the liquid suspension of magnetic particles bound to a detection target substance and link a plurality of magnetic particles in a row in a direction that intersects the direction perpendicular to the interior surface, a detection step of detecting the detection target substance bound to the magnetic particles brought near the interior surface through the magnetic field application step. The interior surface has a surface charge that is opposite the charge of the magnetic particles.

In the detection method of the embodiment, the magnetic particles can be positioned at the interior surface in a state in which overlapping is suppressed similar to the third embodiment. The interior surface also has a surface charge that is opposite the charge of the magnetic particles. Therefore, the detection target substance bound to the magnetic particles can be stably detected because the magnetic particles readily adhered to the interior surface and the position of the magnetic particles adhered to the interior surface readily fixed.

According to the invention, overlapping magnetic particles are suppressed and the target substance bound to the magnetic particles can be more accurately detected.

BRIEF DESCRIPTION OF THE DRAWINGS

FIG. 4A is a schematic view showing the state of the direction of the magnetic field applied to the liquid suspension by a first electromagnet of a modification of the first embodiment is substantially perpendicular relative to the bottom part, and FIG. 4B is a schematic view showing the state of the direction of the magnetic field applied to the liquid suspension by a second electromagnet of a modification of the first embodiment is a direction substantially parallel relative to the bottom part;

FIGS. 5A, 5C and 5E are schematic views of the magnetic particles in the liquid suspension of the first embodiment viewed from a horizontal direction, and FIGS. 5B, 5D and 5F show the bright field image taken from the vertical direction when focus on the liquid suspension is near the bottom part in the first embodiment;

FIGS. 6A) and 6C are schematic views of the magnetic particles in the liquid suspension of the first embodiment viewed from a horizontal direction, and FIG. 6B shows the bright field image taken from the vertical direction when focus on the liquid suspension is near the bottom part in the first embodiment;

FIGS. 7A through 7C show the bright filed image taken when the detection target substance is HBs antigen-antibody complex;

FIG. 10A is a schematic view showing the state of the direction of the magnetic field applied to the liquid suspension by a first electromagnet of a modification of the second embodiment is substantially perpendicular relative to the bottom part, and FIG. 10B is a schematic view showing the state of the direction of the magnetic field applied to the liquid suspension by a second electromagnet of a modification of the second embodiment is an oblique direction;

FIGS. 11A and 11C are schematic views of the magnetic particles in the liquid suspension of the second embodiment viewed from a horizontal direction, and FIGS. 11B and 11D show the bright field image taken from the vertical direction when focus on the liquid suspension is near the bottom part in the second embodiment;

FIGS. 12A and 12C are schematic views of the magnetic particles in the liquid suspension of the second embodiment viewed from a horizontal direction, and FIGS. 12B and 12D show the bright field image taken from the vertical direction when focus on the liquid suspension is near the bottom part in the second embodiment;

FIGS. 13A and 13B show the fluorescent light images obtained in the second embodiment and reference example, respectively, in verification of the detected number of magnetic particles in the second embodiment; and FIGS. 13C and 13D show images of the magnetic particles extracted from the fluorescent light images of the second embodiment and reference example, respectively, in verification of the detected number of magnetic particles in the second embodiment;

FIGS. 14A and 14B show the bright field images obtained in the second embodiment and reference example, respectively, in verification of the detected number of magnetic particles in the second embodiment; and FIGS. 14C and 14D show images of the magnetic particles extracted from the bright field images of the second embodiment and reference example, respectively, in verification of the detected number of magnetic particles in the second embodiment;

FIGS. 16A and 16B show bright field images obtained under a first condition in the second embodiment, FIGS. 16C and 16D show bright field images under a second condition in the second embodiment, and FIGS. 16E and 16F show bright field images under a third condition in the second embodiment;

FIG. 17 shows various examination results of surface active agent in the second embodiment;

FIG. 21A is a schematic view showing the state of the direction of the magnetic field applied to the liquid suspension by an electromagnet of a modification of the third embodiment is substantially parallel relative to the bottom part, and FIG. 21B is a schematic view showing the state of the magnetic field applied to the liquid suspension by the electromagnet of the modification of the third embodiment can be viewed as [0];

FIG. 33A is a flow chart showing the extraction analysis process in the fourth embodiment, and FIG. 33B is a flow chart showing the display process in the fourth embodiment;

DETAILED DESCRIPTION OF THE PREFERRED EMBODIMENTS

First Embodiment

The first embodiment is a detection method to detect a detection target substance bound to magnetic particles, and the invention is applied to a method to detect target DNA bound to magnetic particles. The first embodiment is a method related to the detection process. When the process performed prior to the detection process is referred to as a "pre-process", the target DNA molecules are detected from the liquid suspension manufactured in the pre-process.

Figure 1:
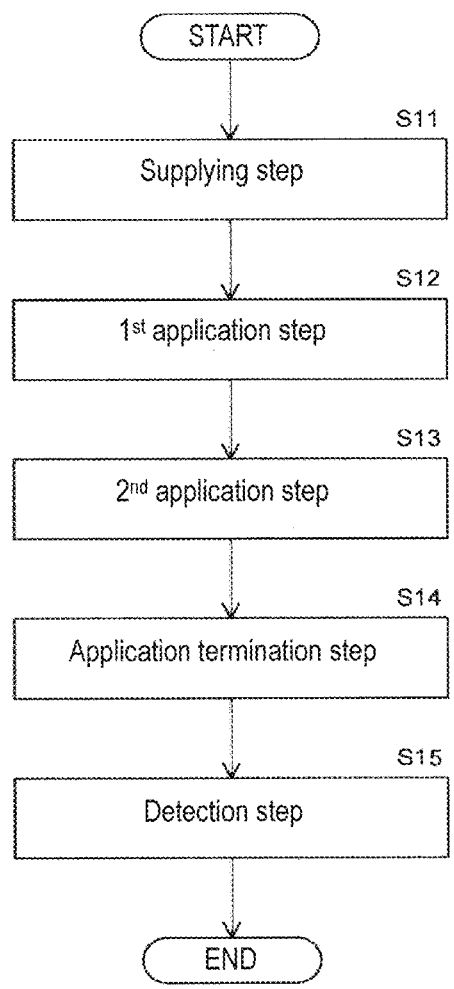
FIG. 1 is a flow chart showing the detection method of a first embodiment.

As shown in FIG. 1, the detection method to detect a detection target substance includes a supplying step, first application step, second application step, application termination step, and detection step. A container 10 shown in FIG. 2 (a) is prepared prior to performing these steps.

Figure 2A:
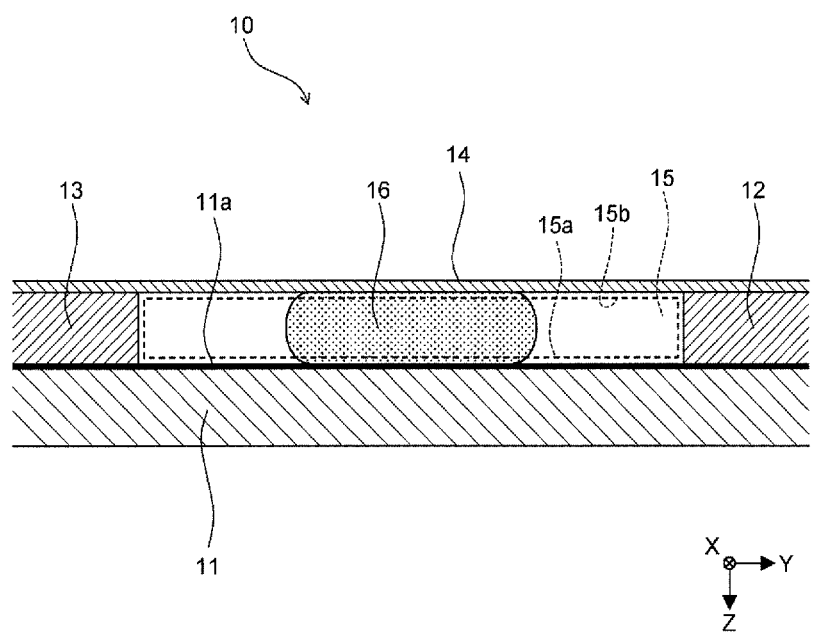
FIG. 2A is a schematic view showing the structure of a container of the first embodiment.

As shown in FIG. 2A, the container 10 is provided with a slide member 11, spacers 12 and 13, and cover 14. In FIG. 2A, the XYZ axes are mutually perpendicular, the XY axes represent the horizontal plane, and the Z-axis positive direction represents a vertical downward direction. In later drawings the XYZ axes are identical to the XYZ axes shown in FIG. 2A.

Note that the container 10 is a liquid receiving member that receives the liquid suspension 16 of magnetic particles to which the detection target substance is bound. The bottom part 15a and top part 15b (described later) correspond to the interior surfaces of the liquid receiving member. In the example shown in FIG. 2A, the container 10 is a housing member that accommodates the liquid suspension 16. A glass slide on which the liquid suspension 16 is dripped also may be used as the liquid receiving member. In this case the surface of the glass slide becomes the surface on which the magnetic particles in the liquid suspension 16 are arranged when detecting the detection target substance. A well (concavity) provided in a plate also may be used as the liquid receiving member. In this case the surface of the well becomes the surface on which the magnetic particles in the liquid suspension 16 are arranged when detecting the detection target substance.

The slide member 11 is a transparent plate-like glass. The top surface 11a of the slide member 11 is a cationic flat surface. The top surface 11a has a positive surface charge imparted by a cationizing process. For example, the top surface 11a also may be cationized by surface processing of the top surface 11a of the slide member 11 using an amino-based silane coupling agent. The spacers 12 and 13 are glass plates positioned at the top surface 11a of the slide member 11. The cover 14 is a thin transparent glass. The cover 14 is positioned at the top surface of the two spacers 12 and 13 which are spaced apart in the horizontal direction. Each part of the container 10 is configured of a material having a relative permeability near [1] so as to not interfere with the magnetic field of the permanent magnet (described later).

When the container 10 is made, a housing part 15 is formed as an open space circumscribed by the top surface 11a of the slide member 11, spacers 12 and 13, and the cover 14. The bottom part 15a of the housing part 15 is part of the top surface 11a, and the top part 15b of the housing part 15 is part of the bottom surface of the cover 14. The bottom part 15a and the top part 15b are surfaces perpendicular to the depth direction of the container 10. The bottom part 15a is a support surface that supports the liquid suspension 16 from below.

The liquid suspension 16 manufactured by preprocessing is dripped on to the top surface 11a from the X-axis positive side or X-axis negative side of the cover 14. In this way the liquid suspension 16 is drawn within the housing part 15 by capillarity. The container 10 holding the liquid suspension 16 is set on the stage of the imaging device so that the bottom surface 15a of the housing part 15 is parallel to the horizontal plane as shown in FIG. 2A.

The bottom part 15a also may be a non-flat surface. For example, the bottom part 15a also may be a curved surface or uneven surface. The monolayered magnetic particles at the bottom surface 15a also may be imaged in a manner described later when an image is obtained by the imaging device as shall be described later.

Figure 2B:
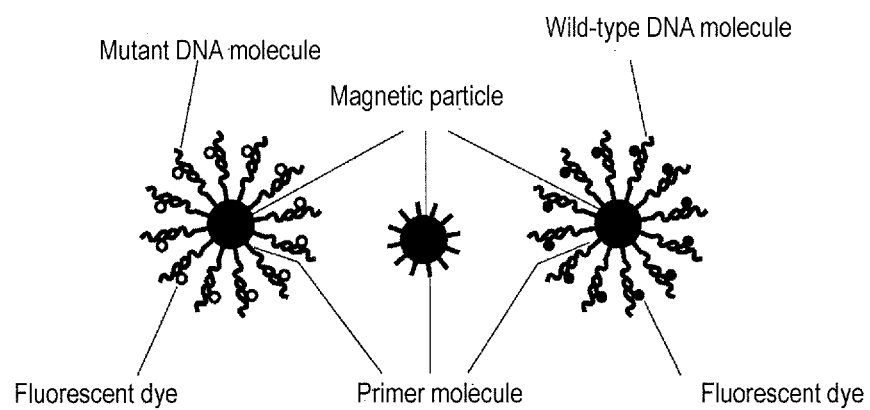
FIG. 2B is a schematic view showing the structure of the magnetic particles of the first embodiment.

The magnetic particles are described referring to FIG. 2B.

The detection target substance in the first embodiment is a target DNA molecule. The magnetic particles are minute magnetic bodies. As shown in the center of FIG. 2B, a plurality of primer molecules that amplify the target DNA molecules are bound to the magnetic particle. In preprocessing, the target DNA molecules are amplified based on the primer molecule bound to the magnetic particle. Accordingly, the liquid suspension 16 prepared by preprocessing includes magnetic particles to which the target DNA molecules are bound as shown on the left and right edges of FIG. 2B, and magnetic particles to which the target DNA molecules are not attached as shown in the center of FIG. 2B.

Both mutant DNA molecules and wild type DNA molecules are the target DNA molecule. In preprocessing, a labeled probe that specifically bonds to mutant DNA molecules binds to the mutant DNA molecule, and a labeled probe that specifically bonds to wild type DNA molecules binds to the wild type DNA molecule. The fluorescent dye of the labeled probe that bonds to the mutant DNA molecule, and the labeled probe that bonds to the wild type DNA molecule respectively are excited to give off fluorescent light when irradiated by light of two mutually different wavelengths. The magnetic particles to which the mutant DNA molecules are bound and the magnetic particles to which the wild type DNA molecules are bound can be respectively recognized through fluorescent labeling by the labeled probe associated with the target DNA.

The magnetic particle to which the primer molecule is bound has a negative charge as shown in the center of FIG. 2B because the primer molecule has a negative charge and the magnetic particles have a negative charge surface. Since the target DNA molecule has a negative charge, the magnetic particles that amplify the target DNA molecules have a negative charge as shown at the left and right edges of FIG. 2B. The bottom part 15a of the housing part 15 has a positive surface charge by cationizing due to part of the top surface 11a as mentioned above. In this way the magnetic particles readily adhere to the bottom surface 15a and the position of the magnetic particles adhered to the bottom part 15a are readily fixed because the bottom part 15a has a surface charge that is opposite the charge taken on by the magnetic particles. Therefore, it is possible to stably detect the detection target substance bound to the magnetic particles.

The liquid suspension 16 is a phosphate buffered saline solution. A surface active agent is added to the liquid suspension 16. The surface active agent of the first embodiment is a nonionic surface active agent, and is, specifically, TritonX-100 (trademarked) reagent. Aggregation of the like magnetic particles is prevented by including the surface active agent in the liquid suspension 16. Although magnetic particles do not readily adhere to the bottom surface 15a of the housing part 15 when the liquid suspension 16 contains surface active agent, the magnetic particles do readily adhere to the bottom surface 15a because the bottom surface 15a has a surface charge that is the opposite of the charge taken on by the magnetic particles.

The liquid suspension 16 does not necessarily contain surface active agent, and the bottom part 15a is not necessarily cationized. That is, when the liquid suspension 16 does not contain surface active agent, the bottom part 15a need not necessarily be cationized since the magnetic particles readily adhere to the bottom part 15a. However, when dispersing the magnetic particles in the liquid suspension 16, it is preferable to include a surface active agent in the liquid suspension 16 to prevent aggregation of like magnetic particles as in the second embodiment described later. In this case the bottom part 15a is preferably cationized to fix the position of the magnetic particles adhered to the bottom part 15a.

Returning to FIG. 1, the supplying step of step S11 is a processing step of supplying the liquid suspension 16 containing magnetic particles to the container 10. Specifically, the liquid suspension 16 is accommodated in the housing part 15 from the X-axis positive side or X-axis negative side of the cover 14. After the liquid suspension 16 is supplied to the container 10, the container 10 is placed on the stage of the imaging device. The first application step of step S12 is a processing step of applying a magnetic field to the liquid suspension 16 from below the container 10 to link the plurality of magnetic particles in a row from the bottom part 15a of the container 10. The second application step of S13 is a processing step in which the linked magnetic particles are brought near the bottom part 15a while the magnetic field is being applied to the liquid suspension 16. Specifically, the second application step of step S13 is a processing step in which the direction of the magnetic field applied to the liquid suspension 16 is changed so as to bring the linked magnetic particles near the bottom part 15a.

Figure 3A:
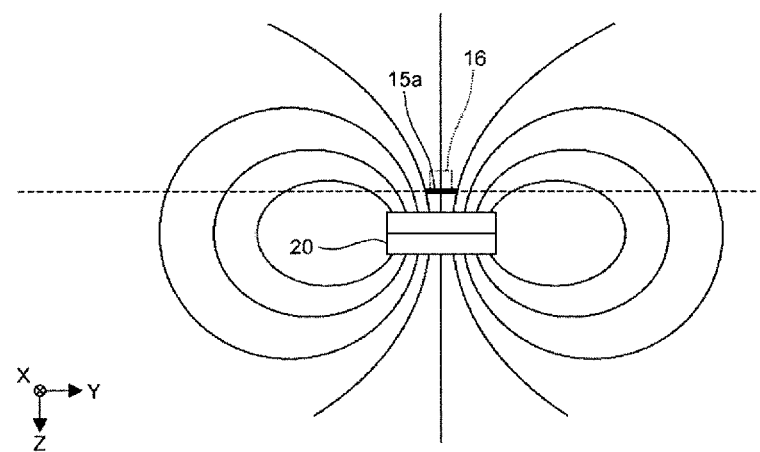
FIG. 3A is a schematic view showing the state of the direction of the magnetic field applied to the liquid suspension by the permanent magnet of the first embodiment is substantially perpendicular relative to the bottom part.

As shown in FIG. 3A, the first application step of step S12 positions the magnetic poles of the permanent magnet 20 below the container 10. Specifically, the permanent magnet 20 is positioned directly under the bottom part 15a. The permanent magnet 20 is arranged so that the N pole is on the topside and the S pole is on the underside. Note that the permanent magnet 20 also may be arranged with the N pole on the underside and the S pole on the topside.

In FIG. 3A the horizontal plane including the bottom part 15a is represented by dashed line, and the lines of magnetic force in the direction of the magnetic field induced by the permanent magnet are represented by the solid lines. The lines of magnetic force emanating from the center of the surface of the permanent magnet 20 extend substantially directly upward, and the lines of magnetic force emanating from the edges of the surface of the permanent magnet 20 are curved in a closed loop that enters the bottom surface of the permanent magnet 20. The magnetic flux density becomes stronger nearer the permanent magnet 20. When the permanent magnet 20 is positioned directly below the bottom part 15a, the direction of the magnetic field applied to the liquid suspension 16 is substantially perpendicular and upward relative to the bottom part 15a. The magnetic particles are drawn to the bottom surface 15a and are linked from the bottom part 15a when the permanent magnet 20 is positioned in this way. The chain formed by the linked magnetic particles extends substantially perpendicular to the bottom part 15a.

In step S12, the permanent magnet 20 does not necessarily have to be positioned directly below the bottom part 15a. The permanent magnet 20 also may be positioned below the container 10 to link the magnetic particles from the bottom part 15a.

In the first application step of step S12, during the time set to establish the chain of linked magnetic particles in the liquid suspension 16 accommodated in the container 10, the application of the magnetic field on the liquid suspension 16 is continuous. That is, the permanent magnet 20 continues to be positioned directly below the bottom part 15a only for a predetermined time. In this way the magnetic particles in the liquid suspension 16 reliably link in a chain from the bottom part 15a.

Figure 3B:
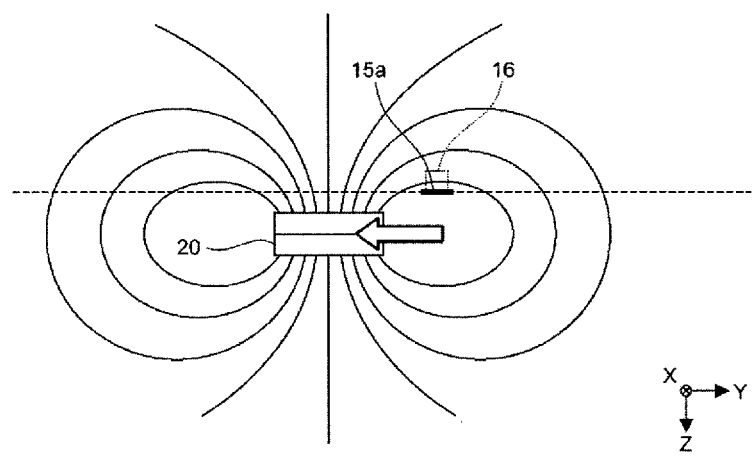
FIG. 3B is a schematic view showing the state of the direction of the magnetic field applied to the liquid suspension by the permanent magnet of the first embodiment is a direction substantially parallel relative to the bottom part.

In the second application step of step S13 shown in FIG. 3B, the magnetic poles of the permanent magnet 20 at the position shown in FIG. 3A are moved away from the liquid suspension 16 held in the container 10. Specifically, the permanent magnet 20 at the position shown in FIG. 3A is moved only a predetermined distance in a parallel direction relative to the bottom part 15a. This changes the direction of the magnetic field so that the direction of the magnetic field applied to the liquid suspension 16 becomes substantially parallel. The chain of magnetic particles approaches the bottom part 15a so as to reside on the bottom part 15a by changing the direction of the magnetic field to be substantially a horizontal direction. Therefore, when the chain of magnetic particles resides on the bottom part 15a, substantially all magnetic particles in the liquid suspension 16 are linked and positioned on the bottom part 15a. The magnetic particles thus are prevented from overlapping in the depth direction of the container 10. The prevention of overlapping magnetic particles in the depth direction of the container 10 is referred to as "monolayering" below.

Returning to FIG. 1, the application termination step of step S14 is a processing step to terminate the application of the magnetic field relative to the liquid suspension 16 and is performed between the second application step and the detection step. Specifically, the magnetic poles of the permanent magnet 20 positioned as shown in FIG. 3B are moved away from the liquid suspension 16 so the magnetic field applied to the liquid suspension 16 by the permanent magnet 20 can be viewed as [0]. At this time the permanent magnet 20 is preferably away from the liquid suspension 16 so as to not change the magnetic field applied to the housing part 15.

In the first embodiment, the magnetic particles are put in a monolayer state at the bottom part 15a by the application process of step S13. Accordingly, the application termination step of step S14 may be omitted. In this case the detection step of step S15 is performed while the permanent magnet 20 is positioned as shown in FIG. 3B.

The detection step of step S15 is a processing step in which an image is obtained by imaging the liquid suspension 16 accommodated in the container 10 using an imaging device, and target DNA molecules of the detection target substance are detected using the obtained image. An upright microscope capable of taking bright field images and fluorescent images may be used as the imaging device. Bright field images and fluorescent images are obtained when the housing part 15 of the container 10 placed on the stage is irradiated from above with light of different wavelengths and the focus is near the bottom part 15a. At this time an image with suppressed overlapping of the magnetic particles is obtained because the magnetic particles form a monolayer on the bottom part 15a.

The obtained bright field image and fluorescent image, for example, may be sent to an analyzer connected to the imaging device. The analyzer detects the mutant DNA molecules and wild-type DNA molecules using the obtained fluorescent image. Specifically, the analyzer specifies the area of bright spots in the fluorescent image based on the fluorescent light given off from the fluorescent dye bound to the mutant DNA molecules. The analyzer detects the mutant DNA molecules by extracting the magnetic particles to which the mutant DNA molecules are bound based on the specified bright spot area. The analyzer also specifies the area of bright spots in the fluorescent image based on the fluorescent light given off from the fluorescent dye bound to the wild-type DNA molecules. The analyzer detects the wild-type DNA molecules by extracting the magnetic particles to which the wild-type DNA molecules are bound based on the specified bright spot area. The steps of steps S11 through S15 therefore end.

In step S15, the operator also may refer to the obtained fluorescent light image to detect the mutant DNA molecules and wild-type DNA molecules. In this case the operator specifies the area of light spots referring to the obtained fluorescent light image. The operator detects the mutant DNA molecules and wild-type DNA molecules by extracting the magnetic particles based on the specified bright spot area. In step S15, mutant DNA molecules and wild-type DNA molecules also may be detected visually by the operator using a microscope.

In step S15, the target DNA molecule of the detection target substance also may be detected without imaging the liquid suspension 16 using the imaging device. For example, the target DNA molecule also can be detected using the measured total amount of fluorescent light by obtaining the total amount of fluorescent light from the liquid suspension 16 via a measuring device.

In the first application step and second application step, the first electromagnet 31 and second electromagnet 32 shown in FIGS. 4A and 4B also may be used instead of the permanent magnet 20. The first electromagnet 31 is provided with a pair of coils 31a, and the second electromagnet 32 is provided with a pair of coils 32a.

The pair of coils 31a of the first electromagnet 31 are positioned on a straight line perpendicular to the bottom part 15a and have the housing part 15 interposed between. The bottom part 15a is arranged between the pair of coils 31a. When power is turned on to the first electromagnet 31, a strong magnetic field is created at the bottom part 15a between the pair of coils 31a, and the magnetic particles in the liquid suspension 16 are drawn to the bottom part 15a. The first electromagnet 31 applies a magnetic field on the liquid suspension 16 in the direction from the lower side of the coil 31a toward the upper side of the coil 31a. Note that the first electromagnet 31 also may apply a magnetic field on the liquid suspension 16 in the direction from the upper side of the coil 31a toward the lower side of the coil 31a.

The pair of coils 321a of the second electromagnet 32 are positioned on a straight line parallel to the bottom part 15a and have the housing part 15 interposed between. The bottom part 15a is arranged at an intermediate position between the pair of coils 32a. The second electromagnet 32 applies a magnetic field on the liquid suspension 16 in the direction from the Y-axis negative side of the coil 32a toward the Y-axis positive side of the coil 32a. The second electromagnet 32 also may apply a magnetic field on the liquid suspension 16 in the direction from the Y-axis positive side of the coil 32a toward the Y-axis negative side of the coil 32a.

The direction of the magnetic field applied to the liquid suspension 16 by the first electromagnet 31 is designated the first direction, and the direction of the magnetic field applied to the liquid suspension 16 by the second electromagnet 32 is designated the second direction. The second direction intersects the first direction. The angle of the second direction relative to the bottom part 15a is smaller than the angle of the first direction relative to the bottom part 15a. The angle of the first direction relative to the bottom part 15a is 90 degrees, and the angle of the second direction relative to the bottom part 15a is [0] degrees. That is, the first electromagnet 31 applies a magnetic field on the liquid suspension 16 at a direction substantially 90 degrees relative to the XY plane, and the second electromagnet 32 applies a magnetic field on the liquid suspension 16 at a direction substantially parallel relative to the XY plane.

The first electromagnet 31 also may be configured by the bottom side coil 31a alone, and the second electromagnet 32 also may be configured by the Y-axis negative side coil 32a alone.

When the first electromagnet 31 and second electromagnet 32 are used, the first electromagnet 31 is actuated and the second electromagnet 32 is stopped in step S12, as shown in FIG. 4A. In this way the direction of the magnetic field applied to the liquid suspension 16 becomes substantially perpendicular and upward relative to the bottom part 15a similar to when the permanent magnet 20 is used. In step S13, the first electromagnet 31 is stopped and the second electromagnet 32 is actuated as shown in FIG. 4B. In this way the direction of the magnetic field applied to the liquid suspension 16 becomes substantially parallel similar to when the permanent magnet 20 is used. In step S14, the second electromagnet 32 is stopped. In this way the application of the magnetic field relative to the liquid suspension 16 is stopped, and the magnetic field applied to the liquid suspension 16 becomes [0].

The monolayering of the magnetic particles is described below referring to FIGS. 5C through 6C. The circles schematically represent magnetic particles in FIGS. 5A, 5C, 5E and FIGS. 6A and 6C. In the bright field images of FIGS. 5B, 5D, 5F, and FIG. 6B, the black dots are magnetic particles.

As shown in FIG. 5A, in a first state the magnetic particles are substantially evenly distributed between the cover 14 and the bottom part 15a immediately after the liquid suspension 16 is supplied to the container 10. This time the aggregation of the magnetic particles is prevented and the magnetic particles are substantially dispersed as individual particles because a surface active agent is included in the liquid suspension 16. As shown in FIG. 5B, the outline of the magnetic particles positioned near the bottom part 15a of the housing part 15 becomes clear in the perpendicular direction. When the liquid suspension 16 is supplied to the container 10, the magnetic particles slowly approach the bottom part 15a due to gravity while exhibiting random movement according to Brownian motion.

As shown in FIG. 5C, in a second state the magnetic particles start to move along the direction of the magnetic field toward the bottom part 15a immediately after the permanent magnet 20 is positioned directly below the bottom part 15a. The direction of the arrows in FIG. 5C indicate the direction of the magnetic field applied to the magnetic particles, and the length of the arrows corresponds to the strength of the magnetic field. The magnetic field applied to the magnetic particles becomes stronger near the permanent magnet 20. As shown in FIG. 5D, the number of magnetic particles that have a clear outline is greater than in FIG. 5B.

As shown in FIG. 5E, in a third state the magnetic particles are linked in a chain from the bottom part 15a immediately after a predetermined time has elapsed since the permanent magnet 20 was positioned directly under the bottom part 15a. The chain formed by the linked magnetic particles extends substantially perpendicular to the bottom part 15a. As shown in FIG. 5F, the magnetic particles that have a clear outline are more numerous than in FIG. 5D.

As shown in FIG. 6A, in a fourth state the chain of magnetic particles approaches the bottom part 15a when the permanent magnet 20 is between the position of FIG. 3A and the position of FIG. 3B. In other words, the chain of magnet particles is inclined from the perpendicular direction toward the bottom part 15a. This time the bottom part 15a has a positive charge, and since the magnetic particles have a negative charge, the magnetic particles in contact with the bottom part 15a among the linked chain of magnetic particles are attracted to the bottom 15a by Coulomb force between the bottom part 15a and magnetic particles so as to be fixed in position on the bottom 15a. In this way the linked magnetic particles are inclined relative to the bottom part 15a and do not flow in the horizontal direction even when the permanent magnet 20 moves in the horizontal direction. As shown in FIG. 6B, the linked magnetic particles are inclined relative to the bottom part 15a.

As shown in FIG. 6C, in a fifth state the chain of magnetic particles lies on the bottom part 15a immediately after the permanent magnet 20 has moved a predetermined distance in the horizontal direction. The like chains do not overlap since magnetic particles mutually have a negative charge. In this way the magnetic particles in the liquid suspension 16 form a monolayer on the bottom part 15a. After the fifth state, the magnetic particles maintain position on the bottom part 15a since the monolayer of magnetic particles on the bottom part 15a cannot move above the bottom part 15a due to the Coulomb for between the magnetic particles and the bottom part 15a even when the application of the magnetic field by the permanent magnet 20 is terminated. Note that the bright field image in the fifth state and the bright field image in the fourth state are substantially identical.

As shown in FIGS. 4A and 4B, the magnetic particles in contact with the bottom part 15a among the linked magnetic particles are drawn to the bottom part 15a by the Coulomb force between the magnetic particles and the bottom part 15a even when the direction of the magnetic field is switched by the first electromagnet 31 and second electromagnet 32, such that the chain of magnetic particles lies on the bottom part 15a the same as in FIG. 6C. Accordingly, the magnetic particles in the liquid suspension 16 form a monolayer on the bottom part 15a even when the first electromagnet 31 and second electromagnet 32 are used.

In this way, according to the first embodiment, overlapping magnetic particles are prevented and a fluorescent light image can be obtained since the magnetic particles form a monolayer on the bottom part 15a. Therefore, the target DNA molecules bound to the magnetic particles can be accurately detected. Since the magnetic particles are drawn to the bottom part 15a when the magnetic field is applied to the housing part 15, a long time for monolayering of the magnetic particles on the bottom part 15a is unnecessary. Hence, the target DNA molecules bound to the magnetic particles can be rapidly detected based on the liquid suspension 16 prepared by the preprocessing. The container 10 to which the liquid suspension 16 is supplied is fabricated simply without performing a detailed process as was described referring to FIG. 2A. In this way the magnetic particles in the liquid suspension 16 can be monolayered on the bottom part 15a and the target DNA molecules bound to the magnetic particles can be detected while reducing the cost of the container 10.

Although the detection target substance has been described as a target DNA molecule, the detection target substance also may be another substance that can be bound to a magnetic particle. The detection target substance also may be, for example, a biopolymer such as nucleic acid, protein and the like, and also may be a cell. In this case also, the magnetic particles to which the detection target substance are bound are monolayered on the bottom part 15a.

As shown in FIGS. 7A through 7C, HBs Antigen-antibody complex solid-phase magnetic particles similarly can be monolayered on the bottom part 15a of the housing part 15 when HBs antigen-antibody complex, a type of protein, is the detection target substance. As shown in FIG. 7A, the magnetic particles evenly distributed in the liquid suspension 16 are linked in a chain from the bottom part 15a, as shown in FIG. 7B. The chain of magnetic particles approaches the bottom part 15a by inclining the direction of the magnetic field, such that the linked magnetic particles incline relative to the bottom part 15a, as shown in FIG. 7C. In this case also, the HBs Antigen-antibody complex can be accurately detected since the fluorescent image is obtained while preventing overlap of the magnetic particles.

Second Embodiment

In the first embodiment the magnetic particles are in a monolayered state on the bottom part 15a, in mutual chain-like contact. In this case, if the magnetic particles with the bound target DNA molecules are a low percentage of all magnetic particles, the contact of like magnetic particles with bound target DNA molecules may be rare within the chain of magnetic particles. Accordingly, the target DNA molecules bound to the magnetic particles can be accurately detected. However, when there is a high percentage of magnetic particles with bound target DNA molecules, the is readily contact among those magnetic particles with bound target DNA molecules. In this case, it is necessary that as far as possible like magnetic particles are not in contact on the bottom part 15a.

Figure 8:
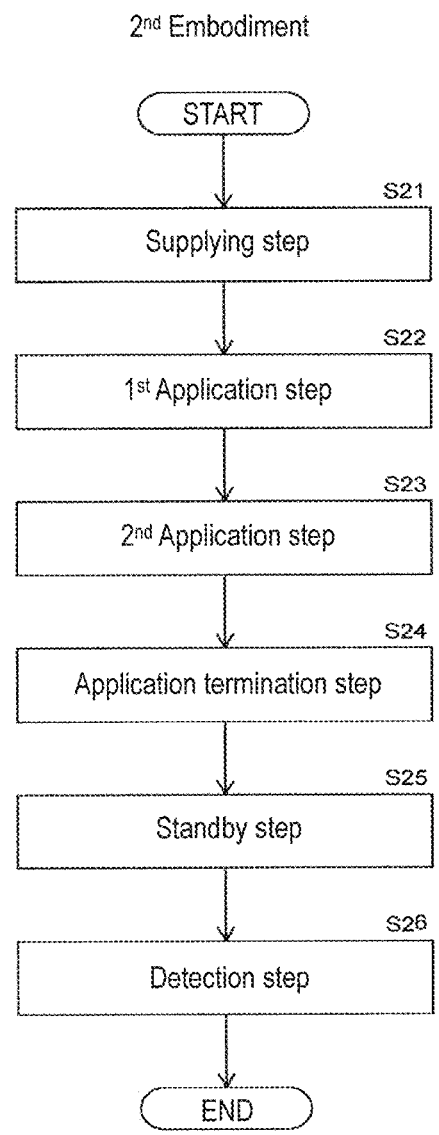
FIG. 8 is a flow chart showing the detection method of a second embodiment.

In the second embodiment, contact among like magnetic particles is inhibited by dispersing the magnetic particles on the bottom part 15a by terminating the application of the magnetic field relative to the magnetic particles after the chain of magnetic particles is inclined. As shown in FIG. 8, the detection method of the second embodiment includes a supplying step, first application step, second application step, application termination step, standby step, and detection step. That is, a standby step is added in the second embodiment compared to the first embodiment. The container 10 shown in FIG. 2A also is prepared prior to performing these steps in the second embodiment.

Figure 9A:
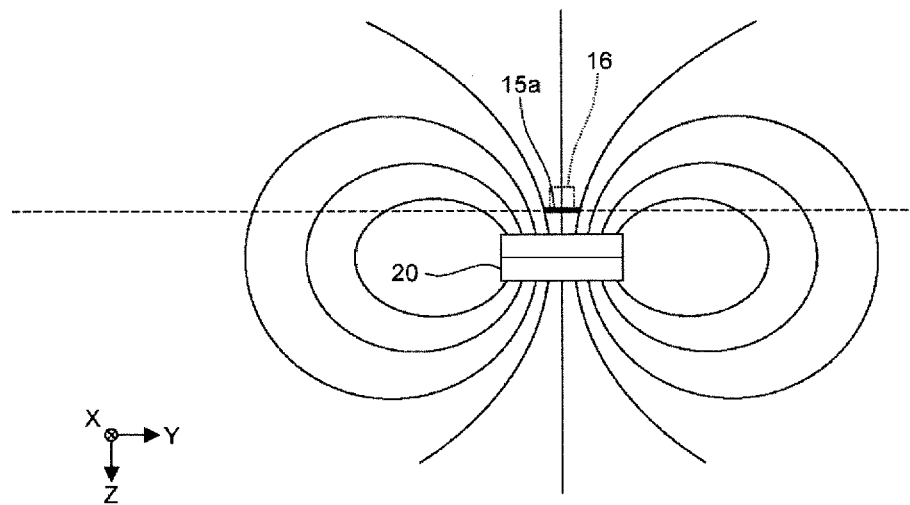
FIG. 9A is a schematic view showing the state of the direction of the magnetic field applied to the liquid suspension by the permanent magnet of the second embodiment is substantially perpendicular relative to the bottom part.

The supplying step of step S21 is a processing step of supplying liquid suspension 16 containing magnetic particles to the container 10 in the same manner as step S11 of the first embodiment. After the liquid suspension 16 is supplied to the container 10, the container 10 is placed on the stage of the imaging device the same as the first embodiment. The first application step of step S22 is a processing step of applying a magnetic field to the liquid suspension 16 from below the container 10 to link the plurality of magnetic particles in a row from the bottom part 15a of the container 10 as shown in FIG. 9A, the same as step S12 of the first embodiment. The second application step of S23 is a processing step in which the linked magnetic particles are brought near the bottom part 15a while the magnetic field is being applied to the liquid suspension 16 the same as the second application step of the first embodiment. Specifically, the second application step of step S23 is a processing step in which the direction of the magnetic field applied to the liquid suspension 16 is changed so as to bring the linked magnetic particles near the bottom part 15a.

Figure 9B:
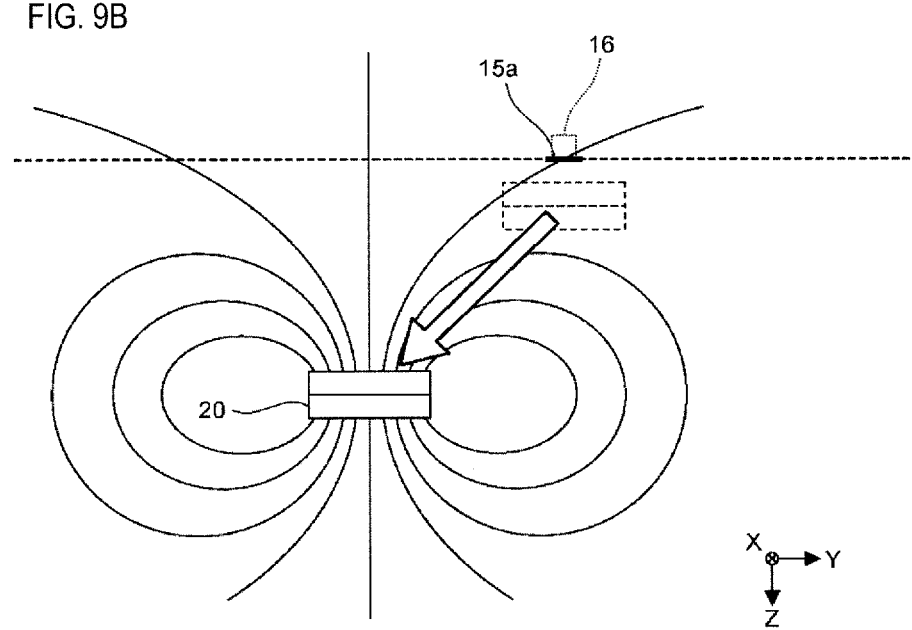
FIG. 9B is a schematic view showing the state of the direction of the magnetic field applied to the liquid suspension by the permanent magnet of the second embodiment is an oblique direction.

In the second application step of step S23 shown in FIG. 9B, the magnetic poles of the permanent magnet 20 at the position shown in FIG. 9A are moved away from the liquid suspension 16 held in the container 10. Specifically, the permanent magnet 20 at the position shown in FIG. 9A is moved only a predetermined distance in a downwardly oblique direction relative to the bottom part 15a. In this way the direction of the magnetic field applied to the liquid suspension 16 is changed so that the direction of the magnetic field applied to the liquid suspension 16 is an oblique direction, that is, a direction having a predetermined angle relative to the horizontal plane. The chain of magnetic particles is brought closer to the bottom part 15a and is extended in an inclined direction relative to the bottom part 15a by changing the direction of the magnetic field to an oblique direction.

Returning to FIG. 8, the application termination step of step S24 is a processing step to terminate the application of the magnetic field relative to the liquid suspension 16 and is performed between the second application step and the detection step the same as step S14 of the first embodiment. Specifically, the magnetic poles of the permanent magnet 20 positioned as shown in FIG. 9B are moved away from the liquid suspension 16 so the magnetic field applied to the liquid suspension 16 by the permanent magnet 20 can be viewed as [0]. At this time the permanent magnet 20 is preferably away from the liquid suspension 16 so as to not change the magnetic field applied to the housing part 15. When the application of the magnetic field on the magnetic particles is terminated in this way, the magnetic particles approach the bottom part 15a due to gravity while exhibiting random movement and the chain of magnetic particles become unbound through Brownian motion.

The standby step of step S25 is a processing step of waiting a set time to disperse the magnetic particles in the liquid suspension 16 on the bottom part 15a of the container 10 after the magnetic field application on the liquid suspension is termination. In this way substantially all magnetic particles undergoing Brownian motion in the liquid suspension 16 are positioned on the bottom part 15a. Thus, the magnetic particles are monolayered in a dispersed state on the bottom part 15a. The detection step of step S26 is a processing step of imaging the liquid suspension 16 accommodated in the container 10 using an imaging device, and detecting the target DNA molecules of the detection target substance the same as step S15 of the first embodiment. The steps of steps S21 through S26 therefore end.

In the first application step and second application step, the first electromagnet 31 and second electromagnet 32 shown in FIGS. 10A and 10B also may be used instead of the permanent magnet 20. The first electromagnet 31 and the second electromagnet 32 are identical to the configurations shown in FIGS. 4A and 4B, and only the arrangement of the second electromagnet 32 is changed from the position shown in FIGS. 4A and 4B. The direction of the alignment of the pair of coils 32a is rotated around the X-axis only a predetermined angle from the state shown in FIGS. 4A and 4B. In this case also the bottom part 15a is arranged at an intermediate position between the pair of coils 32a.

As described above, the direction of the magnetic field applied to the liquid suspension 16 by the first electromagnet 31 is designated the first direction, and the direction of the magnetic field applied to the liquid suspension 16 by the second electromagnet 32 is designated the second direction. The angle of the second direction relative to the bottom part 15a also is smaller than the angle of the first direction relative to the bottom part 15a in FIGS. 10A and 10B. In the case of FIGS. 10A and 10B the second direction is inclined relative to the bottom part 15a. That is, the second electromagnet 32 applies a magnetic field on the liquid suspension 16 in an inclined direction relative to the XY plane.

When the first electromagnet 31 and second electromagnet 32 shown in FIGS. 10A and 10B are used, the first electromagnet 31 is actuated and the second electromagnet 32 is stopped in step S22, as shown in FIG. 10A. In this way the direction of the magnetic field applied to the liquid suspension 16 is substantially perpendicular and upward relative to the bottom part 15a. In step S23, the first electromagnet 31 is stopped and the second electromagnet 32 is actuated as shown in FIG. 10B. In this way the direction of the magnetic field applied to the liquid suspension 16 becomes an oblique direction. In step S24, the second electromagnet 32 is stopped. In this way the application of the magnetic field relative to the liquid suspension 16 is stopped, and the magnetic field applied to the liquid suspension 16 becomes [0].

The monolayering of the magnetic particles is described below referring to FIG. 11A through FIG. 12D. The circles shown schematically in FIGS. 11A and 11C, and FIGS. 12A and 12C represent magnetic particles the same as the drawings of the first embodiment. The black dots shown in FIGS. 11B and 11D, and FIGS. 12B and 12D are magnetic particles the same as the drawings in the first embodiment. Note that since the first through third states in the second embodiment are identical to the first through third states of the first embodiment, their descriptions are omitted. In the second embodiment, a sixth state follows the first through third states.

As shown in FIG. 11A, in a sixth state the chain of magnetic particles approaches the bottom part 15a when the permanent magnet 20 is at the position of FIG. 9B. In other words, the chain of magnet particles is inclined from the perpendicular direction toward the bottom part 15a. In this case the magnetic particles in contact with the bottom part 15a among the linked magnetic particles are drawn to the bottom part 15a by the Coulomb force between the magnetic particles and the bottom part 15a so as to be fixed in position on the bottom part 15a. In this way the linked magnetic particles are inclined relative to the bottom part 15a and do not flow in the horizontal direction even when the permanent magnet 20 moves obliquely downward. As shown in FIG. 11B, the linked magnetic particles are inclined relative to the bottom part 15a.

As shown in FIG. 11C, the chain of magnetic particles collapses in a seventh state immediately after the permanent magnet 20 is moved away from the position in FIG. 9B and the application of the magnetic field relative to the liquid suspension 16 is terminated. This time the magnetic particles readily separate as individual particles since a surface active agent is included in the liquid suspension 16. The separated magnetic particles approach the bottom part 15a due to gravity while exhibiting random movement according to Brownian motion. As shown in FIG. 11D, the magnetic particles disperse within the horizontal plane compared to FIG. 11B.

As shown in FIG. 12A, in an eighth state occurring after a predetermined time has elapsed from the seventh state, the magnetic particles approach closer to the bottom part 15a due to gravity while exhibiting random movement according to Brownian motion. As shown in FIG. 12B, the magnetic particles further disperse within the horizontal plane compared to FIG. 11D. The number of magnetic particles with distinct outlines increases compared to FIG. 11D.

As shown in FIG. 12C, in a ninth state occurring a predetermined time from the eighth state, the magnetic particles are positioned on the bottom part 15a. In this way the magnetic particles in the liquid suspension 16 are monolayered on the bottom part 15a. This time the magnetic particles on the bottom part 15a are dispersed and do not aggregate. As shown in FIG. 12D, the magnetic particles are in a dispersed state.

According to the second embodiment the magnetic particles are dispersed in a monolayer on the bottom part 15a. In this way the target DNA molecules bound to the magnetic particles can be accurately detected even if the percentage of magnetic particles with bound target DNA molecules is high.

Verification of Number of Extracted Magnetic Particles

The inventors performed verifications comparing the number of magnetic particles extracted from fluorescent images in the second embodiment and the number of magnetic particles extracted from fluorescent images in a reference example.

In the second embodiment, the inventors linked the magnetic particles from the bottom part 15a, and thereafter inclined the linked magnetic particles relative to the bottom part 15a, terminated the application of the magnetic field, and dispersed the magnetic particles on the bottom part 15a in a monolayer as described above. The inventors then obtained fluorescent images via the second embodiment. Alternatively, the inventors positioned the permanent magnet 20 directly below the liquid suspension 16 and linked the magnetic particles from the bottom part 15a, and thereafter oscillated the linked magnetic particles by swinging the permanent magnet 20 in a reference example. The inventors then terminated the magnetic field by separating the permanent magnet 20 from the liquid suspension 16, and thereafter obtained fluorescent images via the reference example. In both the second embodiment and reference example the fluorescent images were obtained based on the same liquid suspension 16, and based on the fluorescent light given off from the fluorescent dye bound to the mutant DNA molecules.

FIG. 13A is part of the fluorescent image obtained in the second embodiment. FIG. 13B is part of the fluorescent image obtained in the reference example. In FIGS. 13A and 13B, the white areas are the bright spot areas of fluorescent light. As can be understood from FIGS. 13A and 13B, the bright spot areas of the second embodiment are more dispersed than the reference example. In the second embodiment the total area of the bright spot areas is understood to be larger than that of the reference example. The reason the total area of the bright spots is less in the case of the reference example is thought to be stacking of the magnetic particles in the depth direction.

The inventors then used an analyzer to specify bright spot areas in the fluorescent images obtained in the second embodiment and the reference example, and extract the magnetic particles based on the specified bright spot areas.

FIG. 13C is an image showing the magnetic particles extracted from the fluorescent image of the second embodiment. FIG. 13D is an image of the magnetic particles extracted from the fluorescent image of the reference example. FIGS. 13C and 13D are enlarged partial fluorescent images, and the black spots appearing within the white areas indicate the extracted magnetic particles in FIGS. 13C and 13D. As can be understood from FIGS. 13C and 13D, the more numerous magnetic particles were extracted in the second embodiment compared to the reference example. As a result of the extraction of magnetic particles, 48,982 individual magnetic particles were extracted from the fluorescent image of the second embodiment, and 25,328 individual magnetic particles were extracted from the fluorescent image of the reference example.

Therefore, in the second embodiment a larger number of magnetic particles can be extracted compared to when a simple magnetic field was applied as in the reference example. According to the second embodiment the target DNA molecule detection accuracy is increased since the magnetic particles to which the target DNA molecules are bound in the liquid suspension 16 can be extracted more accurately.

The inventors performed verifications comparing the number of magnetic particles extracted from a bright-field image in the second embodiment and the number of magnetic particles extracted from a fluorescent image in a reference example.

FIG. 14A is part of the bright-field image obtained in the second embodiment. FIG. 14B is part of the bright-field image obtained in the reference example. In FIGS. 14A and 14B, the black areas are the magnetic particles that appear in the bright-field images. As can be understood from FIGS. 14A and 14B, the magnetic particles of the second embodiment are more dispersed than in the reference example. In the second embodiment the total area of the areas in which magnetic particles appear also is understood to be greater than that in the reference example. The reason the total area of the areas in which magnetic particles appear is less in the case of the reference example is thought to be stacking of the magnetic particles in the depth direction.

The inventors then used an analyzer to specify areas in which magnetic particles appear in the bright field images obtained in the second embodiment and reference example, and extract the magnetic particles based on the specified areas.

FIG. 14C is an image showing the magnetic particles extracted from the bright-field image of the second embodiment. FIG. 14D is an image of the magnetic particles extracted from the bright-field image of the reference example. FIGS. 14C and 14D are enlarged partial bright-field images, and the white spots appearing within the black areas indicate the extracted magnetic particles in FIGS. 14C and 14D. As can be understood from FIGS. 14C and 14D, the more numerous magnetic particles were extracted in the second embodiment compared to the reference example. As a result of the extraction of magnetic particles, 10,135 individual magnetic particles were extracted from the bright-field image of the second embodiment, and 8,786 individual magnetic particles were extracted from the bright-field image of the reference example.

In this way in the second embodiment more magnetic particles can be extracted the same as the case of the fluorescent image compared to the reference example. Note that the extent of magnetic particles with bound target DNA molecules among all magnetic particles can be ascertained based on the number of magnetic particles extracted in this way and the number of magnetic particles extracted based on the fluorescent image. According to the second embodiment, therefore, the percentage of magnetic particles with bound target DNA molecules can be accurately calculated since the magnetic particles contained in the liquid suspension 16 can be reliably extracted.

Verification of Conditions of Particle Dispersion

The inventors investigated condition of dispersal of magnetic particles on the bottom part 15a of the housing part 15 to determine the dispersion rate by performing the processing step of the second embodiment under the first through third conditions listed below. The dispersion rate used in this investigation is calculated by equation (1) below.

$$\text{Dispersion rate} = 100 \times [(\text{number of single particles post-dispersion}) - (\text{number of single particles pre-dispersion})/(\text{number if linked particles pre-dispersion})] \quad (1)$$

The dispersion rate calculated by equation (1) is a value indicating the extent of dispersion at the bottom part 15a of the magnetic particles linked in a chain by the application of the magnetic field becomes single particles again. It is understood that the larger the dispersion rate value, the more the greater the dispersion of the magnetic particles.

Figures 15A, 15B:
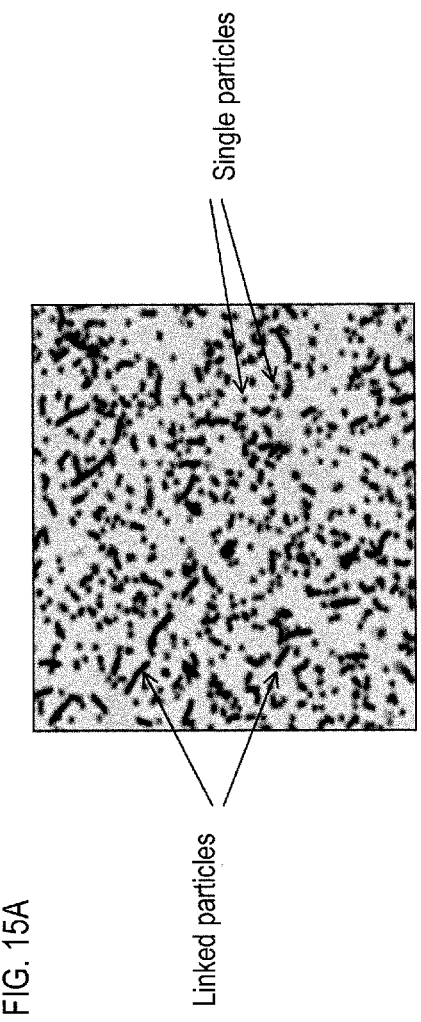
FIG. 15A shows the single particles and linked particles in the second embodiment.
FIG. 15B shows the examination results of conditions of particle dispersion in the second embodiment.

As shown in FIG. 15A, the single particles are magnetic particles visible as individual particles in the taken bright-field image, and the linked particles are magnetic particles visible as a plurality of touching particles in the taken bright-field image. Pre-dispersion is the state immediately before termination of the application of the magnetic field in step S24, and post-dispersion is the state immediately after waiting for a predetermined time in step S25.

As shown in FIG. 15B, magnetic particles with bound nucleic acid are used as the particles under the first through third conditions. The liquid suspension 53 of the first through third conditions is a phosphate-buffered saline, and the liquid suspension 53 contains the magnetic particles. A surface active agent is not added to the liquid suspension 53 of the first condition, and "Tween20" (registered trademark) reagent is added as a surface active agent to the liquid suspension 53 in the second and third conditions. In the first and second conditions, the surface 11a of the slide member 11, that is, the bottom part 15a, is not cationized, whereas the bottom surface 15a is cationized in the third condition. The processing steps of the second embodiment were conducted under the first through third conditions, and the dispersion rate was determined.

As shown in FIG. 15B, the dispersion rate of the first through third conditions was 0.7%, 15.4%, and 18.5%, respectively. It is understood from the results that dispersion of the magnetic particles on the bottom part 15a accelerated by adding surface active agent to the liquid suspension 53. It also is understood that dispersion of the magnetic particles on the bottom part 15a accelerated by cationizing the bottom part 15a.

As shown in FIGS. 16A and 16B, under the first condition the state of the pre-dispersion and post-dispersion are substantially unchanged. As shown in FIGS. 16C and 16D, under the second condition the post-dispersion number of single particles is several stages greater than the pre-dispersion number of single particles. Accordingly, it is understood from FIGS. 16A through 16D that dispersion of the magnetic particles accelerates when surface active agent is added to the liquid suspension 53.

As shown in FIGS. 16C through 16F, although the pre-dispersion states of the second condition and third condition are substantially the same, the third condition has a higher number of single particles when comparing the post-dispersion states of the second condition and third condition. Accordingly, it is understood from FIGS. 16C through 16F that dispersion of the magnetic particles accelerates when the bottom part 15a is cationized. As shown in FIGS. 16D and 16F, when comparing the post-dispersion states of the second condition and the third condition, the third condition suppressed linking of adjacent magnetic particles. Accordingly, it is understood from FIGS. 16D and 16F that fixing the magnetic particles on the bottom part 15a accelerates and the dispersed state of the magnetic particles on the bottom part 15a is readily maintained by cationizing the bottom part 15a.

Investigation of Surface Active Agent Types

The inventors investigated the types of surface active agents desirable for dispersing magnetic particles on the bottom part 15a by determining dispersion rates after performing the processing steps of the second embodiment using a plurality of types of surface active agents. The dispersion rates used in this investigation are the same as equation (1) above.

As shown in FIG. 17, the left side column shows the reagent name and concentration of the surface active agents used in the investigation. The surface active agents used in the investigation are invariably nonionic surface active agents, the first and second level surface active agents from the top are nonionic ether type, and the third level surface active agents are nonionic ester ether type. Whatever surface active agent was used, the bottom part 15a was subjected to a cationizing process. Magnetic particles with bound nucleic acid was used as the particles. The five types of surface active agent were added to liquid suspension 53, the processing steps of the second embodiment were performed, and the dispersion rates were determined.

The right side column of FIG. 17 shows the dispersion rate calculated for each surface active agent. From the results it is understood that the surface active agents used in the processing steps of the second embodiment are not limited to the above "TritonX100" (trademark) and "Tween20" (trademark), and the same or better dispersion effect can be obtained insofar as the surface active agent is nonionic.

Anionic surface active agents such as SDS, cationic surface active agents such as DDTA, and pH-dependent ampholytic surface active agents also may be used as the surface active agent. That is, the surface active agent added to the liquid suspension 53 is not limited to nonionic surface active agents inasmuch as surface active agents having a high dispersion effect may be selected according to the structure of the bottom part 15a, size of the magnetic particles, and detection target substance bound to the magnetic particles.

Third Embodiment

In the first and second embodiments magnetic particles are linked substantially perpendicularly relative to the bottom part 15a, and thereafter the magnetic particle chain is inclined relative to the bottom part 15a. In the third embodiment, magnetic particles are monolayered on the bottom part 15a and are not linked perpendicularly relative to the bottom part 15a.

Figure 18:
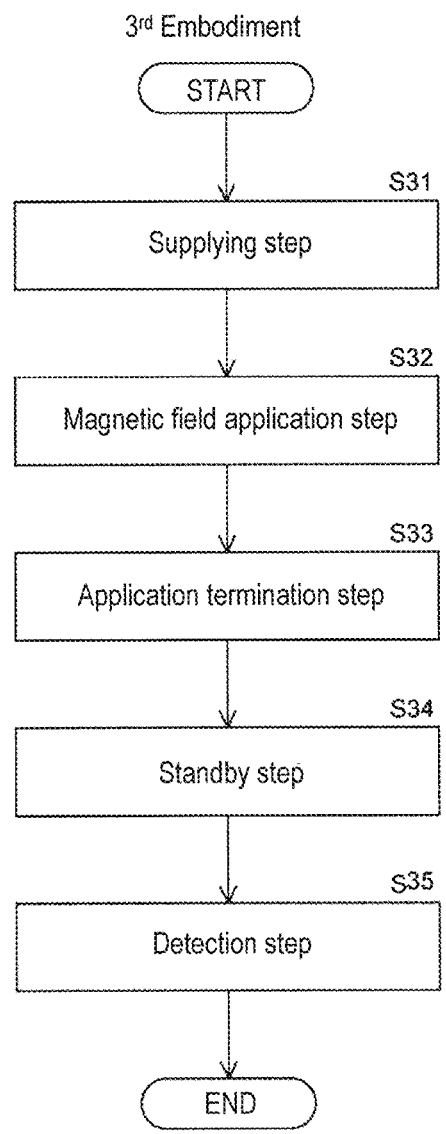
FIG. 18 is a flow chart showing the detection method of a third embodiment.

As shown in FIG. 18, the detection method of the third embodiment includes a supplying step, magnetic field application step, application termination step, standby step, and detection step. The container 10 shown in FIG. 2A also is prepared prior to performing these steps in the third embodiment. The supplying step of step S31, the standby step of step S34, and the detection step of step S35 are identical to the steps of the second embodiment and their description is omitted.

The magnetic field application step of step S32 is a processing step that applies a magnetic field on the liquid suspension 16, and links a plurality of magnetic particles in a row in a direction that intersects the perpendicular direction to the bottom part 15a while drawing the magnetic particles to the bottom part 15a of the container 10 that accommodates the liquid suspension 16 of the magnetic particles with the bound detection target substance.

Figure 19A:
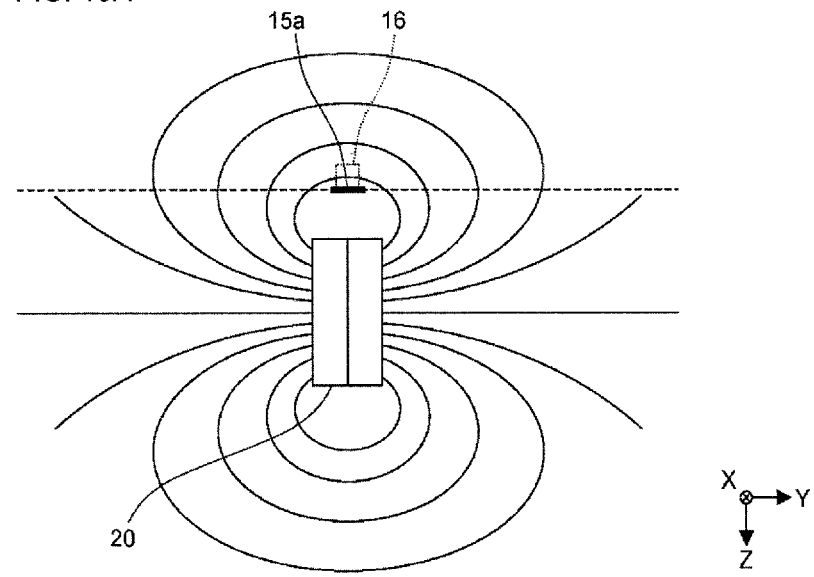
FIG. 19A is a schematic view showing the state of the direction of the magnetic field applied to the liquid suspension by the permanent magnet of the third embodiment is substantially parallel relative to the bottom part.

As shown in FIG. 19A, the magnetic field application step of step S32 positions the magnetic poles of the permanent magnet 20 below the container 10. Specifically, the permanent magnet 20 is positioned directly under the bottom part 15a. This time the permanent magnet 20 is arranged so that the N pole is on the right side and the S pole is on the left side. Note that the permanent magnet 20 also may be arranged so that the N pole is on the left side and the S pole is on the right side.

When the permanent magnet 20 is positioned as shown in FIG. 19A, the lines of magnet force directly above the permanent magnet 20 extend in a horizontal direction. In this way the direction of the magnetic field applied to the liquid suspension 16 is a horizontal direction, and the magnetic particles are linked in a substantially horizontal direction along the magnetic field. The magnetic force gradient in the vertical direction draws the magnetic particles to the bottom part 15a. In the magnetic field application step of step S32, the application of the magnetic field on the liquid suspension 16 is continuous during the time set to establish the chain of linked magnetic particles in the liquid suspension 16 accommodated in the container 10. That is, the permanent magnet 20 continues to be positioned directly below the bottom part 15a only for a predetermined time. In this way the chain of magnetic particles enters a state of approaching the bottom part 15a.

Note that the direction of magnetization of the permanent magnet 20 is not necessarily a horizontal direction insofar as the direction intersects the perpendicular direction relative to the bottom part 15a. In this case, in the magnetic field application step of step S32, a plurality of magnetic particles become linked in a row in a direction intersecting the perpendicular direction relative to the bottom part 15a as the magnetic particles are drawn to the bottom part 15a. Then the magnetic particles approach the bottom part 15a the same as when the magnetization direction is a horizontal direction.

In the magnetic field application step of step S32, the magnetic particles near the bottom part 15a sequentially assume the states shown in FIG. 20A through (f) over time. Referring to FIGS. 20A through 20F, it is understood that the magnetic particles in the liquid suspension 16 gradually link together. After the outlines of the magnetic particles gradually become more distinct, it can be seen that the magnetic particles gradually approach the bottom part 15a. In this way, in the magnetic field application step of step S32, the magnetic particles substantially become monolayered on the bottom part 15a since the magnetic particles approach the bottom part 15a. Accordingly, the detection step also may be performed after the magnetic field application step without performing steps S33 and S34 (described later).

Figure 19B:
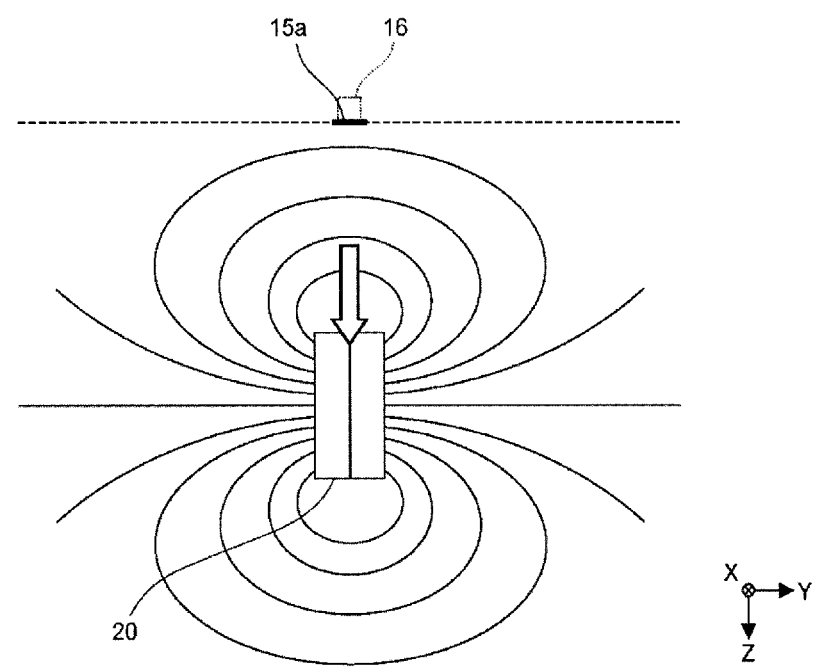
FIG. 19B is a schematic view showing the state in which the magnetic field applied to the liquid suspension by the permanent magnet of the third embodiment can be viewed as [0]
Figure 20A:
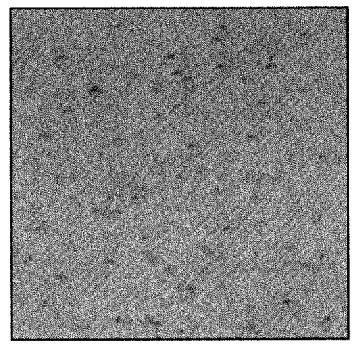
FIGS. 20A through 20F show the bright field images taken from the vertical direction when focus on the liquid suspension is near the bottom part in the magnetic field application step in the third embodiment.
Figure 20B:
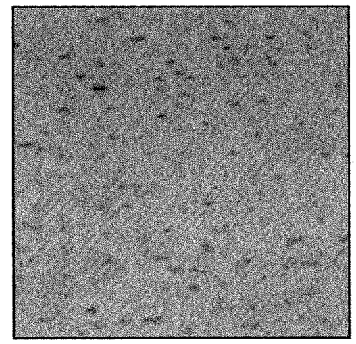
Figure 20C:
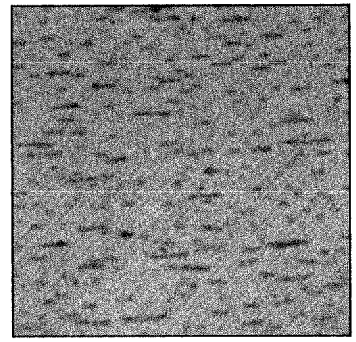
Figure 20D:
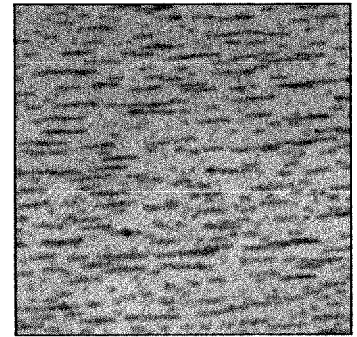
Figure 20E:
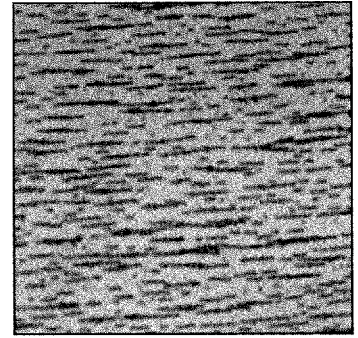
Figure 20F:
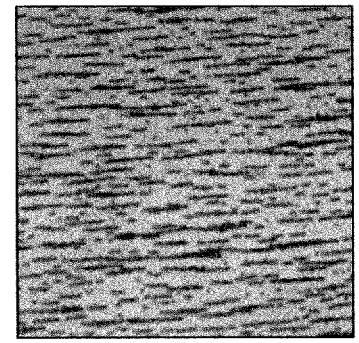

Returning to FIG. 18, the application termination step of step S33 is a processing step to terminate the application of the magnetic field relative to the liquid suspension 16 and is performed between the magnetic field application step and the detection step. Specifically, the magnetic poles of the permanent magnet 20 at the position shown in FIG. 19A are moved downward away from the liquid suspension 16 as shown in FIG. 19B so that the magnetic field applied to the liquid suspension 16 by the permanent magnet 20 can be viewed as [0]. In this way the chain of magnetic particles collapsed due to Brownian motion, and as the magnetic particles at positions distant from the bottom part 15a exhibit random behavior, the magnetic particles approach the bottom part 15a due to gravity.

Returning to FIG. 18, the standby step of step S34 is performed thereafter. In this way substantially all magnetic particles undergoing Brownian motion in the liquid suspension 16 are positioned on the bottom part 15a the same as the second embodiment. Thus, the magnetic particles are monolayered in a dispersed state on the bottom part 15a. The steps of steps S31 through S35 therefore end.

Note that in step S32 it is desirable that the application termination step of step S33 begins before substantially all magnetic particles are positioned on the bottom part 15a. This prevents the chains of magnetic particles from completely grounding on the bottom part 15a. Accordingly, the magnetic particles are more reliably dispersed on the bottom part 15a since the chains of magnetic particles break up in the liquid suspension 16.

In the magnetic field application step the electromagnet 33 shown in FIGS. 21A and 21B also may be used instead of the permanent magnet 20. The electromagnet 33 is provided with a pair of coils 33a and 33a, that are configured the same as the second electromagnet 32 shown in FIGS. 4A and 4B. The electromagnet 33 is configured to be movable in the Z-axis direction.

When the electromagnet 33 is used, the electromagnet 33 is actuated as shown in FIG. 21A in step S32 of FIG. 18. In this way the direction of the magnetic field applied to the liquid suspension 16 is a horizontal direction, and the magnetic particles are linked along the magnetic field. The electromagnet 33 also is moved downward in step S32. In this way a magnetic force gradient is produced in the vertical direction in the liquid suspension 16, and the magnetic particles are drawn to the bottom part 15a. In step S33, the electromagnet 33 is turned off as shown in FIG. 21B. In this way the application of the magnetic field relative to the liquid suspension 16 is stopped, and the magnetic field applied to the liquid suspension 16 becomes [0].

Fourth Embodiment

The fourth embodiment applies the invention to a detection device for detecting a detection target substance bound to magnetic particles based on the detection method of the first embodiment.

Figure 22:
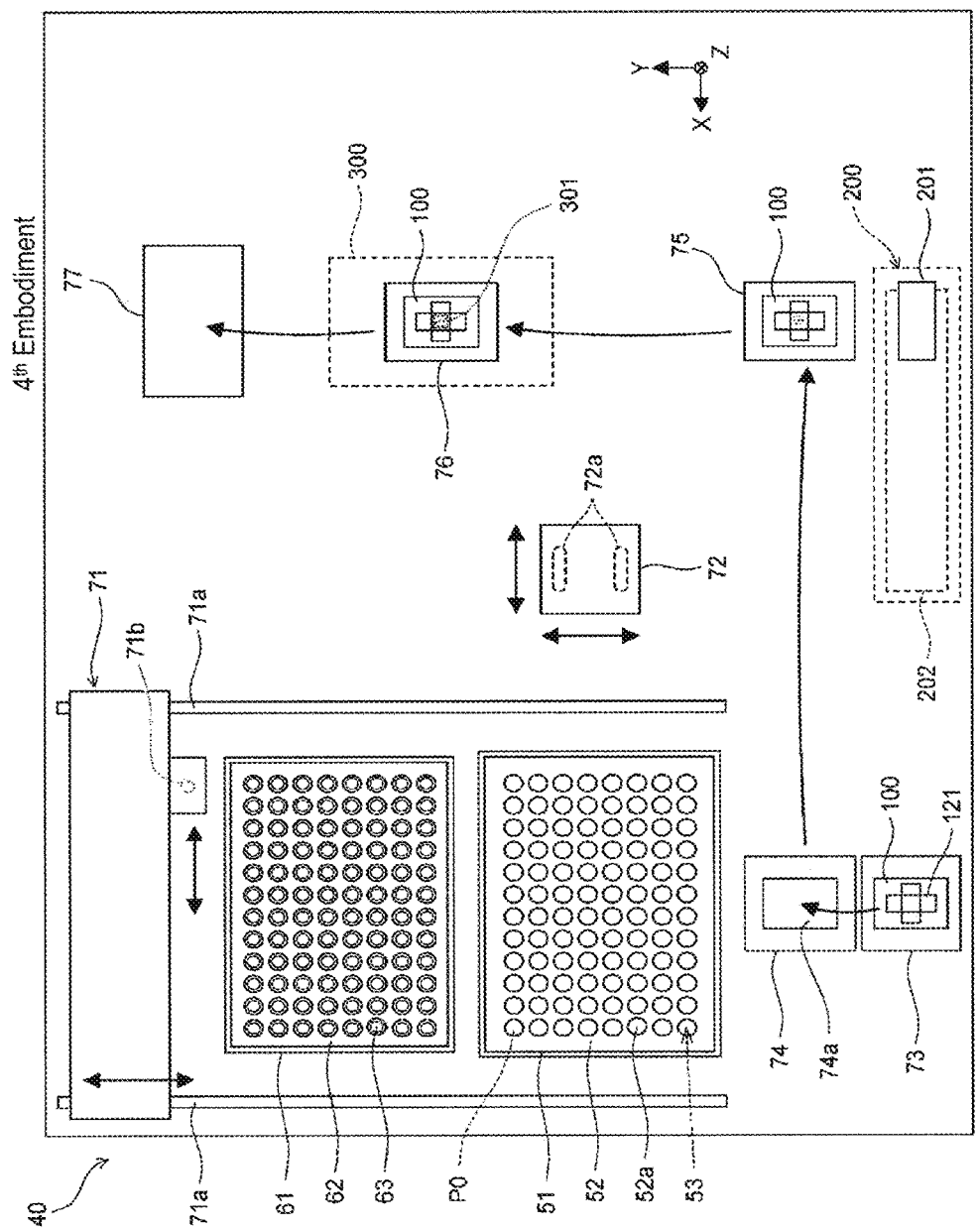
FIG. 22 is a schematic view showing the structure of the interior of the detection device of a fourth embodiment viewed from above.

As shown in FIG. 22, the detection device 40 is provided with a microplate unit 51, dispensing tip container unit 61, dispenser 71, container transport unit 72, container storage 73, container install units 74 and 75, container disposal unit 77, magnetic field supplying unit 200, and image obtaining unit 300. In FIG. 22 the X-axis positive direction is the leftward direction, and the Y-axis positive direction is the backward direction.

A microplate 52 is arranged on the microplate unit 51. A total of 96 individual wells 52a are provided in 8 front-to-back rows of 12 in the left-to-right direction on the surface of the microplate 52. The wells 52a accommodate the liquid suspension 53 prepared in preprocessing. The liquid suspension 53 is identical to the suspension 16 of the first embodiment. Dispensing tip containers 62 are arranged on the dispensing tip container unit 61. A total of 96 dispensing tips 63 are loaded in 8 front-to-back rows of 12 in the left-to-right direction in the dispensing tip containers 62. An opening for inserting a nozzle 71b is formed at the top end of the dispensing tip 63, and a hole for aspirating and discharging is formed at the bottom end of the dispensing tip 63.

The dispenser 71 has two nozzles 71a, nozzle 71b, and a drive device not shown in the drawings, and suctions and discharges the liquid suspension 53. The dispenser 71 is configured to be movable in the front-to-back direction along rails 71a. The nozzle 71b is supported by the dispenser 71, and configured to be movable in the vertical direction. The nozzle 71b is positioned directly above the dispensing tip 63 within the dispensing tip container 62, and the dispensing tip 63 is installed on the nozzle 71b when moved downward. The nozzle 71b with the installed dispensing tip 63 is positioned directly above the well 52a of the microplate 52, and suctions the liquid suspension 53 in the well 52a through the dispensing tip 63 when moved downward. The container storage 73 stores a plurality of containers 10 in a stacked state in the vertical direction.

Figure 23A:
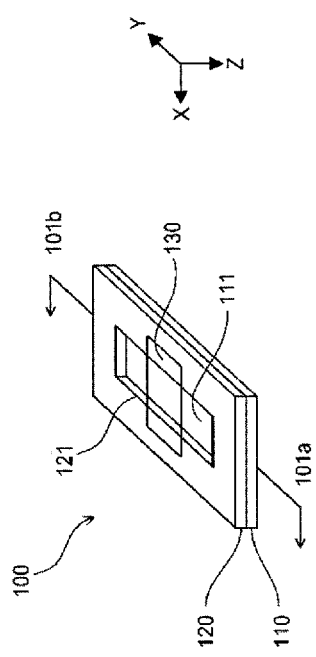
FIG. 23A is a schematic view showing the structure of a container of the fourth embodiment.

As shown in FIG. 23A, the container 100 has a first member 110, second member 120, and cover 130. The first member 110 is a transparent plate-like glass. The container 100 corresponds to the container 10 of the first embodiment. The first member 110 also may be made of a material other than glass, such as resin and the like. The top surface 111 of the first member 110 is a cationic flat surface. The surface 111 has a positive surface charge imparted by a cationizing process. The second member 120 is a plate-like glass substantially the same size as the first member 110. The second member 120 also may be made of a material other than glass, such as resin and the like. An opening 121 is formed in the center of the second member 120. The opening 121 vertically passes through the second member 120. The second member 120 is set on the surface 111 of the first member 110.

The cover 130 is a thin transparent glass. The cover 130 also may be made of a material other than glass, such as resin and the like. The length in the front-to-back direction of the cover 130 is shorter than the length in the front-to-back direction of the opening 121. The length in the left-to-right direction of the cover 130 is longer than the length in the left-to-right direction of the opening 121. The cover 130 is fixed to the surface of the second member 120 so as to straddle the opening 121. Each part of the container 100 is made of a material that can be regarded as non-magnetic so as to not interfere with the magnetic field of the permanent magnet 201 (described later).

Figure 23B:
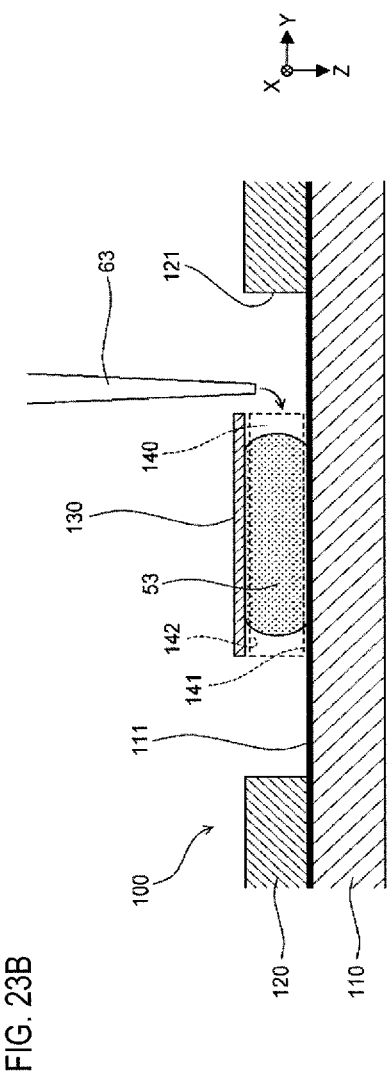
FIG. 23B is a schematic view showing the side surface of the container of the fourth embodiment.

When the cross section 101a-101b shown in FIG. 23A is viewed in the X-axis positive direction, the cross section is as shown in FIG. 23B. As shown in FIG. 23B, a housing part 140 is formed as an empty space circumscribed by the surface 111 of the first member 110, opening 121 of the second member 120, and cover 130. The bottom part 141 of the housing part 140 is part of the top surface 111, and the top part 142 of the housing part 140 is part of the bottom surface of the cover 130. The bottom part 141 and the top part 142 are surfaces perpendicular to the depth direction of the container 100.

In the container 100, the bottom part 141 also need not be a flat surface the same as the container 10 of the first embodiment. For example, the bottom part 141 also may be a curved surface or uneven surface. When imaging by the image obtaining unit 300, magnetic particles monolayered on the bottom part 141 may be imaged.

Returning to FIG. 22, the container transport unit 72 includes two suction pads 72a, and a drive device not shown in the drawing. The container transport unit 72 is configured to be movable front-to back and left-to-right within the detection device 40. The container transport unit 72 holds and lifts the container 100 by attaching to the top surface of the second member 120 of the container 100 via the two suction pads 72a. The container install unit 74 includes a concavity 74a for seating the container 100. The container transport unit 72 sets the container 100 stored in the container storage 73 in the concavity 74a of the container install unit 74.

There also may be two or more container transport units 72 within the detection device 40 to improve the processing speed of the detection device 40. The container 100 also may be moved within the detection device 40 by means other than the container transport unit 72.

When the container 100 is placed in the container install unit 74, the nozzle 71b is positioned directly above the opening 121 of the container 100. Then the nozzle 71b is lowered and the liquid suspension 53 suctioned through the dispensing tip 63 is discharged into the opening 121. As shown in FIG. 23B, when the liquid suspension 53 is discharged from the end of the dispensing tip 63, the liquid suspension 53 is drawn into the housing part 140 via capillarity and is accommodated within the housing part 140. When the discharge of liquid suspension 53 is completed, the nozzle 71b is moved backward and the dispensing tip 63 mounted on the nozzle 71b is dropped into a disposal unit (not shown in the drawing) for disposal.

When the liquid suspension 53 is supplied to the container 100 of the container install unit 74, the container transport unit 72 moves the container 100 of the container install unit 74 and places the container 100 in the container install unit 75. The container install unit 75 is inside the detection device 40. The magnetic field supplying unit 200 is set near the container install unit 75, and is provided with a permanent magnet 201 and moving device 202. The magnetic field supplying unit 200 moves the permanent magnet 201 via the moving device 202, and the permanent magnet 201 applies a magnetic field to the container 100 set in the container install unit 75. In this way a magnetic field is applied to the liquid suspension 53 accommodated in the container 100. The magnetic field supplying unit 200 also may drive an electromagnet instead of the permanent magnet 201 and apply a magnetic field on the liquid suspension 53 accommodated in the container 100.

Figure 24A:
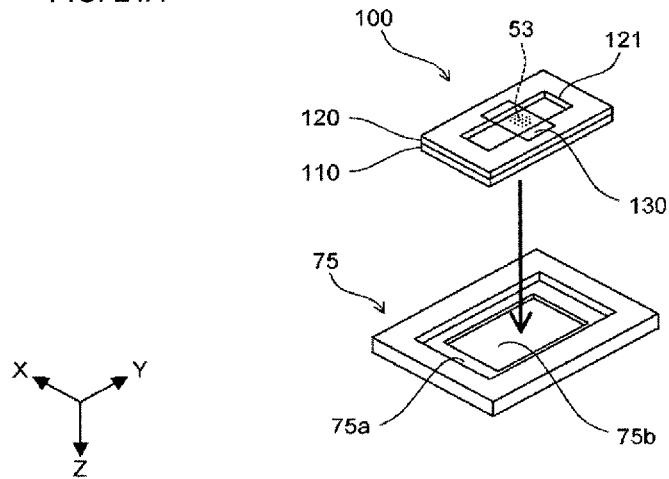
FIG. 24A shows the container installed in a container installation part in the fourth embodiment.

The container install unit 75 includes a concavity 75a for seating the container 100, as shown in FIG. 24A. In the horizontal plane, the external form of the concavity 75a is somewhat larger than the external form of the container 100. An opening 75b vertically passing through the concavity 75a is formed in the bottom surface of the concavity 75. In the horizontal plane, the external form of the opening 75b is somewhat smaller than the external form of the concavity 75a. When the container 100 is set in the concavity 75a, the bottom surface of the container 100, that is, the bottom surface of the first member 110, is open in a downward direction through the opening 75b. When the bottom surface of the container 100 is open in this way, the container install unit 75 does not interfere with the magnetic field applied by the permanent magnet 201 from the bottom side.

Figure 24B:
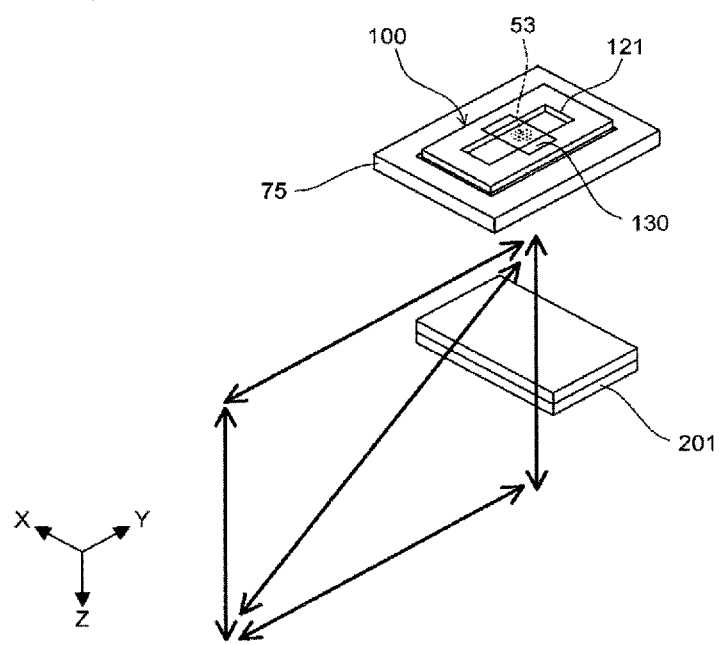
FIG. 24B shows the movement of the permanent magnet in the fourth embodiment.

As shown in FIG. 24B, the permanent magnet 201 of the magnetic field supplying unit 200 applies a magnetic field from the bottom side relative to the container 100 placed in the container install unit 75. In the horizontal plane, the permanent magnet 201 is configured to be wider than the width range of the liquid suspension 53 at the bottom part 141 of the container 100. The size of the external form of the permanent magnet 201 in the horizontal plane is configured so that the direction of the magnetic field in the width range of the liquid suspension 53 is the upward direction when the permanent magnet 201 is positioned directly below the container 100. The permanent magnet 201, for example, is movable parallel to the YZ plane when the top surface is parallel to the horizontal plane as indicated by the thick arrows in FIG. 24B. The magnetic field applied to the liquid suspension 53 of the container 100 is changed in this way.

The permanent magnet 201 also may be installed in the detection device 40, and the container install unit 75 moved by the moving device 202 of the magnetic field supplying unit 200. In this case also the magnetic particles can be monolayered if the relative positional relationship between the container 100 and the permanent magnet 201 is changed the same as the first embodiment.

Figure 25:
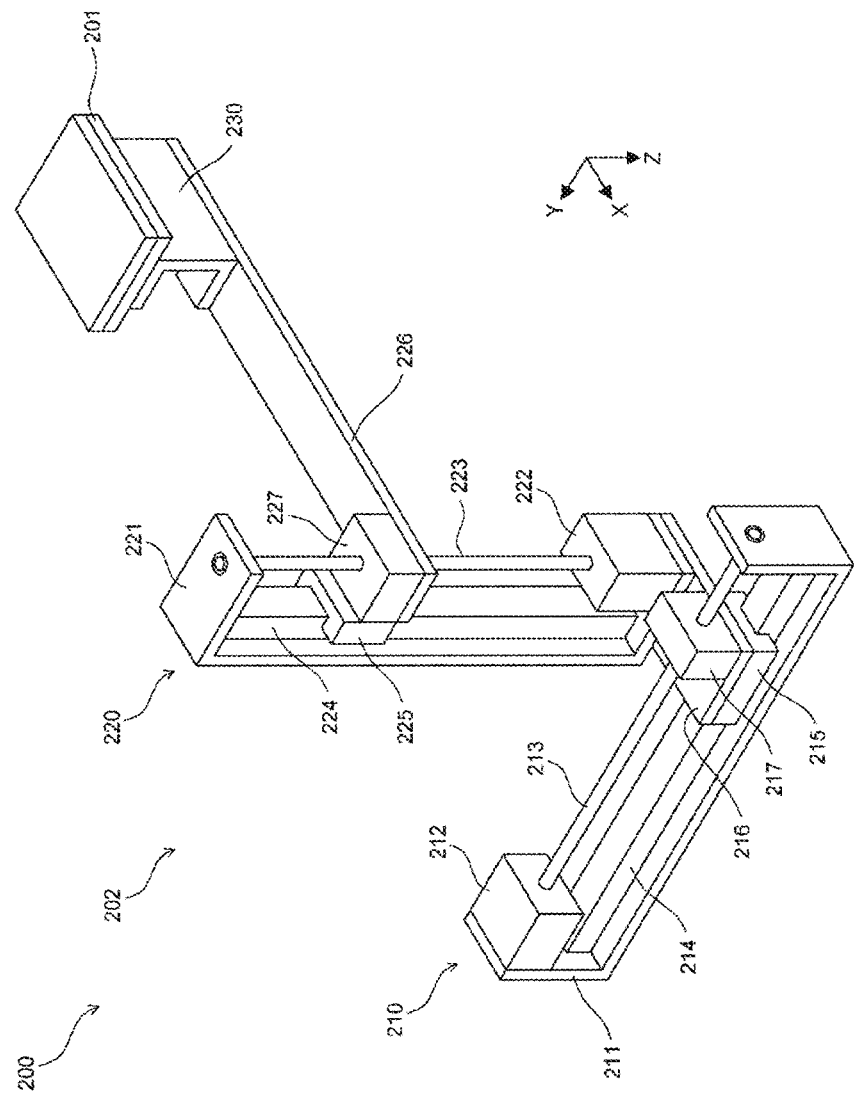
FIG. 25 shows the structure of the magnetic field supplying part of the fourth embodiment.

As shown in FIG. 25, the moving device 202 includes a forward-and-back transporter 210, vertical transporter 220, and magnet support 230. The forward-and-back transporter 210 has a base member 211, step motor 212, shaft 213, rail 214, oscillator 215, forward-and-back moving member 216, and ball bearing 217. The vertical transporter 220 has a base member 221, step motor 222, shaft 223, rail 224, oscillator 225, vertical moving member 226, and ball bearing 227.

The base member 211 is installed in the detection device 40. The step motor 212 is installed on the base member 211. One end of the shaft 213 is mounted on the rotating shaft of the step motor 212, the other end of the shaft 213 is supported by the base member 211 so as to be rotatable. The rail 214 extends in the Y-axis direction, and is mounted on the base member 211. The oscillator 215 is supported on the rail 214 and is movable in the Y-axis direction. The forward-and-back moving member 216 is mounted on the oscillator 215. The ball bearing 217 is mounted on the top surface of the forward-and-back moving member 216.

A screw groove is formed on the outer surface of the shaft 213. The shaft 213 is mounted by a ball bearing 217 installed on the oscillator 215. When the shaft 213 is rotated by the step motor 212, the drive force is transferred through the ball bearing 217 to the forward-and-back moving member 216. In this way the forward-and-back moving member 216 moves in the Y-axis direction, that is, forward and back, along the rail 214.

The base member 221 is mounted on the forward-and-back moving member 216. Since each part of the vertical transporter 220 is configured the same as each part of the forward-and-back transporter 21, a detailed description is omitted. When the shaft 223 is rotated by the step motor 222, the vertical moving member 226 moves in the Z-axis direction, that is, the vertical direction, along the rail 224. The magnet support 230 is mounted to the top surface of the vertical moving member 226 extending in the X-axis direction. The permanent magnet 201 is mounted on the magnet support 230 so that the magnetization direction is the vertical direction.

When the magnetic field supplying unit 200 is configured this way, the permanent magnet 201 is freely movable in the forward and back direction and vertical direction with the top surface of the magnet 201 parallel to the horizontal plane according to the actuations of the step motors 212 and 222.

Returning to FIG. 22, when the monolayering process by the magnetic field supplying unit 200 ends, the container transport unit 72 moves the container 100 of the container install unit 75 to the container install unit 76. The container install unit 76 is configured the same as the container install unit 75. That is, the container install unit 76 includes a concavity 76a identical to the concavity 75a of the container install unit 75, and an opening 76b identical to the opening 75b of the container install unit 75.

The image obtaining unit 300 images the imaging area 301. Specifically when the housing part 140 of the container 100 is positioned at the imaging area 301, the image obtaining unit 300 images the liquid suspension 53 within the housing part 140 positioned at the imaging area 301 in a state of focus near the bottom part 141.

Figure 26:
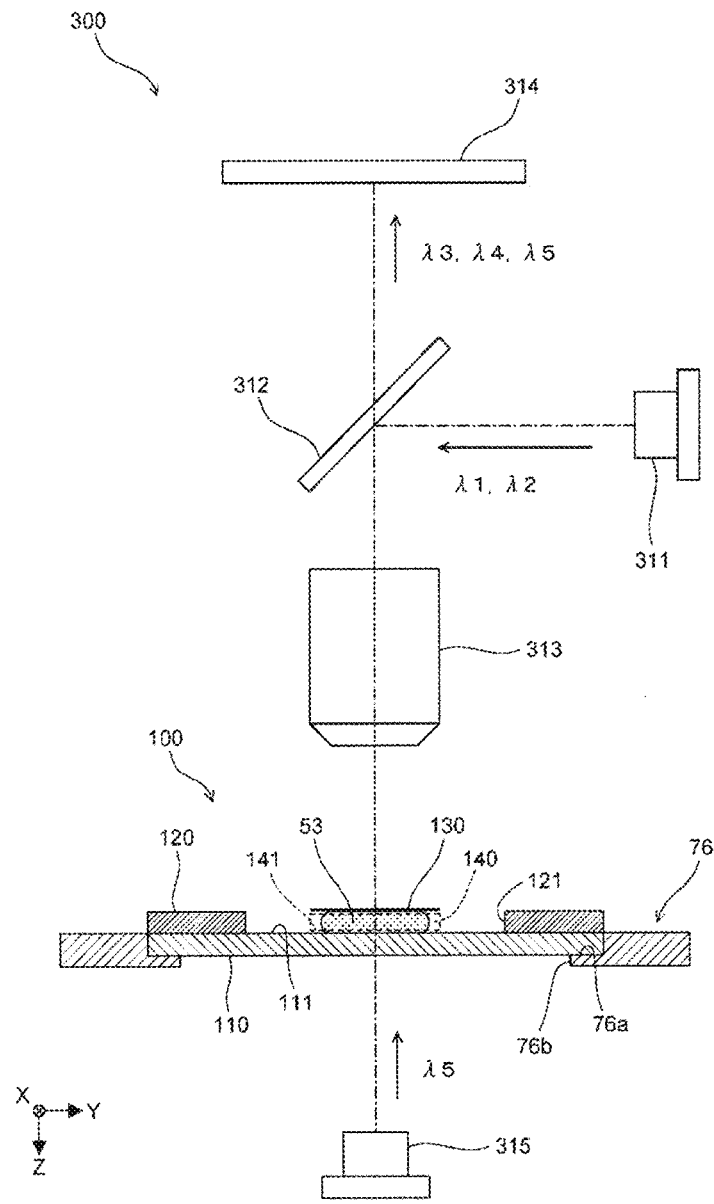
FIG. 26 shows the structure of the image obtaining part of the fourth embodiment.

As shown in FIG. 26, the image obtaining unit 300 includes a light source 311, dichroic mirror 312, objective lens 313, light receiving part 314, and light source 315. The cross sections of the container 100, container install unit 76, and liquid suspension 53 are shown together in FIG. 26.

The light source 311 irradiates light from above onto the liquid suspension 53 accommodated in the container 100. The light source 311 is, for example, an LED, and the light emitted from the light source 311 is light of wavelength $\lambda 1$ and light of wavelength $\lambda 2$. Wavelength $\lambda 1$ is a wavelength of light that causes the fluorescent dye bound to a mutant DNA molecule to give off fluorescent light, and wavelength $\lambda 2$ is a wavelength of light that causes the fluorescent dye bound to a wild-type DNA molecule to give off fluorescent light. The light source 311 is controlled to emit either the light of wavelength $\lambda 1$ or light of wavelength $\lambda 2$.

The dichroic mirror 312 reflects the light of wavelengths $\lambda 1$ and $\lambda 2$ emitted from the light source 311, and transmits light of wavelengths $\lambda 3$, $\lambda 4$, and $\lambda 5$ (described later). The objective lens 313 collects the light of wavelengths $\lambda 1$ and $\lambda 2$ reflected by the dichroic mirror 312. The light of wavelengths $\lambda 1$ and $\lambda 2$ collected by the objective lens 313 irradiates the liquid suspension 53 positioned at the imaging area 301. Fluorescent light of wavelength $\lambda 3$ is given off when the light of wavelength $\lambda 1$ irradiates the fluorescent dye bound to the mutant DNA molecules, and fluorescent light of wavelength $\lambda 4$ is given off when the light of wavelength $\lambda 2$ irradiates the fluorescent dye bound to the wild-type DNA molecules.

The fluorescent light of wavelengths $\lambda 3$ and $\lambda 4$ are collected by the objective lens 313, and transmitted to the dichroic mirror 312. The light receiving part 314 receives the fluorescent light given off from the liquid suspension 53 above the container 100. The light receiving part 314 is a camera provided with a CMOS image sensor. The light receiving part 314 receives the fluorescent light of wavelengths $\lambda 3$ and $\lambda 4$ transmitted through the dichroic mirror 312, and outputs the fluorescent light image information as imaging signals.

The light source 315 irradiates light from below relative to the liquid suspension 53 accommodated in the container 100. The light source 315 is, for example, an LED, and the light emitted from the light source 315 is light of wavelength $\lambda 5$. The wavelength $\lambda 5$ is a wavelength of light for obtaining a bright-field image of the magnetic particles. The light of wavelength $\lambda 5$ emitted from the light source 315 irradiates from the bottom side relative to the liquid suspension 53 positioned at the imaging area 301. The light of wavelength $\lambda 5$ transmitted through the liquid suspension 53 is collected by the objective lens 313, and transmitted through the dichroic mirror 312. The light receiving part 314 receives the light of wavelength $\lambda 5$ transmitted through the dichroic mirror 312, and outputs the bright-field image information of the magnetic particles as imaging signals.

The image obtaining unit 300 also may be configured to irradiate light of wavelengths $\lambda 1$, $\lambda 2$, $\lambda 5$ simultaneously on the liquid suspension 53, separate the fluorescent light of wavelengths $\lambda 3$ and $\lambda 4$ given off from the liquid suspension 53, and the fluorescent light of wavelength $\lambda 5$ transmitted through the liquid suspension 53, and receive the light by respectively different light receiving parts. In this case the image information of fluorescent light of wavelengths $\lambda 3$ and $\lambda 4$, and the bright-field image information of the magnetic particles can be obtained simultaneously.

Returning to FIG. 22, When the imaging of the liquid suspension 53 accommodated in the container 100 ends, the container transport unit 72 moves the container 100 to the container transport unit 76, and discards the container 100 in the container disposal unit 77. As described above, the liquid suspension 53 accommodated in one well 52a of the microplate 52 is accommodated in one container 100, and imaged by the image obtaining unit 300 after monolayering by the magnetic field supplying unit 200. When imaging is performed by the image obtaining unit 300, an extraction analysis process (described later) is performed. When the extraction analysis processes of all liquid suspension 53 accommodated on the microplate 52 are completed, the processing by the detection device 40 ends.

Figure 27:
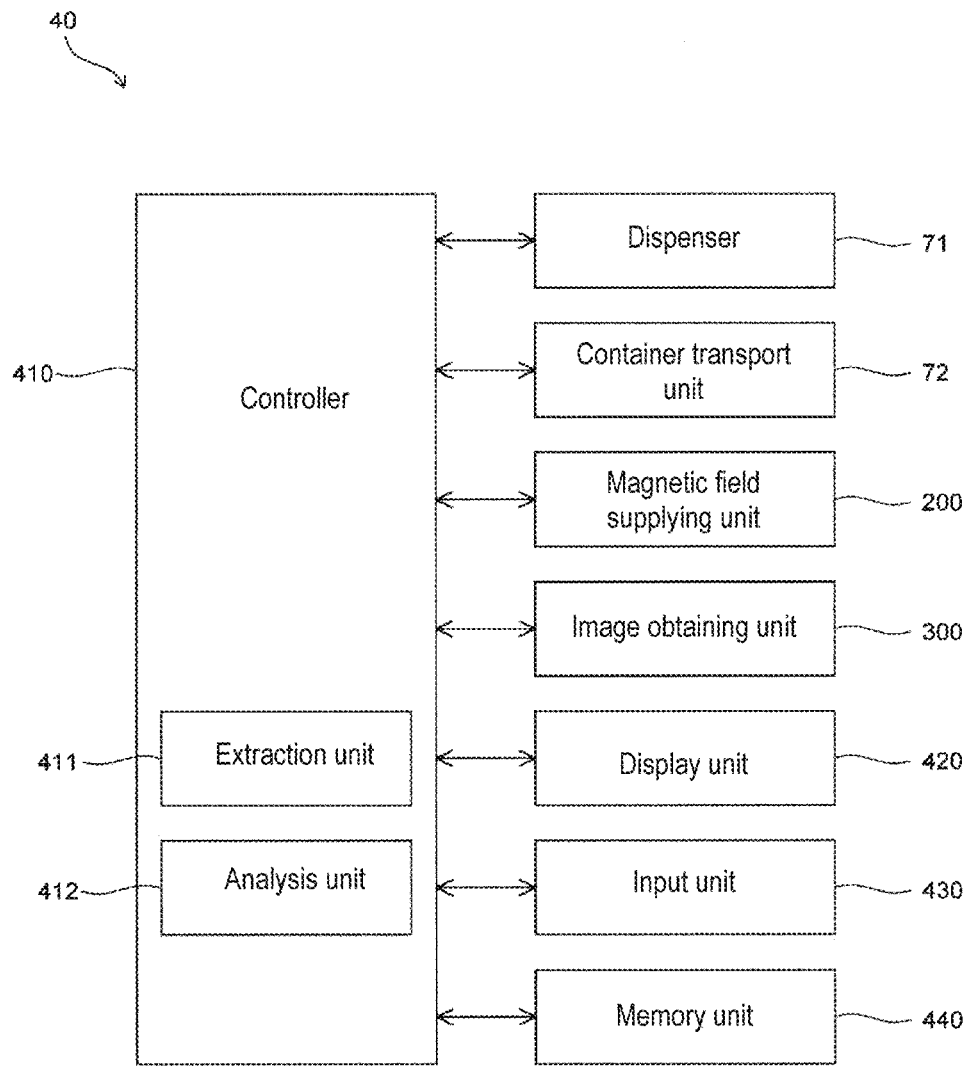
FIG. 27 is a block diagram showing the structure of the detection device of the fourth embodiment.

As shown in FIG. 27, the detection device 40 includes a dispenser 71, container transport unit 72, magnetic field supplying unit 200, image obtaining unit 300, controller 410, display unit 420, input unit 430, and memory unit 440. The controller 410, for example, may be configured by a CPU. The controller 410 receives the signals from each part of the detection device 40, and controls each part. The memory unit 440 is configured by RAM, ROM, hard disk or the like. The display unit 420 is configured by a display. The input unit 430 is configured by buttons arranged on the front of the housing of the detection unit 40. The input unit 430 also may be configured by a mouse and keyboard. The controller 410 performs the functions of an extraction unit 411 and analysis unit 412 by programs stored in the memory unit 440.

The processes performed by the detection device 40 are described below.

The processes performed by the detection device 40 include the dispensing process, monolayering process, imaging process, extraction analysis process, and display process. The operator arranges the microplate 52 containing liquid suspension 53 on the microplate unit 51, and inputs the start instruction through the input unit 430. In this way the dispensing process, monolayering process, imaging process, extraction analysis process, and display process are started, and these processes are executed in parallel. These processes are executed by the controller 410 driving each part in the detection device 40.

Figure 28:
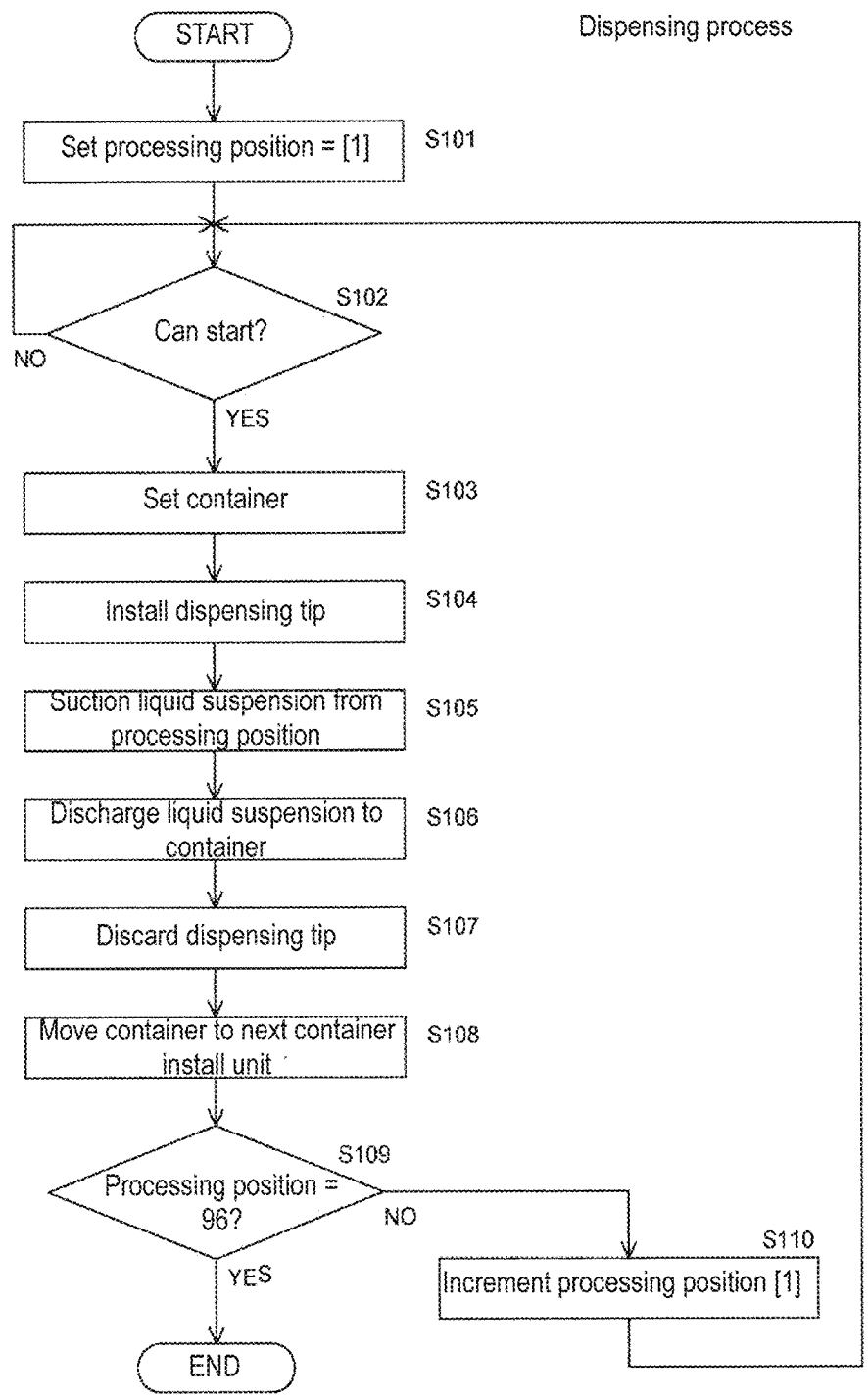
FIG. 28 is a flow chart showing the dispensing process in the fourth embodiment.

The dispensing process is described below referring to FIG. 28.

In step S101, the controller 410 sets the processing position at the initial position P0 at the back left end of the microplate 52 by setting the processing position at [1]. The processing position is set at the leftmost position of one front row and moves sequentially one well at a time to the right until the processing position reaches the right end by incrementing one in step S110 (described later). The value of the processing position is stored in memory unit 440.

In step S102, the controller 410 determines whether the process of step 103 or subsequent step can start. Specifically, the controller 410 determines that step S103 3 or subsequent step can start when a container 100 is not placed in the container install unit 75. The controller 410 also determines that the process of step S103 or subsequent steps can start when it can be assumed that a container 100 of the container install unit 75 is moved to the container install unit 76 if the time required for processes of steps S103 through S107 has elapsed even when a container 100 is placed in the container install unit 75. The container 410 determines that the processes of steps S103 and subsequent steps cannot start when it cannot be assumed a container 100 is placed in the container install unit 75 even though the time required for the processing of steps S103 through S107 has elapsed.

When dispensing can start, the controller 410 places a container 100 of the container storage 73 in the container install unit 74 in step S103. In step S104, the controller 410 installs the dispensing tip 63 on the nozzle 71b. In step S105, the controller 410 auctions liquid suspension 53 from the processing position of the microplate 52. In step S106, the controller 410 discharges the suctioned liquid suspension 53 into the container 100. In this way the liquid suspension 53 is accommodated in the housing part 140 of the container 100. In step S107, the controller 410 discards the dispensing tip 63 installed on the nozzle 71b to the disposal unit. In step S108, the controller 410 transports the container 100 of the container install unit 74 to the container install unit 75.

In step S109, the controller 410 determines whether the processing position is 96. When the processing position is not 96, there are unprocessed positions remaining on the microplate 52. In this case, the controller 410 increments the processing position [1] in step S110, and the process returns to step S102. When the processing position is 96, the dispensing process shown in FIG. 28 ends because processing has been completed for all positions of the microplate 52.

The monolayering process is described below referring to FIG. 29.

In step S201, the controller 410 determines whether monolayering can start. Specifically, the controller 410 determines that monolayering can start when a container 100 is installed in the container install unit 75, and determines that monolayering cannot start when a container 100 is not installed in the container install unit 75.

Figure 30:
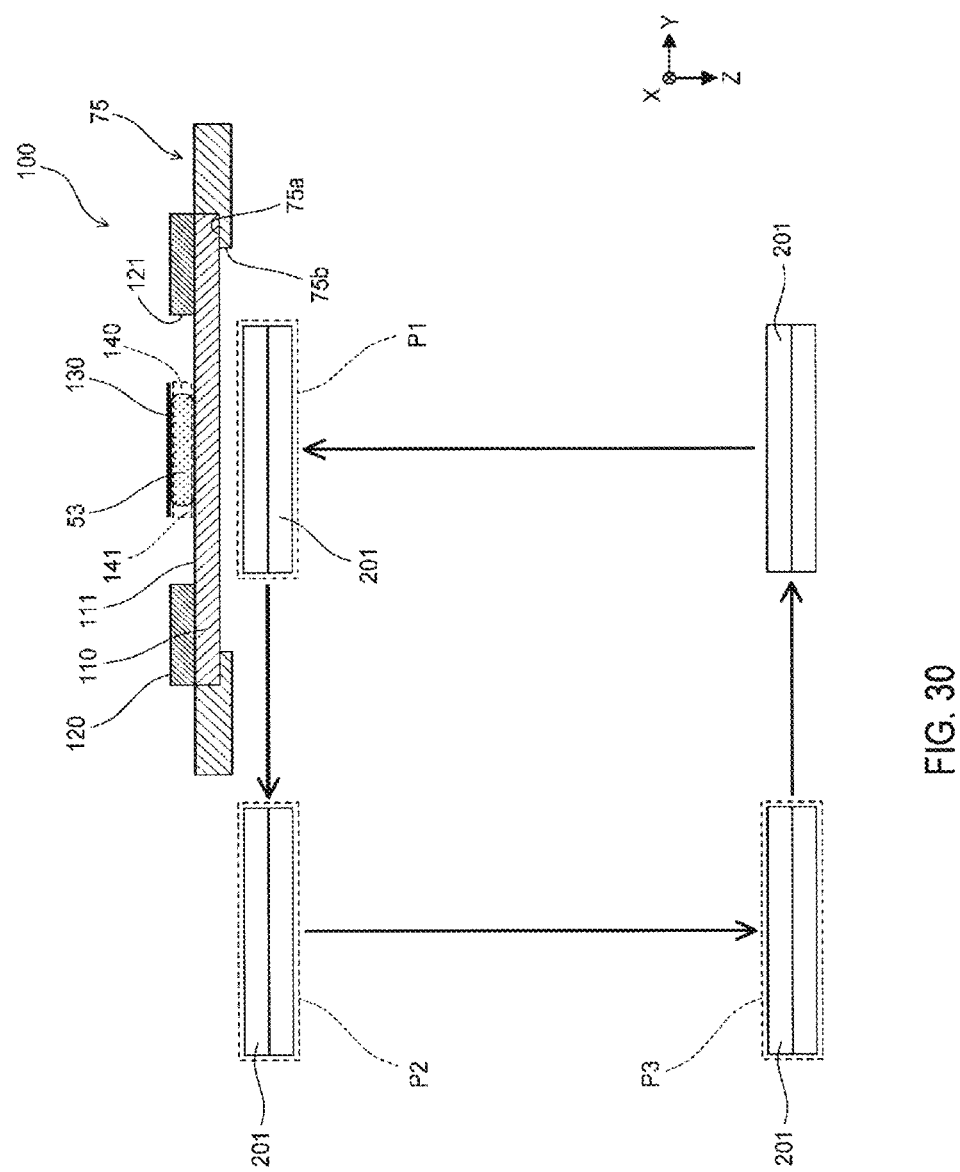
FIG. 30 shows the movement of the permanent magnet in the fourth embodiment.

When monolayering can start, the controller 410 transports the permanent magnet 201 at position P3 to position P1 in step S202. As shown in FIG. 30, the position P3 is a position separated from the container install unit 76 in the Y-axis direction and Z-axis direction to the extent that the magnetic field applied to the liquid suspension 53 by the permanent magnet 201 can be regarded as [0]. That is, position P3 is a position at which the application of the magnetic field on the liquid suspension 53 stops. Position P1 is a position beneath the container install unit 75, and is a position directly under the container 100 installed in the container install unit 75. After the permanent magnet 201 at position P3 is moved in the Y-axis positive direction, the permanent magnet 201 is positioned at position P1 by being moved in the Z-axis negative direction. When the permanent magnet 201 is positioned at position P1, the permanent magnet 201 is positioned directly below the bottom part 141 of the housing part 140 the same as the case shown in FIG. 3A. In this way a magnetic field is applied in a substantially directly upward direction relative to the liquid suspension 53 accommodated in the container 100.

In step S203, the controller 410 continues positioning the permanent magnet 201 at position P1 to await processing for a predetermined time. In this way a plurality of magnetic particles are chained in a row from the bottom part 141 of the container 100 the same as the first embodiment.

In step S204, the controller 410 moves the permanent magnet 201 at position P1 in the Y-axis negative direction toward position P2. As shown in FIG. 30, position P2 is a position a predetermined distance away from position P1 in the Y-axis negative direction relative to the liquid suspension 53 accommodated in the container 100. When positioned at position P2, the permanent magnet 201 is positioned the same as the case shown in FIG. 3B viewed in the X-axis direction. In this way a magnetic field is applied in a substantially horizontal direction relative to the liquid suspension 53 accommodated in the container 100. Accordingly, the chain of magnetic particles lay on the bottom part 141, and magnetic particles are monolayered on the bottom part 141 the same as the first embodiment.

In step S205, the controller 410 moves the permanent magnet 201 from position P2 to position P3. Position P3 is a position further away from position P2 relative to the liquid suspension 53 accommodated in the container 100. In this way the application of the magnetic field is terminated relative to the liquid suspension 53. Thus, the linked magnetic particles approach the bottom part 141 the same as the first embodiment.

In step S206, the controller 410 determines whether the container 100 of the container install unit 75 can be transported to the container install unit 76. Specifically, the controller 410 determines the container 100 cannot be transported when the container 100 is installed in the container install unit 76, and determines container 100 can be transported when the container 100 is not installed in the container install unit 76. When the container 100 can be transported, the controller 410 transports the container 100 of the container install unit 75 to the container install unit 76 in step S207.

In step S208, the controller 410 determines whether monolayering is completed for all containers 100. That is, the controller 410 determines whether the processes of steps S201 through S207 have been completed relative to the 96 individual containers 100 based on the 96 individual wells 52a of the microplate 52. When monolayering has not been completed for all containers 100, the controller 410 returns the process to step S201. When monolayering has been completed for all containers 100, the monolayering process shown in FIG. 29 ends.

The first electromagnet 31 and second electromagnet 32 shown in FIGS. 4A and 4B also may be used instead of the permanent magnet 201 and moving device 202. In this case the magnetic pole surface of the first electromagnet 31 and second electromagnet 32 is wider than the spread range of the liquid suspension 53 at the bottom part 141. Specifically, in the first electromagnet 31 and second electromagnet 32, the width of the magnetic pole surface in the X-axis direction is configured to be larger than the width of the container 100 in the X-axis direction, and the width of the magnetic pole surface in the Y-axis direction is configured to be larger than the width at last of the bottom part 141 in the Y-axis direction. The monolayering process in this case is changed as shown in FIG. 31.

Figure 29:
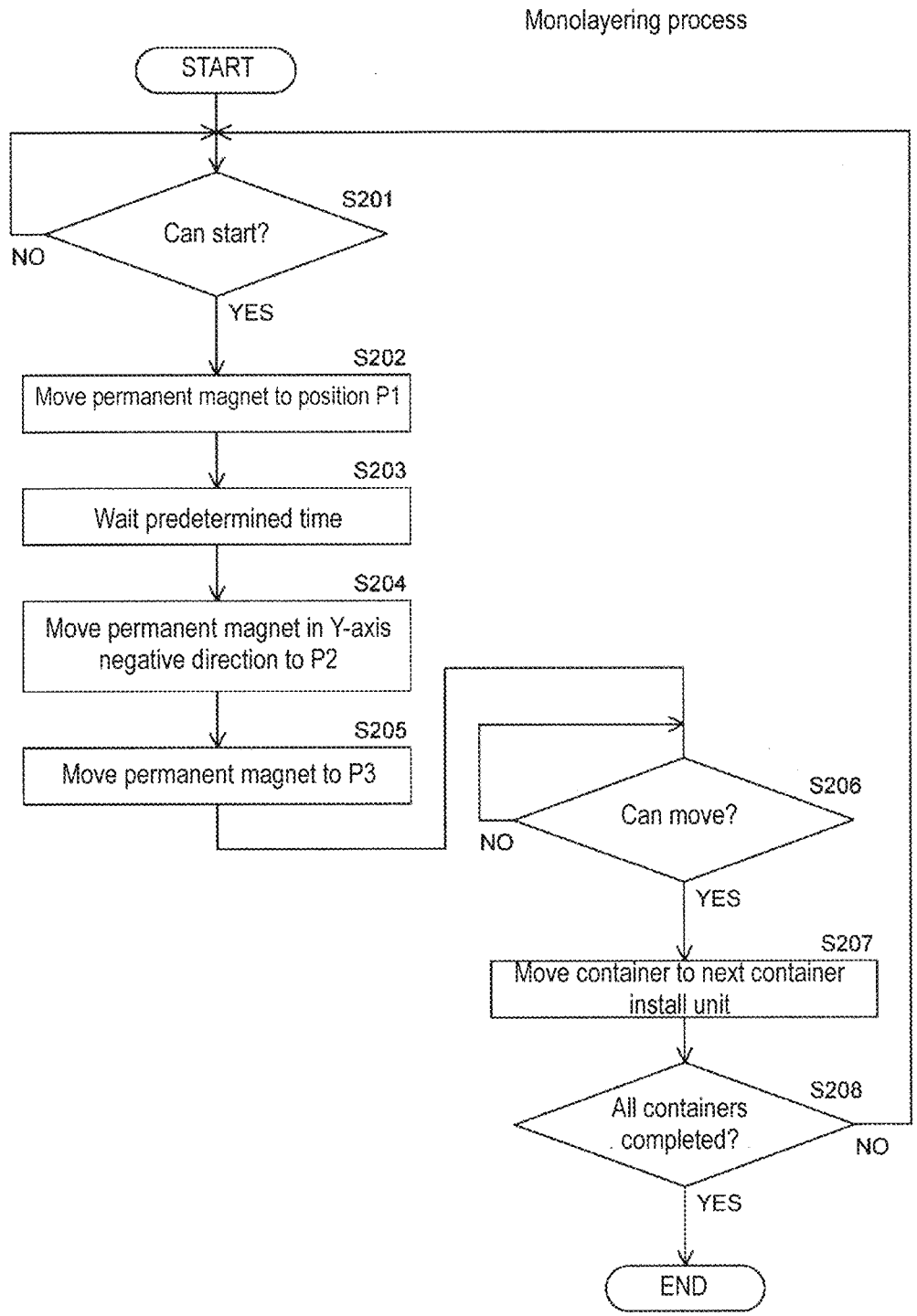
FIG. 29 is a flow chart showing the monolayering process in the fourth embodiment.
Figure 31:
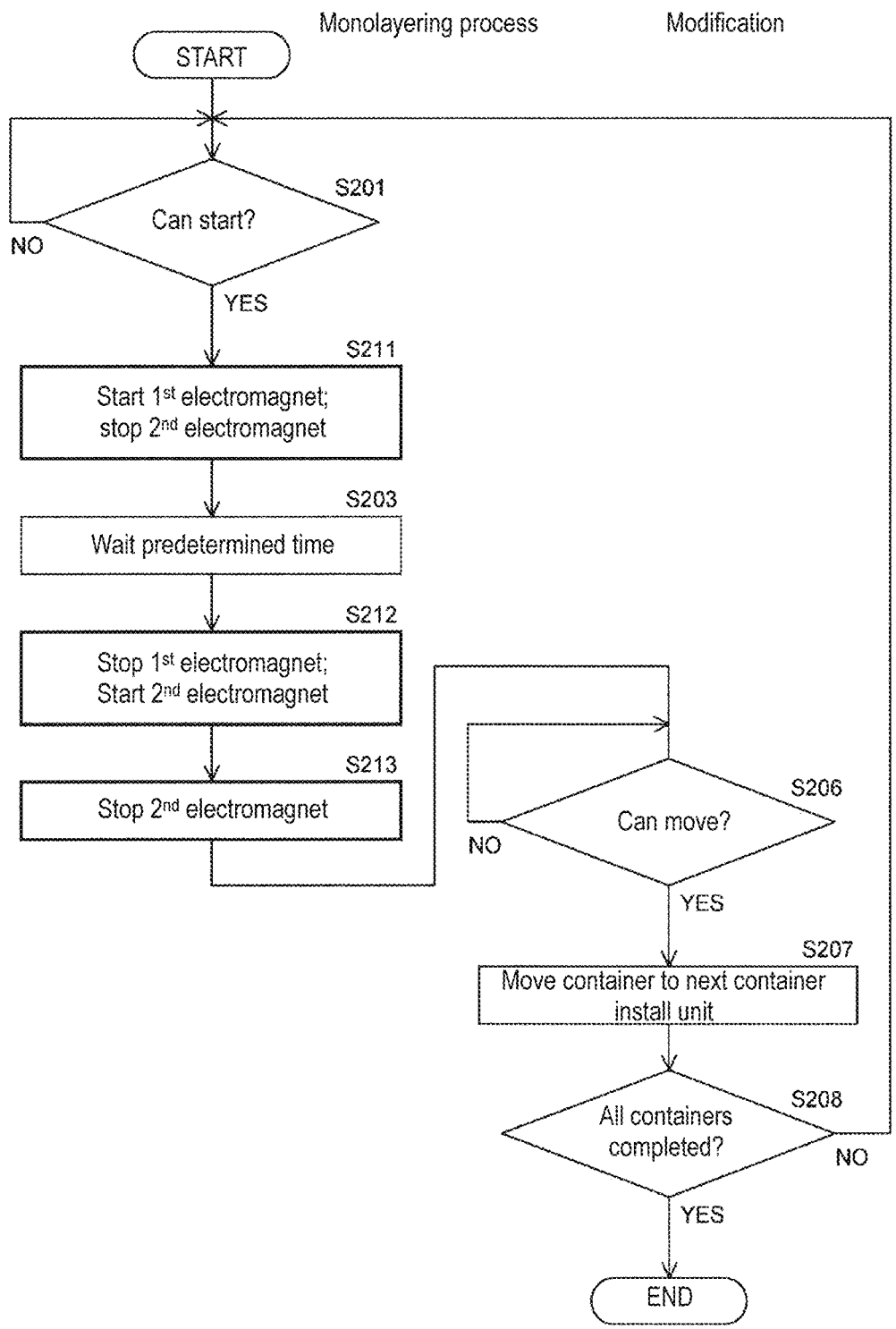
FIG. 31 is a flow chart showing the monolayering process in a modification of the fourth embodiment.

The monolayering process shown in FIG. 31 respectively adds steps S211, S212, and S213 in place of steps S202, S204, and S205 compared to FIG. 29. In step S211, the controller 410 actuates the first electromagnet 31, and stops the second electromagnet 32. In this way a magnetic field is applied substantially in a directly upward direction relative to the liquid suspension 53 the same as step S202 in the same state as FIG. 4A. In step S212, the controller 410 stops the first electromagnet 31, and actuates the second electromagnet 32. In this way a magnetic field is applied substantially in a horizontal direction relative to the liquid suspension 53 the same as step S204 in the same state as FIG. 4B. In step S213, the controller 410 stops the second electromagnet 32. In this way the application of the magnetic field relative to the liquid suspension 53 is terminated the same as step S205.

The second electromagnet 32 also may be omitted by providing a rotation device to rotate the first electromagnet 31 around the X-axis. In this case, when the first electromagnet 31 is rotated by the rotation device to a position similar to the second electromagnet 32, a magnetic field can be applied in a substantially horizontal direction relative to the liquid suspension 53 the same as when using the second electromagnet 32.

Note that since the magnetic field applied by an electromagnet is smaller than the magnetic field applied by a permanent magnet, the electromagnet generally is larger in order to achieve the same level as the permanent magnet. Accordingly, it is preferable to use the permanent magnet 20 as the means of generating a magnetic field in order to make the magnetic field supplying unit 200 more compact.

The imaging process is described below referring to FIG. 32.

In step S301, the controller 410 determines whether imaging can start. Specifically, the controller 410 determines the container 100 that imaging can start when the container 100 is installed in the container install unit 76, and determines imaging cannot start when the container 100 is not installed in the container install unit 76.

When imaging can start, the controller 410 controls the image obtaining unit 300 to image the liquid suspension 53 positioned in the imaging area 301 in step S302. Specifically, the controller 410 controls the light source 311 to emit light of wavelength λ1, and the light receiving part 314 images the fluorescent light of wavelength λ3. Then the controller 410 controls the light source 311 to emit light of wavelength λ2, and the light receiving part 314 images the fluorescent light of wavelength λ4. The controller 410 then controls the light source 311 to emit light of wavelength λ5, and the light receiving part 314 images the fluorescent light of wavelength λ5. In step S303, the controller 410 discards the container 100 of the container install unit 76.

In step S304, the controller 410 determines whether imaging is completed for all containers 100. That is, the controller 410 determines whether the processes of steps S301 through S303 have been completed relative to the 96 individual containers 100 based on the 96 individual wells 52a of the microplate 52. When imaging has not been completed for all containers 100, the controller 410 returns the process to step S301. When imaging has been completed for all containers 100, the imaging process shown in FIG. 32 ends.

The extraction analysis process is described below referring to FIG. 33A.

Figure 32:
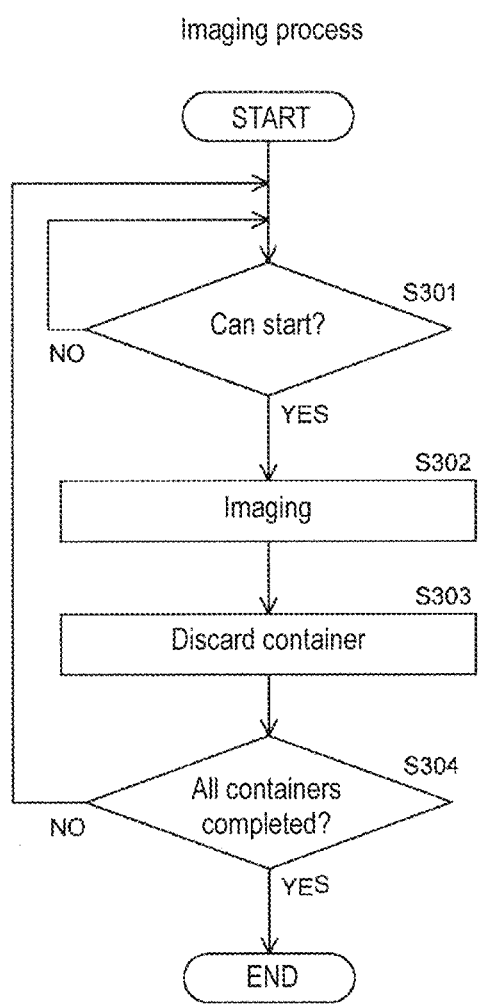
FIG. 32 is a flow chart showing the imaging process in the fourth embodiment.

In step S401, the controller 410 determines whether imaging was performed in step S302 of FIG. 32. When imaging was performed, the controller 410 generates an image based on the imaging signals output from the light receiving part 314 in step S402. Specifically, the controller 410 respectively generates a fluorescent image corresponding to the mutant DNA molecules, and a fluorescent image corresponding to the wild-type DNA molecules, from the imaging signals based on the fluorescent light of wavelengths λ3 and λ4. The controller 410 also generates a bright-field image of the imaging area 301 from imaging signals based on the light of wavelength λ5. Note that step S402 may be omitted when the images are generated by the image obtaining unit 300.

In step S403, the extraction unit 411 of the controller 410 performs the extraction process using the fluorescent image generated in step S402. Specifically, the extraction unit 411 specifies the bright spot areas in the fluorescent image based on the fluorescent light of wavelength λ3. The extraction unit 411 detects the mutant DNA molecules by extracting the magnetic particles to which the mutant DNA molecules are bound based on the specified bright spot area. The extraction unit 411 also specifies the bright spot areas in the fluorescent image based on the fluorescent light of wavelength λ4. The extraction unit 411 detects the wild-type DNA molecules by extracting the magnetic particles to which the wild-type DNA molecules are bound based on the specified bright spot area.

In step S403, the extraction unit 411 also may perform extraction by data processing based on imaging signals output from the light receiving part 314, and detect the mutant DNA molecules and wild-type DNA molecules without using the image generated in step S402.

In step S404, the analysis unit 412 of the controller 410 performs the analysis process based on the detection results of step S403. Specifically, the analysis unit 412 counts the number of magnetic particles to which mutant DNA molecules are bound based on the detection results of the mutant DNA molecules, and counts the number of magnetic particles to which wild-type DNA molecules are bound based on the detection results of the wild-type DNA molecules. The analysis unit 12 calculates the percentage of mutant DNA molecules based on the number of magnetic particles to which mutant DNA molecules are bound and the number of magnetic particles to which wild-type DNA molecules are bound. When the number of magnetic particles with bound mutant DNA molecules is designated N1, and the number of magnetic particles with bound wild-type DNA molecules is designated N2, the percentage of mutant DNA molecules can be calculated by N1/N2 or N1/(N1+N2).

In step S405, the controller 410 stores the image generated in step S402 and the analysis results obtained in step S404 in the memory unit 440. In step S406, the controller 410 determines whether extraction and analysis is completed for all liquid suspensions 53. That is, the controller 410 determines whether the process of steps S401 through S405 have been completed for all liquid suspension 53 on the microplate 52. When extraction and analysis has been completed for all liquid suspensions 53, the extraction analysis process shown in FIG. 33A ends.

When the dispensing process, monolayering process, imaging process, and extraction analysis process are performed in this way, the operator can obtains images and analysis results for all liquid suspensions 53 accommodated on the microplate 52 just by placing the microplate 52 and inputting the start instruction. The burden on the operator is thus reduced, and detection and analysis is efficiently performed for the liquid suspensions 53 made in the preprocess.

The display process is described below referring to FIG. 33B.

In step S501, the controller 410 determines whether the operator has input a display instruction through the input unit 430. When a display instruction has been input, the controller 410 reads the image and analysis results stored in step S405 of FIG. 33A from the memory unit 440 and display the image and results in step S502. In step S502, the image and analysis results also may be sent to another device connected to, and able to communicate with, the detection device 40. When the process of step S502 ends, the controller 410 returns the process to step S501.

Fifth Embodiment

The fifth embodiment applies the invention to a detection device for detecting a detection target substance bound to magnetic particles based on the detection method of the second embodiment. The structure of the fifth embodiment is the same as the fourth embodiment, and controls of the fifth embodiment are the same as the fourth embodiment excluding the monolayering process. Only the monolayering process of the fifth embodiment is described below.

Figure 34:
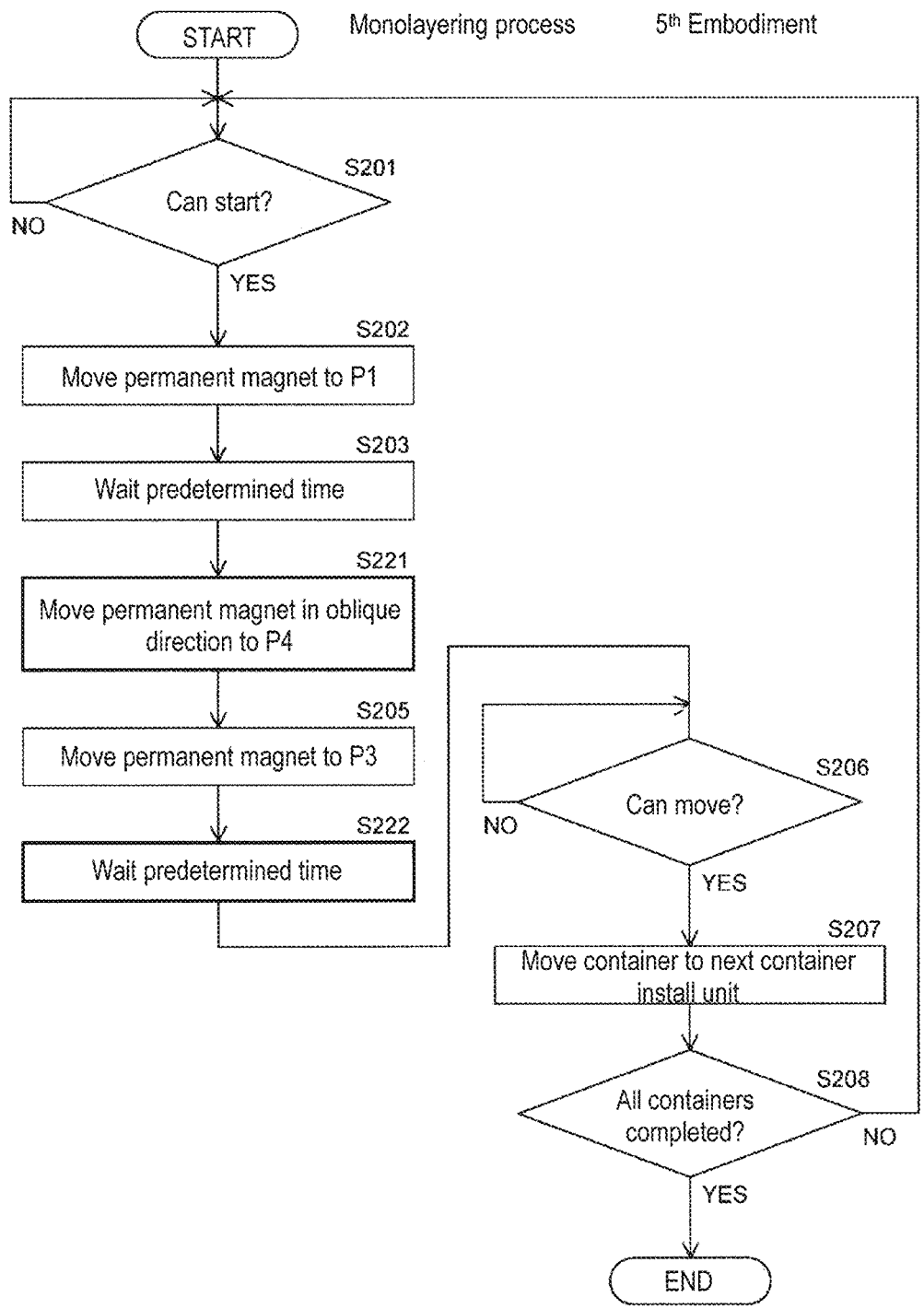
FIG. 34 is a flow chart showing the monolayering process in a fifth embodiment.

As shown in FIG. 34, the monolayering process of the fifth embodiment adds step S221 in place of step S204, and adds step S222 immediately following step S205. The process from step S221 to step S222 is described below.

Figure 35:
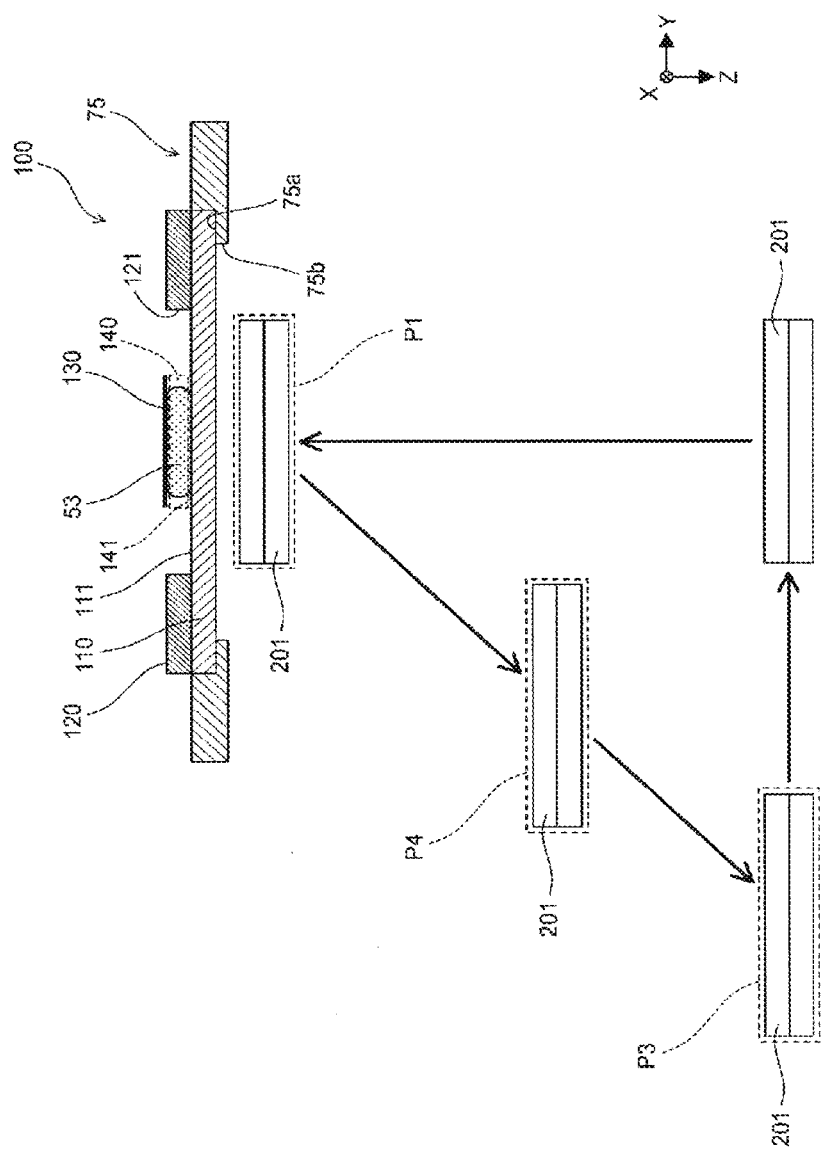
FIG. 35 shows the movement of the permanent magnet in the fifth embodiment.

In step S221, the controller 410 moves the permanent magnet 201 from position P1 in an oblique downward direction toward position P4. As shown in FIG. 35, position P4 is a position a predetermined distance away from position P1 in an oblique downward direction relative to the liquid suspension 53 accommodated in the container 100. When positioned at position P4, the permanent magnet 201 is positioned the same as the case shown in FIG. 9A viewed in the X-axis direction. In this way a magnetic field is applied in an oblique direction from the vertical direction relative to liquid suspension 53 accommodated in the container 100. Accordingly, the chain of magnetic particles is extended in an oblique direction from the bottom part 141 approaching the bottom part 141.

In step S205, the controller 410 moves the permanent magnet 201 from position P4 to position P3, as shown in FIG. 35. In step S222, the controller 410 waits a predetermined time to disperse the magnetic particles in the liquid suspension 53 to the bottom part 141 of the container 100. In this way substantially all the magnetic particles undergoing Brownian motion in the liquid suspension 53 are positioned at the bottom part 141, so as to form a monolayer in which the magnetic particles are dispersed on the bottom part 141.

In the fifth embodiment, after a predetermined time has elapsed from stopping the application of the magnetic field relative to the liquid suspension 53, the container 100 is moved to the image obtaining unit 300, and imaging is performed by the image obtaining unit 300. Accordingly, the target DNA molecules bound to the magnetic particles can be accurately detected even when a high percentage of magnetic particles are bound with target DNA molecules since imaging is performed when the magnetic particles are in a dispersed state on the bottom part 141.

The first electromagnet 31 and second electromagnet 32 shown in FIGS. 10A and 10B also may be used instead of the permanent magnet 201 and moving device 202. In this case the width the first electromagnet 31 and second electromagnet 32 are configured so that the width in the left-to-right direction is wider than the width in the left-to-right direction of the container 100. The monolayering process in this case is changed as shown in FIG. 36.

Figure 36:
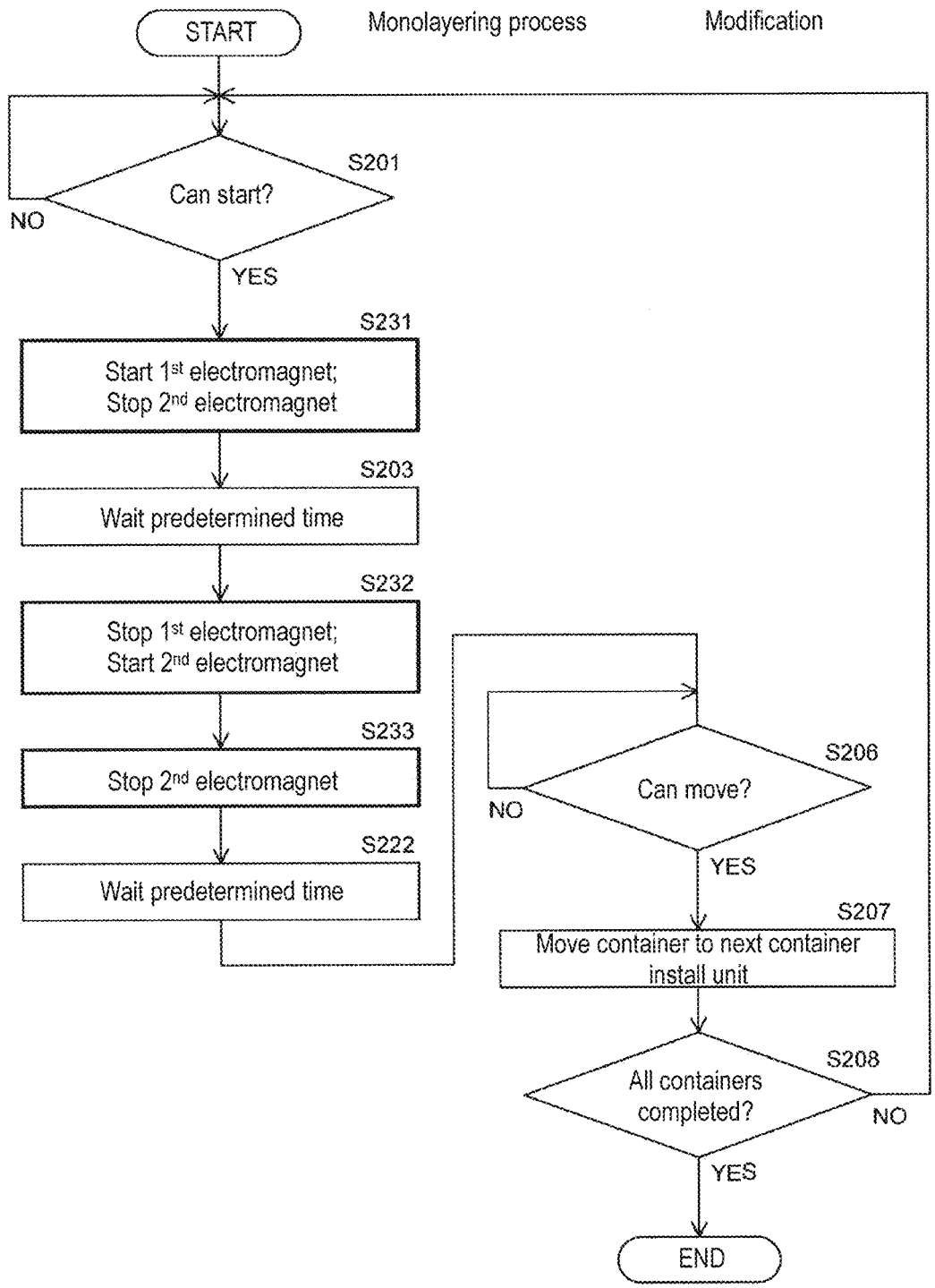
FIG. 36 is a flow chart showing the monolayering process in a modification of the fifth embodiment.

The monolayering process shown in FIG. 36 respectively adds steps S231, S232, and S233 in place of steps S202, S221, and S205 compared to FIG. 34. In step S231, the controller 410 actuates the first electromagnet 31, and stops the second electromagnet 32. In this way a magnetic field is applied substantially in a directly upward direction relative to the liquid suspension 53 the same as step S202 in the same state as FIG. 10A. In step S232, the controller 410 stops the first electromagnet 31, and actuates the second electromagnet 32. In this way a magnetic field is applied substantially in an oblique direction relative to the liquid suspension 53 the same as step S224 in the same state as FIG. 10B. In step S233, the controller 410 stops the second electromagnet 32. In this way the application of the magnetic field relative to the liquid suspension 53 is terminated the same as step S205.

Sixth Embodiment

The sixth embodiment applies the invention to a detection device for detecting a detection target substance bound to magnetic particles based on the detection method of the third embodiment. The structure of the sixth embodiment is the same as the fifth embodiment excepting that the magnetization direction of the permanent magnet 201 is the horizontal direction. Controls of the sixth embodiment are identical to the fifth embodiment excluding the monolayering process. Only the monolayering process of the sixth embodiment is described below.

Figure 37:
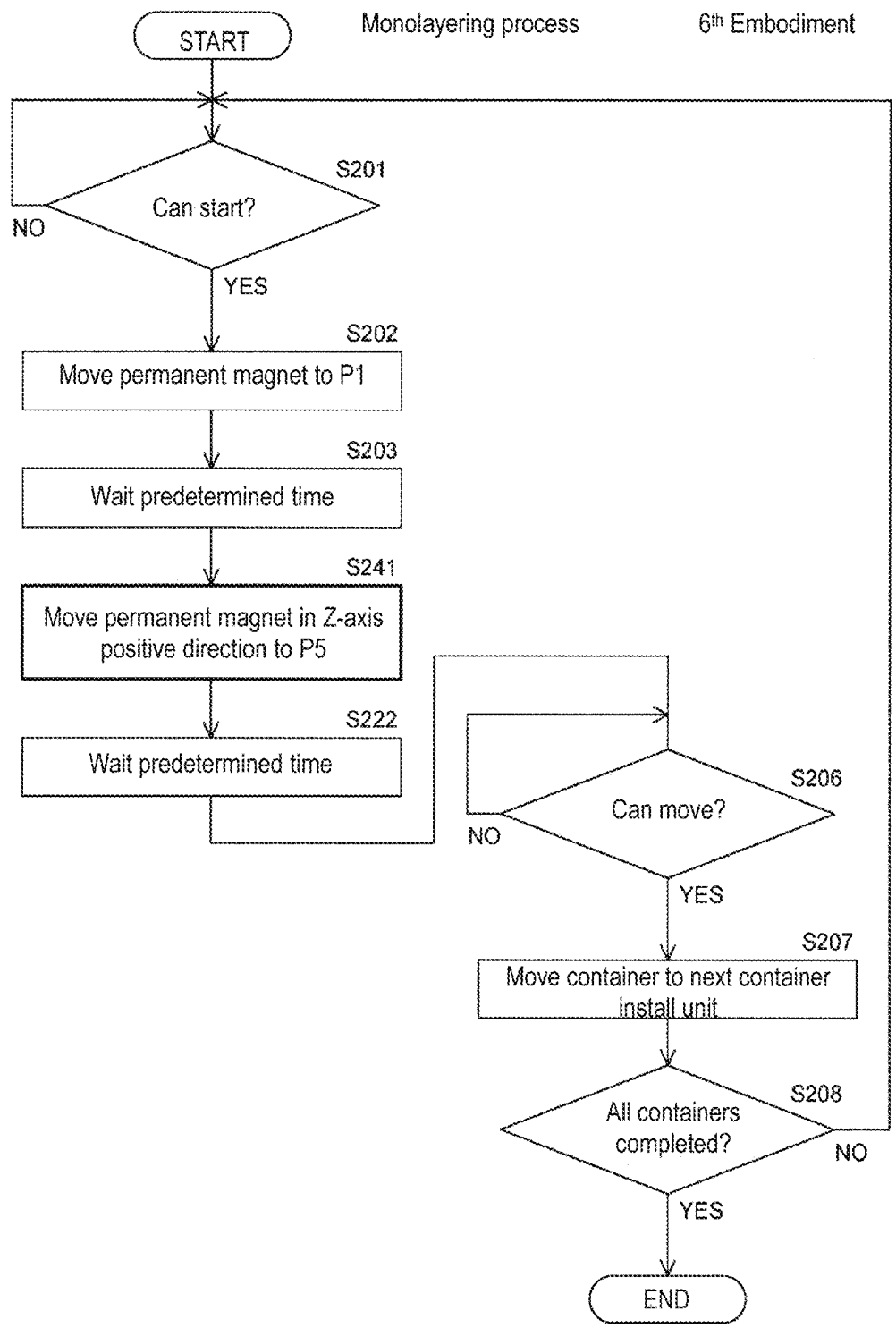
FIG. 37 is a flow chart showing the monolayering process in a sixth embodiment.

As shown in FIG. 37, the monolayering process of the sixth embodiment adds step S241 in place of step S221, and omits step S205 compared to FIG. 34. The process from step S202 to step S222 is described below.

Figure 38:
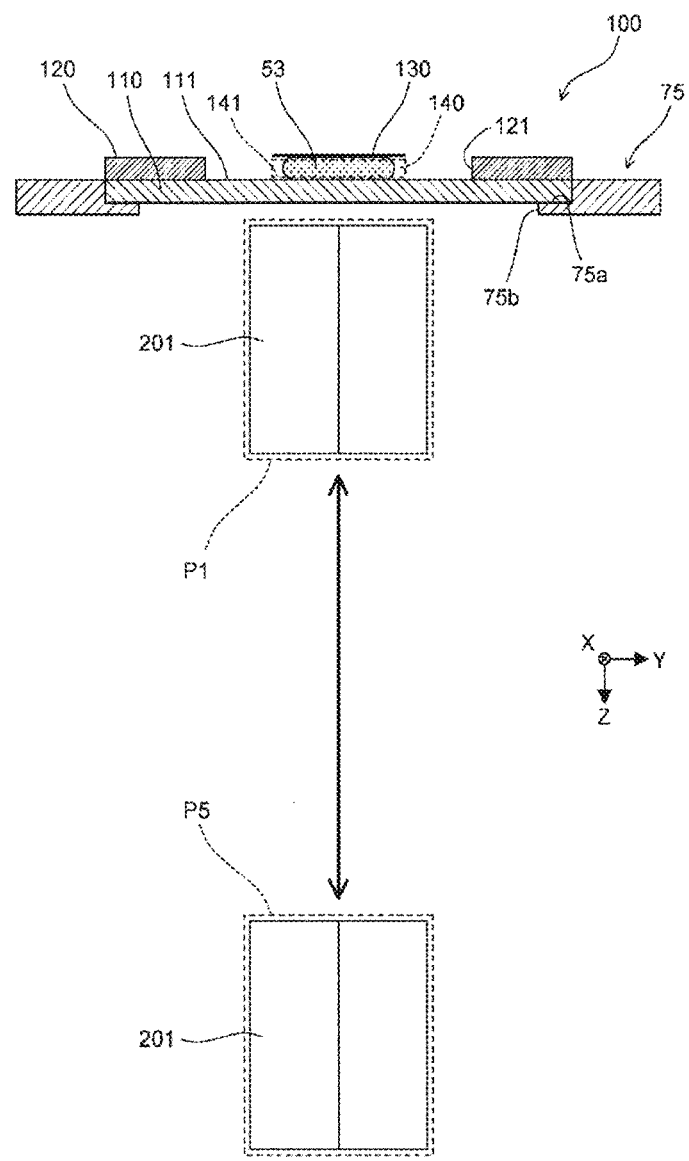
FIG. 38 shows the movement of the permanent magnet in the sixth embodiment.

In step S202, the controller 410 moves the permanent magnet 201 from position P5 to position P1. As shown in FIG. 38, the permanent magnet 201 of the sixth embodiment is installed above the magnet support 230 so that the magnetization direction is the horizontal direction. Position P5 is a position separated from the container install unit 76 in the Z-axis direction to the extent that the magnetic field applied to the liquid suspension 53 by the permanent magnet 201 can be regarded as [0]. That is, position P5 is a position at which the application of the magnetic field on the liquid suspension 53 stops.

Position P1 is a position beneath the container install unit 75, and is a position directly under the container 100 installed in the container install unit 75 the same as the fifth embodiment. The permanent magnet 201 is moved from position P5 in the Z-axis negative direction to position P1. When the permanent magnet 201 is positioned at position P1, the permanent magnet 201 is positioned directly below the bottom part 141 of the housing part 140 the same as the case shown in FIG. 19A. In this way a magnetic field is applied in the horizontal direction relative to the liquid suspension 53 accommodated in the container 100, and the magnetic particles are linked in a chain in the horizontal direction. The magnetic force gradient in the vertical direction draws the magnetic particles to the bottom part 141.

In step S203, the controller 410 continues positioning the permanent magnet 201 at position P1 to await processing for a predetermined time. In this way the chain of magnetic particles enters a state of approaching the bottom part 141.

In step S241, the controller 410 moves the permanent magnet 201 from position P1 in the Z-axis positive direction toward position P5. As shown in FIG. 38, when positioned at position P5, the permanent magnet 201 is positioned the same as the case shown in FIG. 19B viewed in the X-axis direction. In step S222, the controller 410 waits a predetermined time to disperse the magnetic particles in the liquid suspension 53 to the bottom part 141 of the container 100. In this way substantially all the magnetic particles undergoing Brownian motion in the liquid suspension 53 are positioned at the bottom part 141, so as to form a monolayer in which the magnetic particles are dispersed on the bottom part 141 the same as the fifth embodiment. Accordingly, the target DNA molecules bound to the magnetic particles also can be accurately detected in the sixth embodiment.

The electromagnet 33 shown in FIGS. 21A and 21B also may be used instead of the permanent magnet 201 and moving device 202. The monolayering process in this case is changed as shown in FIG. 39.

Figure 39:
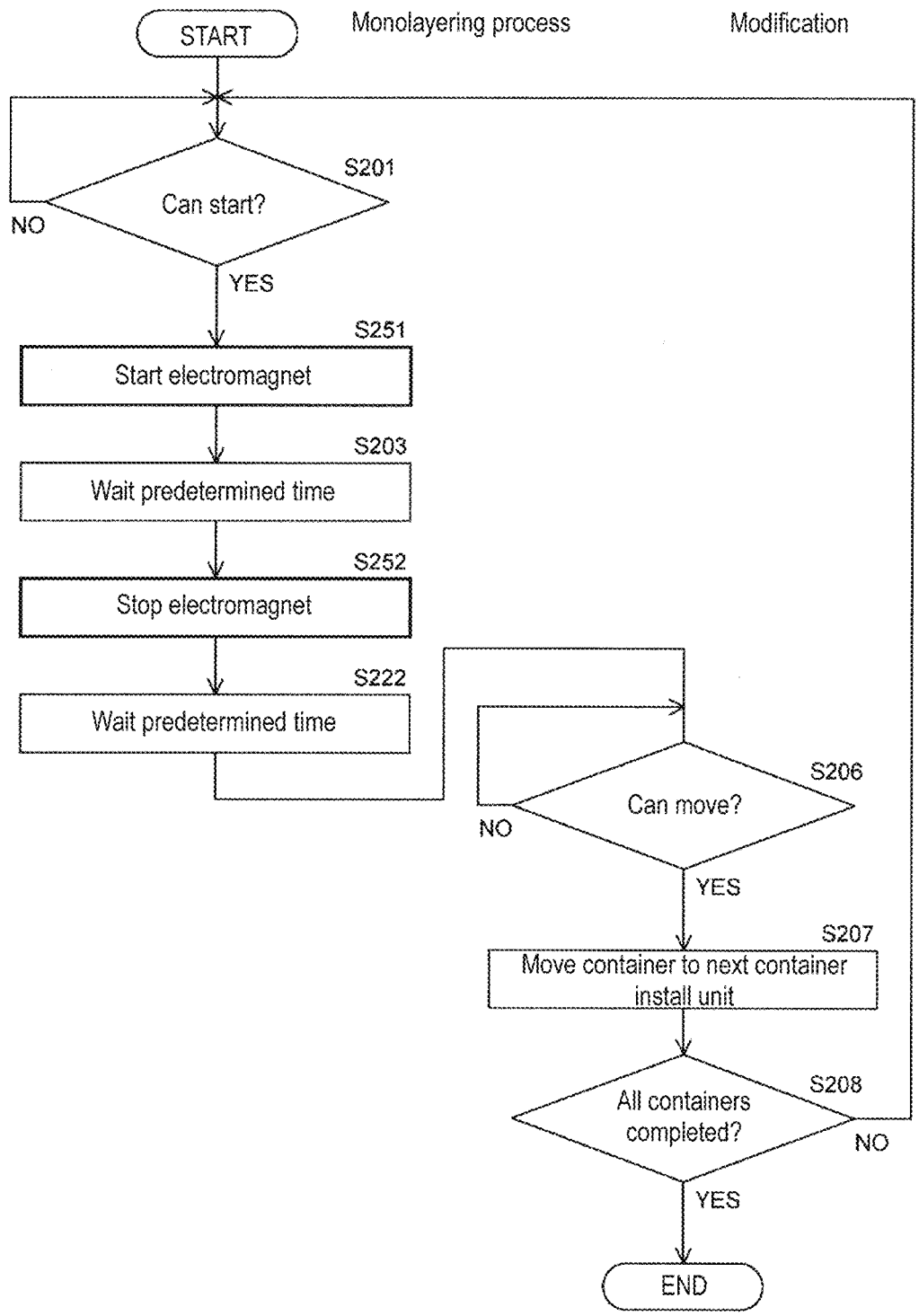
FIG. 39 is a flow chart showing the monolayering process in a modification of the sixth embodiment.

The monolayering process shown in FIG. 39 respectively adds steps S251 and S252 in place of steps S202 and S241 compared to FIG. 37. In step S251 the controller 410 actuates the electromagnet 33. In this way a magnetic field is applied substantially in a horizontal direction relative to the liquid suspension 53 the same as step S202 of FIG. 37 in the same state as FIG. 21A. The electromagnet 33 is moved downward a predetermined distance in step S251. In this way the magnetic particles are drawn to the bottom part 141. In step S252, the controller 410 stops the electromagnet 33. In this way the application of the magnetic field relative to the liquid suspension 53 is terminated the same as step S241 of FIG. 37 in the same state as FIG. 21B.

Magnetic Field Application Modification Examples

In the first through third embodiments, the permanent magnet 20 is arranged at the underside of the container 10, and the magnetic field is applied to the liquid suspension 16 from the bottom part 15a. However, the invention is not limited to this arrangement inasmuch as the permanent magnet 20 also may be arranged at the topside of the container 10, and the magnetic field may be applied to the liquid suspension 16 from the top part 15b of the housing part 15. In this case the bottom surface of the cover 14 is cationized, and the top surface 11a of the slide member 11 is not cationized. The top part 15b is part of the bottom surface of the cover 14, and has a positive surface charge through cationization. When imaging the bright-field image and the fluorescent images, the focus is near the top part 15a.

Figure 40A:
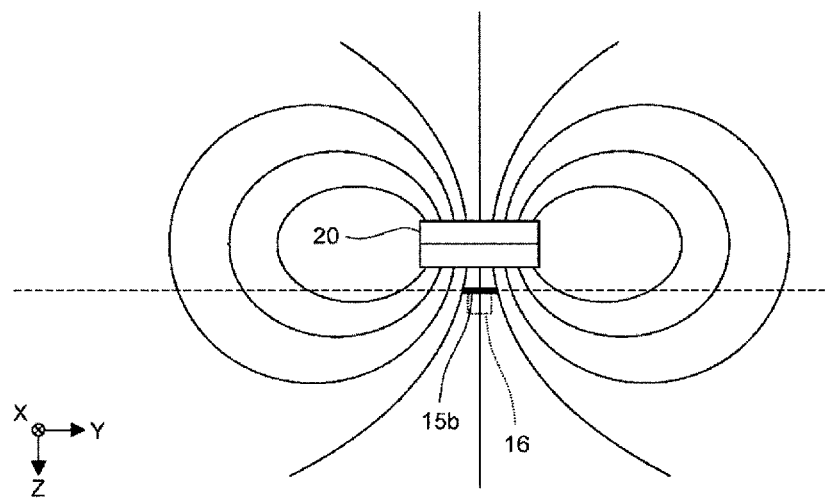
FIG. 40A is a schematic view showing the state of the direction of the magnetic field applied to the liquid suspension by the permanent magnet of a modification of the magnetic field application of the first embodiment is substantially perpendicular relative to the top part.
Figure 40B:
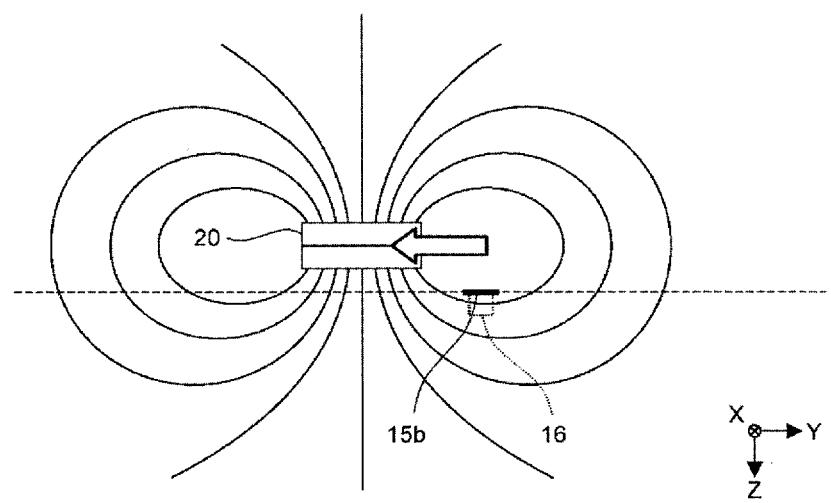
FIG. 40B is a schematic view showing the state of the direction of the magnetic field applied to the liquid suspension by the permanent magnet of the modification of the first embodiment is a direction substantially parallel relative to the top part.

FIGS. 40A and 40B are schematic views showing the structure when the permanent magnet 20 is arranged at the topside in the first embodiment.

In step S12 of FIG. 1, the permanent magnet 20 is positioned above the liquid suspension 16, as shown in FIG. 40A. In this way the direction of the magnetic field applied to the liquid suspension 16 is the vertical direction, and the plurality of magnetic particles are linked in a row from the top part 15b. In step S13 of FIG. 1, the permanent magnet 20 is moved in the horizontal direction as shown in FIG. 40B. In this way the direction of the magnetic field applied to the liquid suspension 16 becomes the horizontal direction, and the linked magnetic particles approach the top part 15b. Thus, the magnetic particles form a monolayer at the top part 15b.

Figure 41A:
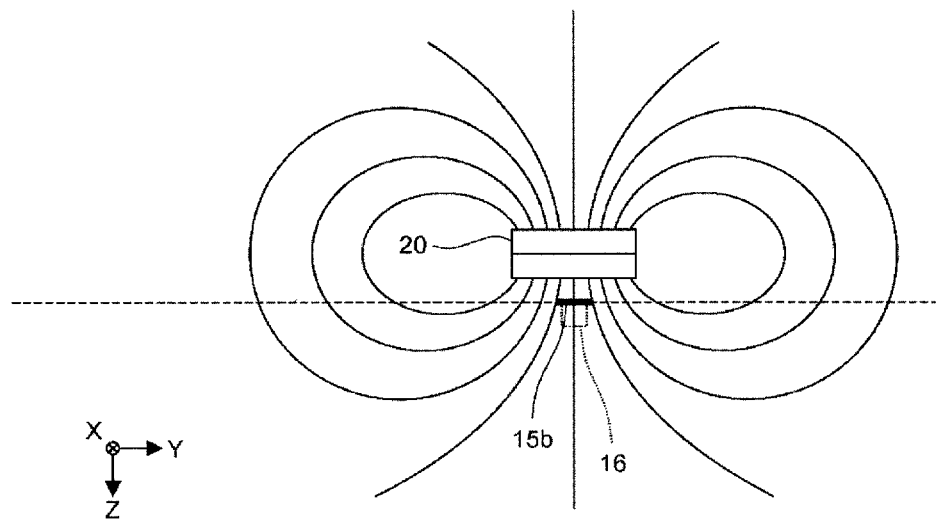
FIG. 41A is a schematic view showing the state of the direction of the magnetic field applied to the liquid suspension by the permanent magnet of a modification of the magnetic field application of the second embodiment is substantially perpendicular relative to the top part.
Figure 41B:
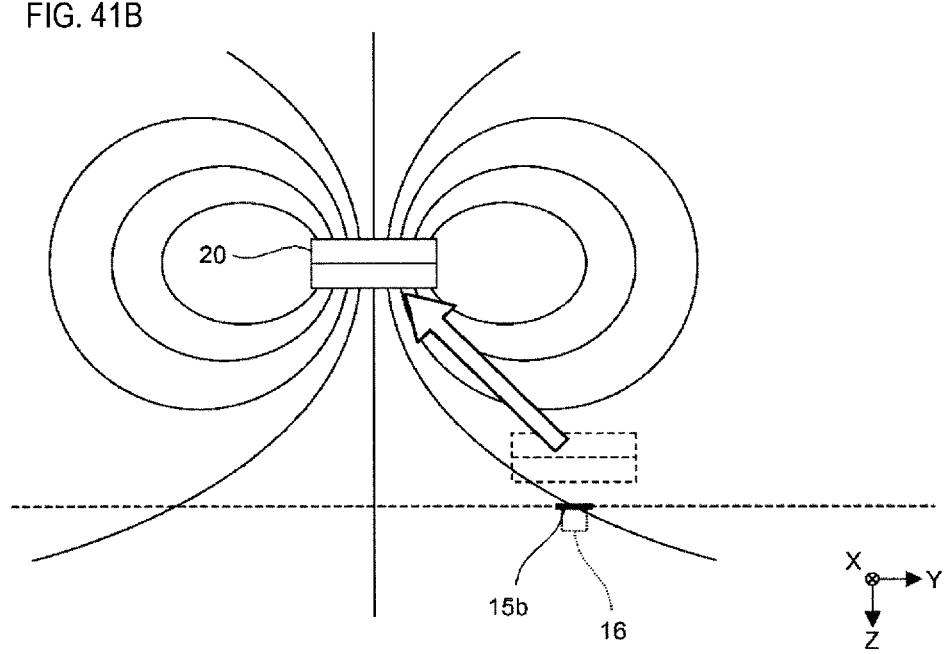
FIG. 41B is a schematic view showing the state of the direction of the magnetic field applied to the liquid suspension by the permanent magnet of the modification of the second embodiment is an oblique direction.

FIGS. 41A and 41B are schematic views showing the structure when the permanent magnet 20 is arranged at the topside in the second embodiment.

In step S22 of FIG. 8, the permanent magnet 20 is positioned above the liquid suspension 16, as shown in FIG. 41A. In this way a plurality of magnetic particles are linked in a row from the top part 15b. In step S23 of FIG. 8, the permanent magnet 20 is moved obliquely upward as shown in FIG. 41B. In this way the chain of magnetic particles is inclined. Thereafter, the permanent magnet 20 is moved further in the oblique upward direction. In this way the application of the magnetic field by the permanent magnet 20 is terminated, and the chain of magnetic particles linked in the oblique direction from the top part 15b collapses due to Brownian motion. This time the magnetic particles are positioned at the top part 15b against the force of gravity due to the Coulomb force between the particles and the top part 15b. Thus, the magnetic particles form a monolayer in a dispersed state at the top part 15b.

Figure 42A:
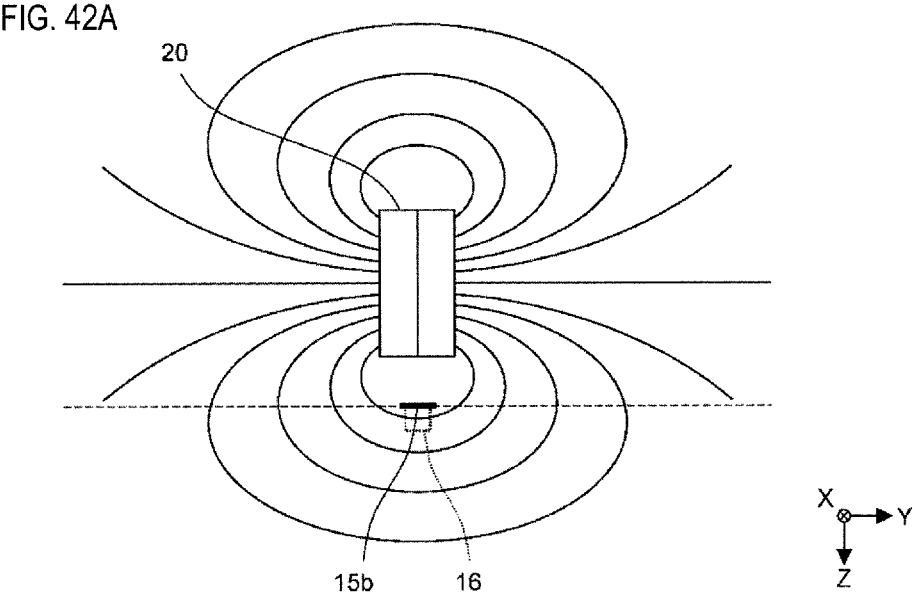
FIG. 42A is a schematic view showing the state of the direction of the magnetic field applied to the liquid suspension by the permanent magnet of a modification of the magnetic field application of the third embodiment is substantially perpendicular relative to the top part.
Figure 42B:
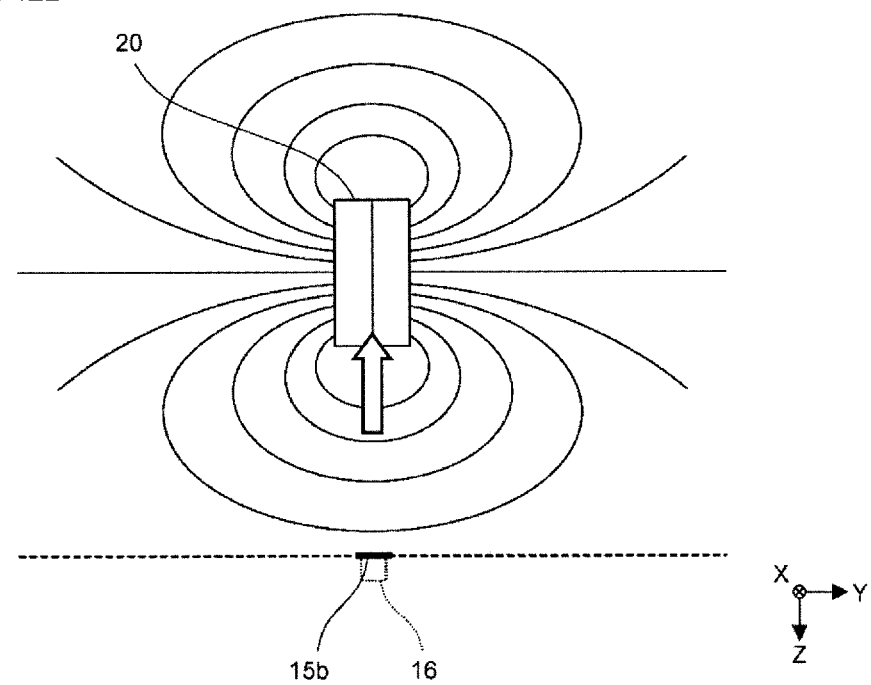
FIG. 42B is a schematic view showing the state of the magnetic field applied to the liquid suspension by the permanent magnet of the modification of the third embodiment can be viewed as [0].

FIGS. 42A and 42B are schematic views showing the structure when the permanent magnet 20 is arranged at the topside in the third embodiment.

In step S32 of FIG. 18, the permanent magnet 20 is positioned above the liquid suspension 16, as shown in FIG. 42A. In this way the direction of the magnetic field applied to the liquid suspension 16 is the horizontal direction, and the plurality of magnetic particles are linked in a row in the horizontal direction. The magnetic force gradient in the vertical direction draws the magnetic particles to the top part 15b. In step S33 of FIG. 18, the permanent magnet 20 is moved upward as shown in FIG. 42B. In this way the application of the magnetic field by the permanent magnet 20 is terminated, and the chain of magnetic particles drawn to the top part 15b collapses due to Brownian motion. This time the magnetic particles are positioned at the top part 15b against the force of gravity due to the Coulomb force between the particles and the top part 15b. Thus, the magnetic particles form a monolayer in a dispersed state at the top part 15b.

In the fourth through sixth embodiments, the permanent magnet 20 also may be arranged at the topside of the container 100, and the magnetic field may be applied to the liquid suspension 53 from the top part 142 of the housing part 140. In this case the bottom surface of the cover 130 is cationized, and the top surface 111 of the first member 110 is not cationized. The top part 142 is part of the bottom surface of the cover 130, and has a positive surface charge through cationization. When imaging the bright-field image and the fluorescent images, the focus is near the top part 142. The permanent magnet 201 is installed at the bottom surface of the vertical moving member 226 through the magnet support 230.

What is claimed is:

1. A detection method for detecting a detection target substance, comprising:
   a first application step of applying a magnetic field to a liquid suspension to link a plurality of magnetic particles in a row from an interior surface of a liquid receiving member that receives the liquid suspension of magnetic particles bound to a detection target substance, wherein at least a part of the liquid receiving member is made of a transparent material such that the interior surface is visible from an outside;
   a second application step of bringing the linked magnetic particles near the interior surface while the magnetic field is applied to the liquid suspension; and
   a detection step of imaging a plane of the interior surface and detecting the detection target substance bound to the magnetic particles shown in a plane image of the interior surface by digitally analyzing the image.

2. The detection method of claim 1, wherein
   the direction of the magnetic field applied to the liquid suspension is changed so the linked magnetic particles approach the interior surface in the second application step.

3. The detection method of claim 2, wherein
   the magnetic particles are linked by magnetic pole in the first application step; and
   the direction of the magnetic field applied to the liquid suspension is changed by moving the magnetic pole in a direction away from the liquid suspension in the second application step.

4. The detection method of claim 1, further comprising
   an application termination step of terminating the application of the magnetic field on the liquid suspension between the second application step and the detection step.

5. The detection method of claim 4, wherein
   the magnetic particles are linked by magnetic pole in the first application step; and
   the application of the magnetic field on the liquid suspension is terminated by moving the magnetic pole away from the liquid suspension in the application termination step.

6. The detection method of claim 4, wherein
   the detection step of detecting the detection target substance is performed after the elapse of a time set to disperse magnetic particles in the liquid suspension to the interior surface from the termination of the application of the magnetic field on the liquid suspension.

7. The detection method of claim 1, wherein
   the application of the magnetic field to the liquid suspension is continued during a time set for connecting magnetic particles in a chain in the liquid suspension in the first application step.

8. The detection method of claim 1, wherein
   the liquid suspension contains a surface active agent.

9. The detection method of claim 8, wherein
   the surface active agent is a nonionic surface active agent.

10. The detection method of claim 1, wherein
    the interior surface has a surface charge that is opposite a charge of the magnetic particles.

11. The detection method of claim 10, wherein
    the interior surface is cationized.

12. The detection method of claim 1, wherein
    the interior surface is a supporting surface that supports the liquid suspension from below.

13. The detection method of claim 1, wherein
    the liquid receiving member is a housing member that accommodates the liquid suspension; and
    the interior surface is a top surface or a bottom surface of the housing member.

14. The detection method of claim 1, wherein
    the detection target substance is at least one of a nucleic acid and protein.

15. A detection method for detecting a detection target substance, comprising:
    a magnetic field application step for applying a magnetic field to a liquid suspension to draw magnetic particles to an interior surface of a liquid receiving member that receives the liquid suspension of magnetic particles to which a detection target substance is bound, and to link a plurality of magnetic particles in a row in a direction that intersects a direction perpendicular to the interior surface, wherein at least a part of the liquid receiving member is made of a transparent material such that the interior surface is visible from an outside; and
    a detection step of imaging a plane of the interior surface and detecting the detection target substance bound to the magnetic particles shown in a plane image of the interior surface by digitally analyzing the image;
    wherein the liquid suspension contains a surface active agent.

16. A detection method for detecting a detection target substance, comprising:
    a magnetic field application step for applying a magnetic field to a liquid suspension to draw magnetic particles to an interior surface of a liquid receiving member that receives the liquid suspension of magnetic particles to which a detection target substance is bound, and to link a plurality of magnetic particles in a row in a direction that intersects a direction perpendicular to the interior surface, wherein at least a part of the liquid receiving member is made of a transparent material such that the interior surface is visible from an outside; and
    a detection step of imaging a plane of the interior surface and detecting the detection target substance bound to the magnetic particles shown in a plane image of the interior surface by digitally analyzing the image;
    wherein the interior surface has a surface charge that is opposite a charge of the magnetic particles.

* * * * *